(12) United States Patent
Morgan et al.

(10) Patent No.: US 6,180,377 B1
(45) Date of Patent: Jan. 30, 2001

(54) HUMANIZED ANTIBODIES

(75) Inventors: Susan Adrienne Morgan, Slough; John Spencer Emtage, Marlow; Mark William Bodmer, South Hinksey; Diljeet Singh Athwal, London, all of (GB)

(73) Assignee: Celltech Therapeutics Limited (GB)

( * ) Notice: Under 35 U.S.C. 154(b), the term of this patent shall be extended for 0 days.

(21) Appl. No.: 08/569,147

(22) PCT Filed: Jun. 15, 1993

(86) PCT No.: PCT/GB94/01291

§ 371 Date: Mar. 25, 1996

§ 102(e) Date: Mar. 25, 1996

(87) PCT Pub. No.: WO94/29451

PCT Pub. Date: Dec. 22, 1994

(30) Foreign Application Priority Data

Jun. 16, 1993 (GB) .................................................. 9312415
Jan. 27, 1994 (GB) .................................................. 9401597
Feb. 9, 1994 (GB) .................................................. 9402499
Mar. 29, 1994 (GB) .................................................. 9406222

(51) Int. Cl.$^7$ ............................ C12N 15/00; C12N 1/20; C07H 21/04; C07K 16/00

(52) U.S. Cl. ................................... 435/172.3; 435/320.1; 435/252.3; 435/325; 530/387.1; 530/387.3; 530/388.1; 536/23.1

(58) Field of Search .............................. 530/387.3, 172.3, 530/387.1, 388.1; 435/320.1, 252.3, 172.2, 325; 424/192.1, 141.1, 152.1; 536/23.1

(56) References Cited

FOREIGN PATENT DOCUMENTS

0068790 A1 * 1/1983 (EP) .
0239400 * 3/1987 (EP) .
0307434 B1 * 9/1993 (EP) .
WO 90/07861 * 7/1990 (WO) .
WO 91/09967 * 7/1991 (WO) .
WO 91/09968 * 7/1991 (WO) .
WO 92/01472 * 2/1992 (WO) .
WO 92/11383 * 7/1992 (WO) .

OTHER PUBLICATIONS

Gussow et al (Methods in Enzymology, 203:99–121, 1991.*
Burgess et al (J. Cell Bio, 111:2129–2138, 1990).*
Lazar et al (Mol. & Cell Bio, 8: 1247–1252, 1988).*
Tao et al, (J. Immunol, 143: 2595–2601, 1989).*
Arvin et al (Biochemistry, 1995, 34 : 5604–5609).*
Palmer et al (Immunogenetics, 1991, 33:12–17).*
Shackelford et al (J. Immunol, 1983, 130:289–296).*
Kualheim et al (J. Nat'l Gen.Inst., 1988, 1322–1325.*
Bebbington, C.R., et al., "High–Level Expression of a Recombinant Antibody From Myeloma Cells Using a Glutamine Synthetase Gene As An Amplifiable Selectable Marker", *Bio/Technology* 1992, 10, 169–175.*

Bebbington, C.R., "Expression of Antibody Genes In Non–lymphoid Mammalian Cells", *Methods: A Companion to Methods in Enzymology* 1991, 2(2), 136–145.*

Carter, P. et al., "Humanization of an Anti–p185$^{HER2}$ Antibody For Human Cancer Therapy", *PNAS USA* 1992, 89, 4285–4289.*

Co, M.S. et al., "Chimeric and Humanized Antibodies With Specificity For The CD33 Antigen", *The J. Of Immunology* 1992, 148(4), 1149–1154.*

Co., M.S. et al., "Humanized Antibodies For Antiviral Therapy", *PNAS USA* 1991, 88, 2869–2873.*

Cockett, M. et al., "The Use of Engineered E1A Genes to Transactivate the hCMV–MIE Promoter in Permanent CHO Cell Lines", *Nucleic Acids Res.* vol. 19(2), 319–325.*

Jones, P. et al., "Replacing the Complementarity–Determining Regions in a Human Antibody With Those From A Mouse", *Nature* 1986, 321, 522–525.*

Kramer, W. et al., "The Gapped Duplex DNA Approach to Oligonucleotide–Directed Mutation Construction", *Nucleic Acids Res.* 1984, 12(24), 9441–9456.*

Lampson, L. and Levy, "Two Populations of Ia–Like Molecules On a Human B Cell Line", *The J. Of Immunology* 1980, 125(1), 293–299.*

Morrison, S. et al., "Chimeric Human Antibody Molecules: Mouse Antigen–Binding Domains with Human Constant Region Domains", *PNAS USA* 1984, 81, 6851–6855.*

Routledge, E. et al., "A Humanized Monovalent CD3 Antibody Which Can Activate Homologou Complement", *Eur. J. Immunol.* 1991, 21, 2717–2725.*

Verhoeyen, M. et al., "Reshaping Human Antibodies: Grafting and Antilysozyme Activity", *Science* 1988, 239, 1534–1536.*

Whittle, N. et al., "Expression in COS Cells of a Mouse–Human Chimaeric B72.3 Antibody", *Protein Engineering* 1987, 1(6), 499–505.*

Wood, B.T. et al., "Fluorescent Antibody Staining. III. Preparation of Fluorescein–Isothiocyanate–Labeled Antibodies", *J. Of Immunol.* 1965, 95(2), 225–229.*

Queen, C. et al., "A Humanized Antibody That Binds to the Interleukin 2 Receptor", *PNAS USA* 1989, 86, 10029–10033.*

Riechmann, L. et al., "Reshaping Human Antibodies For Therapy", *Nature* 1988, 332, 323–327.*

* cited by examiner

*Primary Examiner*—Susan Ungar
(74) *Attorney, Agent, or Firm*—Woodcock Washburn Kurtz Mackiewicz & Norris LLP

(57) ABSTRACT

The invention describes humanized antibodies having specificity for the epitope recognised by the murine monoclonal antibody L243. Also described are processes for preparing said antibodies and pharmaceutical compositions and medical uses of said antibodies.

17 Claims, 22 Drawing Sheets

FIG. 1

Figure 3:
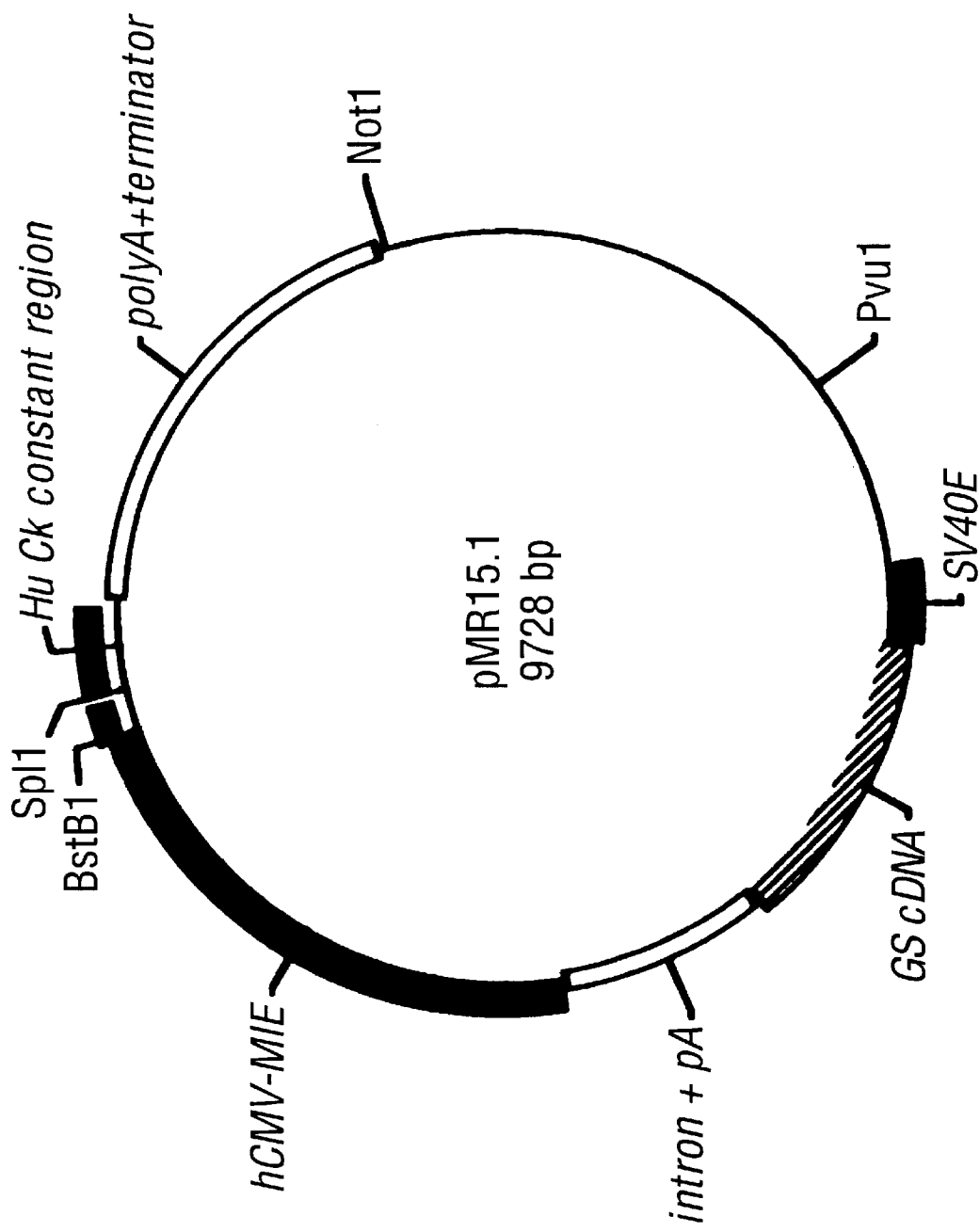

```
TTCGAAGCCGCCACC ATG AGG TGC TCT GCT GAG TTT CTG GGG TTG CTG
                 M   R   C   S   A   E   F   L   G   L   L>

CTG CTG TGG CTT ACA GAT GCC AGA TGT GAC ATC CAG ATG ACT CAG
 L   L   W   L   T   D   A   R   C   D   I   Q   M   T   Q>

TCT CCA GCC TCC CTA TCT GTA TCT GTG GGA GAA ACT GTC ACC ATC
 S   P   A   S   L   S   V   S   V   G   E   T   V   T   I>

ACA TGT CGA GCA AGT GAG AAT ATT TAC AGT AAT TTA GCA TGG TAT
 T   C   R   A   S   E   N   I   Y   S   N   L   A   W   Y>

CGT CAG AAA CAG GGA AAA TCT CCT CAG CTC CTG GTC TTT GCT GCA
 R   Q   K   Q   G   K   S   P   Q   L   L   V   F   A   A>

TCA AAC TTA GCA GAT GGT GTG CCA TCA AGG TTC AGT GGC AGT GGA
 S   N   L   A   D   G   V   P   S   R   F   S   G   S   G>

TCA GGC ACA CAG TAT TCC CTC AAG ATC AAC AGC CTG CAG TCT GAA
 S   G   T   Q   Y   S   L   K   I   N   S   L   Q   S   E>

GAT TTT GGG GAT TAT TAC TGT CAA CAT TTT TGG ACT ACT CCG TGG
 D   F   G   D   Y   Y   C   Q   H   F   W   T   T   P   W>

GCG TTC GGT GGA GGC ACC AAC CTG GAA ATC AAA CGT
 A   F   G   G   G   T   N   L   E   I   K   R>
```

FIG. 2

```
AAGCTTGCCGCCACC ATG GCT TGG GTG TGG AAC TTG CTA TTC CTG ATG
                 M   A   W   V   W   N   L   L   F   L   M>

GCA GCT GCC CAA AGT GCC CAA GCA CAG ATC CAG TTG GTG CAG TCT
 A   A   A   Q   S   A   Q   A   Q   I   Q   L   V   Q   S>

GGA CCT GAG CTG AAG AAG CCT GGA GAG ACA GTC AAG ATC TCC TGC
 G   P   E   L   K   K   P   G   E   T   V   K   I   S   C>

AAG GCT TCT GGG TTT ACC TTC ACA AAC TAT GGA ATG AAC TGG GTG
 K   A   S   G   F   T   F   T   N   Y   G   M   N   W   V>

AAG CAG GCT CCA GGA AAG GGT TTA AAG TGG ATG GGC TGG ATA AAC
 K   Q   A   P   G   K   G   L   K   W   M   G   W   I   N>

ACC TAC ACT AGA GAG CCA ACA TAT GCT GAT GAC TTC AAG GGA CGG
 T   Y   T   R   E   P   T   Y   A   D   D   F   K   G   R>

TTT GCC TTC TCT TTG GAA ACC TCT GCC AGC ACT GCC TAT TTG CAG
 F   A   F   S   L   E   T   S   A   S   T   A   Y   L   Q>

ATC AAC AAC CTC AAA AAT GAG GAC ACG GCT AAA TAT TTC TGT GCA
 I   N   N   L   K   N   E   D   T   A   K   Y   F   C   A>

AGA GAT ATT ACT GCG GTT GTA CCT ACG GGT TTT GAC TAC TGG GGC
 R   D   I   T   A   V   V   P   T   G   F   D   Y   W   G

CAA GGC ACC ACT CTC ACC GTC TCC TCA
 Q   G   T   T   L   T   V   S   S>
```

FIG. 4

```
TTCGAAGCCGCCACC ATG TCT GTC CCC ACC CAA GTC CTC GGT CTC CTG
                 M   S   V   P   T   Q   V   L   G   L   L>

CTG CTG TGG CTT ACA GAT GCC AGA TGT GAC ATT CAA ATG ACC CAG
 L   L   W   L   T   D   A   R   C   D   I   Q   M   T   Q>

AGC CCA TCC AGC CTG AGC GCA TCT GTA GGA GAC CGG GTC ACC ATC
 S   P   S   S   L   S   A   S   V   G   D   R   V   T   I>

ACA TGT CGA GCA AGT GAG AAT ATT TAC AGT AAT TTA GCA TGG TAT
 T   C   R   A   S   E   N   I   Y   S   N   L   A   W   Y>

CAG CAG AAA CCA GGA AAA GCT CCT CAG CTC CTG ATC TTT GCT GCA
 Q   Q   K   P   G   K   A   P   Q   L   L   I   F   A   A>

TCA AAC TTA GCA GAT GGT GTG CCA TCA AGG TTC AGT GGC AGT GGA
 S   N   L   A   D   G   V   P   S   R   F   S   G   S   G>

TCA GGC ACA CAG TAT ACC CTA ACT ATC TCC AGC CTG CAG CCA GAA
 S   G   T   Q   Y   T   L   T   I   S   S   L   Q   P   E>

GAT TTT GCT ACT TAT TAC TGT CAA CAT TTT TGG ACT ACT CCG TGG
 D   F   A   T   Y   Y   C   Q   H   F   W   T   T   P   W>

GCG TTC GGT CAA GGC ACC AAA GTG GAA ATC AAA CGT
 A   F   G   Q   G   T   K   V   E   I   K   R>
```

FIG. 5

```
TTCGAAGCCGCCACC ATG TCT GTC CCC ACC CAA GTC CTC GGT CTC CTG
                 M   S   V   P   T   Q   V   L   G   L   L>

CTG CTG TGG CTT ACA GAT GCC AGA TGT GAC ATT CAA ATG ACC CAG
 L   L   W   L   T   D   A   R   C   D   I   Q   M   T   Q>

AGC CCA TCC AGC CTG AGC GCA TCT GTA GGA GAC CGG GTC ACC ATC
 S   P   S   S   L   S   A   S   V   G   D   R   V   T   I>

ACA TGT CGA GCA AGT GAG AAT ATT TAC AGT AAT TTA GCA TGG TAT
 T   C   R   A   S   E   N   I   Y   S   N   L   A   W   Y>

CAG CAG AAA CCA GGA AAA GCT CCT AAG CTC CTG ATC TAT GCT GCA
 Q   Q   K   P   G   K   A   P   K   L   L   I   Y   A   A>

TCA AAC TTA GCA GAT GGT GTG CCA TCT AGA TTC AGT GGC AGT GGA
 S   N   L   A   D   G   V   P   S   R   F   S   G   S   G>

TCA GGC ACA GAC TTT ACC CTA ACT ATC TCC AGC CTG CAG CCA GAA
 S   G   T   D   F   T   L   T   I   S   S   L   Q   P   E>

GAT TTT GCT ACT TAT TAC TGT CAA CAT TTT TGG ACT ACT CCG TGG
 D   F   A   T   Y   Y   C   Q   H   F   W   T   T   P   W>

GCG TTC GGT CAA GGC ACC AAA GTG GAA ATC AAA CGT
 A   F   G   Q   G   T   K   V   E   I   K   R>
```

FIG. 7

```
AAGCTTGCCGCCACC ATG GAG TGG TCT TGG GTG TTC CTG TTC TTC CTG
                 M   E   W   S   W   V   F   L   F   F   L>

TCT GTG ACA ACA GGA GTG CAC TCT CAG GTG CAG CTG GTG CAG TCT
 S   V   T   T   G   V   H   S   Q   V   Q   L   V   Q   S>

GGA GCA GAG GTG AAG AAG CCT GGA GCA TCT GTG AAG GTG TCT TGT
 G   A   E   V   K   K   P   G   A   S   V   K   V   S   C>

AAG GCA TCT GGA TTC ACA TTC ACA AAT TAC GGA ATG AAT TGG GTG
 K   A   S   G   F   T   F   T   N   Y   G   M   N   W   V>

AGA CAG GCA CCT GGA CAG GGA CTC GAG TGG ATG GGA TGG ATT AAT
 R   Q   A   P   G   Q   G   L   E   W   M   G   W   I   N>

ACA TAC ACA AGA GAG CCT ACG TAC GCA GAC GAC TTC AAG GGA AGA
 T   Y   T   R   E   P   T   Y   A   D   D   F   K   G   R>

TTC ACA TTC ACA CTG GAG ACA TCT GCA TCT ACA GCA TAC ATG GAG
 F   T   F   T   L   E   T   S   A   S   T   A   Y   M   E>

CTG TCT TCT CTG AGA TCT GAG GAC ACA GCA GTG TAC TAC TGT GCA
 L   S   S   L   R   S   E   D   T   A   V   Y   Y   C   A>

AGA GAC ATT ACA GCA GTG GTA CCT ACA GGA TTC GAC TAC TGG GGA
 R   D   I   T   A   V   V   P   T   G   F   D   Y   W   G>

CAG GGA ACA CTG GTG ACA GTG TCT TCT
 Q   G   T   L   V   T   V   S   S>
```

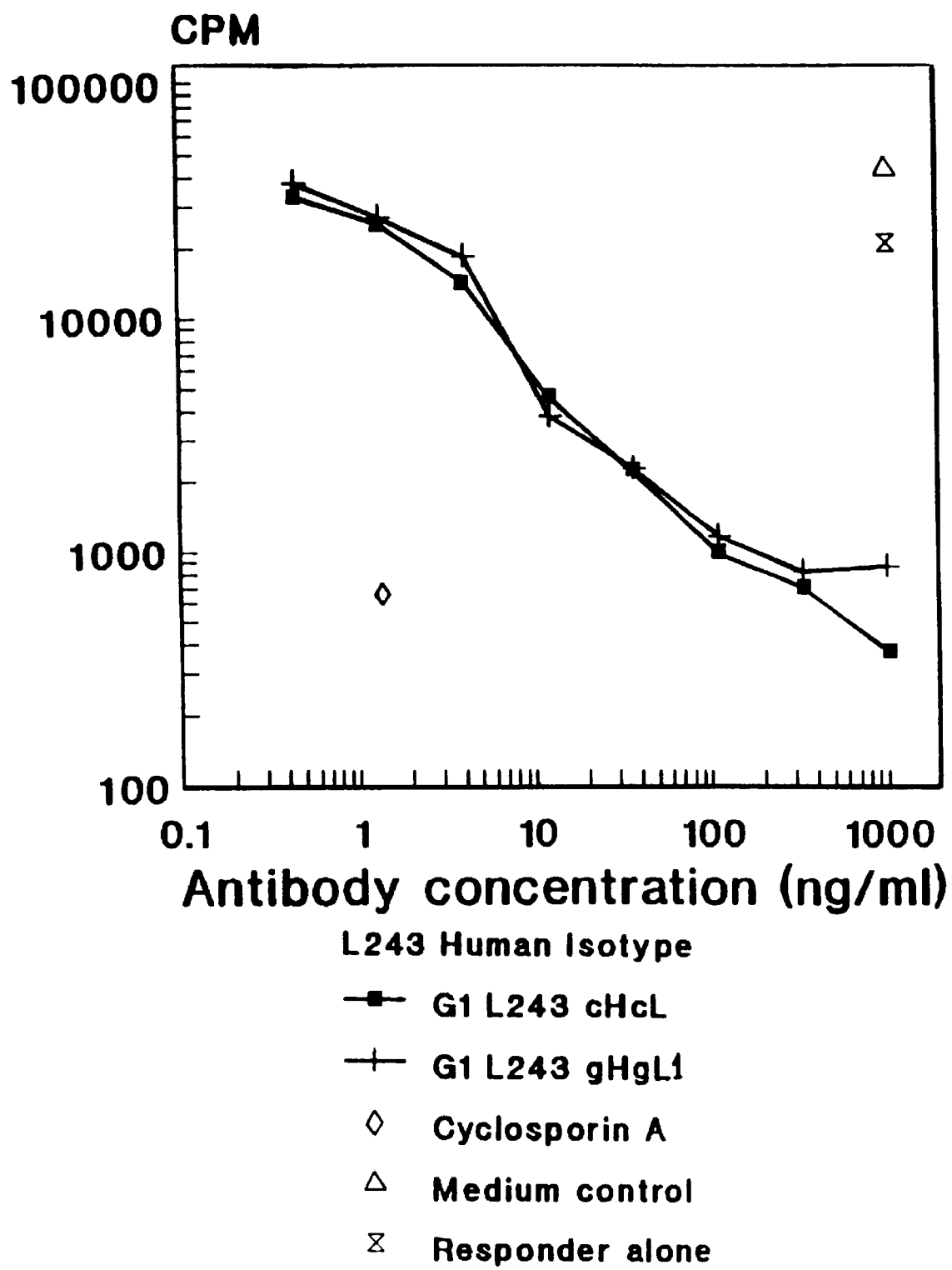

FIG. 14

```
       810           820           830           840           850           860
        *             *             *             *             *             *
ACCCC AAAGG CCAAA CTCTC CACTC CCTCA GCTCG GACAC CTTCT CTCCT CCCAG ATCTG
TGGGG TTTCC GGTTT GAGAG GTGAG GGAGT CGAGC CTGTG GAAGA GAGGA GGGTC TAGAC 870           880           890           900           910           920
        *             *             *             *             *             *
AGTAA CTCCC AATCT TCTCT CTGCA GAG CCC AAA TCT TGT GAC AAA ACT CAC ACA
TCATT GAGGG TTAGA AGAGA GACGT CTC GGG TTT AGA ACA CTG TTT TGA GTG TGT
                                 E   P   K   S   C   D   K   T   H   T>

930           940           950           960           970
        *             *             *             *             *
TGC CCA CCG TGC CCA GGTAA GCCAG CCCAG GCCTC GCCCT CCAGC TCAAG GCGGG
ACG GGT GGC ACG GGT CCATT CGGTC GGGTC CGGAG CGGGA GGTCG AGTTC CGCCC
 C   P   P   C   P>

980           990          1000          1010          1020          1030
        *             *             *             *             *             *
ACAGG TGCCC TAGAG TAGCC TGCAT CCAGG GACAG GCCCC AGCCG GGTGC TGACA CGTCC
TGTCC ACGGG ATCTC ATCGG ACGTA GGTCC CTGTC CGGGG TCGGC CCACG ACTGT GCAGG
```

```
         1040       1050       1060       1070       1080
   *          *          *          *          *          *
ACCTC CATCT CTTCC TCA GCA CCT GAA CTC CTG GGG GGA CCG TCA GTC TTC CTC
TGGAG GTAGA GAAGG AGT CGT GGA CTT GAG GAC CCC CCT GGC AGT CAG AAG GAG
                    A   P   E   L   L   G   G   P   S   V   F   L>

1090       1100       1110       1120       1130       1140
   *          *          *          *          *          *
TTC CCC CCA AAA CCC AAG GAC ACC CTC ATG ATC TCC CGG ACC CCT GAG GTC ACA
AAG GGG GGT TTT GGG TTC CTG TGG GAG TAC TAG AGG GCC TGG GGA CTC CAG TGT
 F   P   P   K   P   K   D   T   L   M   I   S   R   T   P   E   V   T>

1150       1160       1170       1180       1190
   *          *          *          *          *          *
TGC GTG GTG GAC GTG AGC CAC GAA GAC CCT GAG GTC AAG TTC AAC TGG TAC
ACG CAC CAC CTG CAC TCG GTG CTT CTG GGA CTC CAG TTC AAG TTG ACC ATG
 C   V   V   D   V   S   H   E   D   P   E   V   K   F   N   W   Y>

1200       1210       1220       1230       1240       1250
   *          *          *          *          *          *
GTG GAC GGC GTG GAG GTG CAT AAT GCC AAG ACA AAG CCG CGG GAG GAG CAG TAC
CAC CTG CCG CAC CTC CAC GTA TTA CGG TTC TGT TTC GGC GCC CTC CTC GTC ATG
 V   D   G   V   E   V   H   N   A   K   T   K   P   R   E   E   Q   Y>
```

FIG. 14 (CONTD.)

FIG. 19 a
```
  TTC GAA GCC GCC ACC ATG TGG GGA TCT GTT TTC CAT TTT TCA ATT GTA
  AAG CTT CGG CGG TGG TAC ACC CCT AGA CAA AAG GTA AAA AGT TAA CAT
                      M   W   G   S   V   F   H   F   S   I   V>

GAT GCC AGA TGT GAC ATC CAG ATG ACT CAG TCT CCA GCC TCC CTA TCT
  CTA CGG TCT ACA CTG TAG GTC TAC TGA GTC AGA GGT CGG AGG GAT AGA
   D   A   R   C   D   I   Q   M   T   Q   S   P   A   S   L   S>

GTA TCT GTG GGA GAA ACT GTC ACC ATC ACA TGT
  CAT AGA CAC CCT CTT TGA CAG TGG TAG TGT ACA
   V   S   V   G   E   T   V   T   I   T   C>
``` b
```
  TTC GAA GCC GCC ACC ATG AGG TGC TCT GCT GAG TTT CTG GGG TTG CTG
  AAG CTT CGG CGG TGG TAC TCC ACG AGA CGA CTC AAA GAC CCC AAC GAC
                      M   R   C   S   A   E   F   L   G   L   L>

CTG CTG TGG CTT ACA GAT GCC AGA TGT GAC ATC CAG ATG ACT CAG TCT
  GAC GAC ACC GAA TGT CTA CGG TCT ACA CTG TAG GTC TAC TGA GTC AGA
   L   L   W   L   T   D   A   R   C   D   I   Q   M   T   Q   S>

CCA GCC TCC CTA TCT GTA TCT GTG GGA GAA ACT GTC ACC ATC ACA TGT
  GGT CGG AGG GAT AGA CAT AGA CAC CCT CTT TGA CAG TGG TAG TGT ACA
   P   A   S   L   S   V   S   V   G   E   T   V   T   I   T   C>
```

```
C TTC GAA GCC GCC ACC ATG GGC ATC AAG ATG GAG TCA CAG TTC CAG GTC
  AAG CTT CGG CGG TGG TAC CCG TAG TTC TAC CTC AGT GTC AAG GTC CAG
                  M   G   I   K   M   E   S   Q   F   Q   V>

TTC ATA TCC ATA CTG CTC TGG TTA TAT GGA GCT GAT GGG AAC ATT GTA
AAG TAT AGG TAT GAC GAG ACC AAT ATA CCT CGA CTA CCC TTG TAA CAT
 F   I   S   I   L   L   W   L   Y   G   A   D   G   N   I   V>

ATG ACC CAA TCT CCC AAA TCC ATG TCC ATG TCA GTA GGA GAG AGG GTC
TAC TGG GTT AGA GGG TTT AGG TAC AGG TAC AGT CAT CCT CTC TCC CAG
 M   T   Q   S   P   K   S   M   S   M   S   V   G   E   R   V>

ACC TTG ACC TGC AAG GCC AGT GAG
TGG AAC TGG ACG TTC CGG TCA CTC
 T   L   T   C   K   A   S   E>
```

FIG. 19 (CONTD.)

SEQUENCE LISTING (1) GENERAL INFORMATION:

(iii) NUMBER OF SEQUENCES: 95

(2) INFORMATION FOR SEQ ID NO:1:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

GCACCTGAAC TCGAGGGGGG ACCGTCAGTC    30

(2) INFORMATION FOR SEQ ID NO:2:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

CCCCCCTCGA GTTCAGGTGC TGAGGAAG    28

(2) INFORMATION FOR SEQ ID NO:3:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:3:

GCACCTGAAC TCGCAGGGGG ACCGTCAGTC    30

(2) INFORMATION FOR SEQ ID NO:4:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:4:

GACTGACGGT CCCCCTGCGA GTTCAGGTGC    30

(2) INFORMATION FOR SEQ ID NO:5:

(i) SEQUENCE CHARACTERISTICS:
      (A) LENGTH: 30 base pairs

```
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GCACCTGAAC TCCTGGGTGC ACCGTCAGTC                              30

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GACTGACGGT GCACCCAGGA GTTCAGGTGC                              30

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GCACCTCCAG TGGCAGGACC GTCAGTCTTC CTC                          33

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

CGGTCCTGCC ACTGGAGGTG CTGAGGAAGA                              30

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CAGCTCGGAC ACCTTCTCTC CTCC                                    24

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO:10:

CCACCACCAC GCATGTGACC                                                    20

(2) INFORMATION FOR SEQ ID NO:11:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GCGCGCAAGC TTGCCGCCAC CATGAAATGC AGCTGGGTCA TSTTCTT                      47

(2) INFORMATION FOR SEQ ID NO:12:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GCGCGCAAGC TTGCCGCCAC CATGGGATGG AGCTRTATCA TSYTCTT                      47

(2) INFORMATION FOR SEQ ID NO:13:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GCGCGCAAGC TTGCCGCCAC CATGAAGWTG TGGTTAAACT GGGTTTT                      47

(2) INFORMATION FOR SEQ ID NO:14:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GCGCGCAAGC TTGCCGCCAC CATGRACTTT GGGYTCAGCT TGRT                         44

(2) INFORMATION FOR SEQ ID NO:15:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
GCGCGCAAGC TTGCCGCCAC CATGGACTCC AGGCTCAATT TAGTTTT                    47

(2) INFORMATION FOR SEQ ID NO:16:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GCGCGCAAGC TTGCCGCCAC CATGGCTGTC YTRGSGCTRC TCTTCTG                    47

(2) INFORMATION FOR SEQ ID NO:17:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GCGCGCAAGC TTGCCGCCAC CATGGRATGG AGCKGGRTCT TTMTCTT                    47

(2) INFORMATION FOR SEQ ID NO:18:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

GCGCGCAAGC TTGCCGCCAC CATGAGAGTG CTGATTCTTT TGTG                       44

(2) INFORMATION FOR SEQ ID NO:19:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

GCGCGCAAGC TTGCCGCCAC CATGGMTTGG GTGTGGAMCT TGCTATT                    47

(2) INFORMATION FOR SEQ ID NO:20:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

GCGCGCAAGC TTGCCGCCAC CATGGGCAGA CTTACATTCT CATTCCT                    47

(2) INFORMATION FOR SEQ ID NO:21:
```

(i) SEQUENCE CHARACTERISTICS:
  (A) LENGTH: 49 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:21:

GCGCGCAAGC TTGCCGCCAC CATGGATTTT GGGCTGATTT TTTTTATTG            49

(2) INFORMATION FOR SEQ ID NO:22:

(i) SEQUENCE CHARACTERISTICS:
    (A) LENGTH: 47 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:22:

GCGCGCAAGC TTGCCGCCAC CATGATGGTG TTAAGTCTTC TGTACCT              47

(2) INFORMATION FOR SEQ ID NO:23:

(i) SEQUENCE CHARACTERISTICS:
    (A) LENGTH: 50 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:23:

GGACTGTTCG AAGCCGCCAC CATGAAGTTG CCTGTTAGGC TGTTGGTGCT           50

(2) INFORMATION FOR SEQ ID NO:24:

(i) SEQUENCE CHARACTERISTICS:
    (A) LENGTH: 50 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:24:

GGACTGTTCG AAGCCGCCAC CATGGAGWCA GACACACTCC TGYTATGGGT           50

(2) INFORMATION FOR SEQ ID NO:25:

(i) SEQUENCE CHARACTERISTICS:
    (A) LENGTH: 44 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:25:

GGACTGTTCG AAGCCGCCAC CATGAGTGTG CTCACTCAGG TCCT                 44

(2) INFORMATION FOR SEQ ID NO:26:

(i) SEQUENCE CHARACTERISTICS:
    (A) LENGTH: 47 base pairs
    (B) TYPE: nucleic acid (C) STRANDEDNESS: single
        (D) TOPOLOGY: linear (ii) MOLECULE TYPE: cDNA (xi) SEQUENCE DESCRIPTION: SEQ ID NO:26:

GGACTGTTCG AAGCCGCCAC CATGAGGRCC CCTGCTCAGW TTYTTGG            47

(2) INFORMATION FOR SEQ ID NO:27:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

GGACTGTTCG AAGCCGCCAC CATGGATTTW CAGGTGCAGA TTWTCAGCTT          50

(2) INFORMATION FOR SEQ ID NO:28:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

GGACTGTTCG AAGCCGCCAC CATGAGGTKC YYTGYTSAGY TYCTGRG             47

(2) INFORMATION FOR SEQ ID NO:29:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

GGACTGTTCG AAGCCGCCAC CATGGGCWTC AAGATGGAGT CACA                44

(2) INFORMATION FOR SEQ ID NO:30:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

GGACTGTTCG AAGCCGCCAC CATGTGGGGA YCTKTTTYCM MTTTTTCAAT          50

(2) INFORMATION FOR SEQ ID NO:31:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

GGACTGTTCG AAGCCGCCAC CATGGTRTCC WCASCTCAGT TCCTT                45

(2) INFORMATION FOR SEQ ID NO:32:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

GGACTGTTCG AAGCCGCCAC CATGTATATA TGTTTGTTGT CTATTTC              47

(2) INFORMATION FOR SEQ ID NO:33:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

GGACTGTTCG AAGCCGCCAC CATGGAAGCC CCAGCTCAGC TTCTCTT              47

(2) INFORMATION FOR SEQ ID NO:34:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

GGATACAGTT GGTGCAGCAT CCGTACGTTT                                 30

(2) INFORMATION FOR SEQ ID NO:35:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

GCAGATGGGC CCTTCGTTGA GGCTGMRGAG ACDGTGA                         37

(2) INFORMATION FOR SEQ ID NO:36:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

Asp Ile Gln Met Thr Gln Ser Pro Ser Ser Leu Ser Ala Ser Val Gly

```
1               5                  10                 15
Asp Arg Val Thr Ile Thr Cys
                20
```

(2) INFORMATION FOR SEQ ID NO:37:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

```
Asp Ile Gln Met Thr Gln Ser Pro Ala Ser Leu Ser Val Ser Val Gly
1               5                  10                 15
Glu Thr Val Thr Ile Thr Cys
                20
```

(2) INFORMATION FOR SEQ ID NO:38:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

```
Trp Tyr Gln Gln Lys Pro Gly Lys Ala Pro Lys Leu Leu Ile Tyr
1               5                  10                 15
```

(2) INFORMATION FOR SEQ ID NO:39:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

```
Trp Tyr Arg Gln Lys Gln Gly Lys Ser Pro Gln Leu Leu Val Phe
1               5                  10                 15
```

(2) INFORMATION FOR SEQ ID NO:40:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:40:

```
Gly Val Pro Ser Arg Phe Ser Gly Ser Gly Ser Gly Thr Asp Phe Thr
1               5                  10                 15
Leu Thr Ile Ser Ser Leu Gln Pro Glu Asp Phe Ala Thr Tyr Tyr Cys
                20                 25                 30
```

(2) INFORMATION FOR SEQ ID NO:41:

(i) SEQUENCE CHARACTERISTICS:

(A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:41:

Gly Val Pro Ser Arg Phe Ser Gly Ser Gly Ser Gly Thr Gln Tyr Ser
1               5                  10                  15

Leu Lys Ile Asn Ser Leu Gln Ser Glu Asp Phe Gly Asp Tyr Tyr Cys
            20                  25                  30

(2) INFORMATION FOR SEQ ID NO:42:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:42:

Phe Gly Gln Gly Thr Lys Val Glu Ile Lys Arg
1               5                  10

(2) INFORMATION FOR SEQ ID NO:43:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:43:

Phe Gly Gly Gly Thr Asn Leu Glu Ile Lys Arg
1               5                  10

(2) INFORMATION FOR SEQ ID NO:44:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

GTAGGAGACC GGGTCACCAT CACATGTCGA GCAA                                        34

(2) INFORMATION FOR SEQ ID NO:45:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

CTGAGGAGCT TTTCCTGGTT TCTGCTGATA CCATGCTAAA                                  40

(2) INFORMATION FOR SEQ ID NO:46:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

AAACCAGGAA AAGCTCCTCA GCTCCTGATC TTTGCTGCAT C                41

(2) INFORMATION FOR SEQ ID NO:47:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

CTTCTGGCTG CAGGCTGGAG ATAGTTAGGG TATACTGTGT GCC              43

(2) INFORMATION FOR SEQ ID NO:48:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

CTTCAGCCTG CAGCCAGAAG ATTTTGCTAC TTATTACTGT CAA              43

(2) INFORMATION FOR SEQ ID NO:49:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:49:

GGGCCGCTAC CGTACGTTTT AGTTCCACTT TGGTGCCTTG ACCGAA           46

(2) INFORMATION FOR SEQ ID NO:50:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:50:

GCTGACAGAC TAACAGACTG TTCC                                   24

(2) INFORMATION FOR SEQ ID NO:51:

(i) SEQUENCE CHARACTERISTICS:
        (A) LENGTH: 57 base pairs
        (B) TYPE: nucleic acid (C) STRANDEDNESS: single
        (D) TOPOLOGY: linear (ii) MOLECULE TYPE: cDNA (xi) SEQUENCE DESCRIPTION: SEQ ID NO:51:

TCTAGATGGC ACACCATCTG CTAAGTTTGA TGCAGCATAG ATCAGGAGCT TAGGAGC     57

(2) INFORMATION FOR SEQ ID NO:52:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:52:

GCAGATGGTG TGCCATCTAG ATTCAGTGGC AGTGGATCAG GCACAGACTT TACCCTAAC     59

(2) INFORMATION FOR SEQ ID NO:53:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:53:

TTCAACTGCT CATCAGAT     18

(2) INFORMATION FOR SEQ ID NO:54:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:54:

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

(2) INFORMATION FOR SEQ ID NO:55:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:55:

Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Phe Thr
            20                  25                  30
    INFORMATION FOR SEQ ID NO:56:

(i) SEQUENCE CHARACTERISTICS:

(A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:56:

Trp Val Arg Gln Ala Pro Gly Gln Gly Leu Glu Trp Met Gly
1               5                  10

(2) INFORMATION FOR SEQ ID NO:57:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:57:

Trp Val Lys Gln Ala Pro Gly Lys Gly Leu Lys Trp Met Gly
1               5                  10

(2) INFORMATION FOR SEQ ID NO:58:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:58:

Arg Val Thr Ile Thr Ala Asp Thr Ser Thr Ser Thr Ala Tyr Met Glu
1               5                  10                  15

Leu Ser Ser Leu Arg Ser Glu Asp Thr Ala Val Tyr Tyr Cys Ala Arg
            20                  25                  30

(2) INFORMATION FOR SEQ ID NO:59:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:59:

Arg Phe Ala Phe Ser Leu Glu Thr Ser Ala Ser Thr Ala Tyr Leu Gln
1               5                  10                  15

Ile Asn Asn Leu Lys Asn Glu Asp Thr Ala Lys Tyr Phe Cys Ala Arg
            20                  25                  30

(2) INFORMATION FOR SEQ ID NO:60:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:60:

```
Trp Gly Gln Gly Thr Leu Val Thr Val Ser Ser
1               5                   10
```

(2) INFORMATION FOR SEQ ID NO:61:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:61:

```
Trp Gly Gln Gly Thr Thr Leu Thr Val Ser Ser
1               5                   10
```

(2) INFORMATION FOR SEQ ID NO:62:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:62:

```
GGGGGGAAGC TTGCCGCCAC CATGG                                    25
```

(2) INFORMATION FOR SEQ ID NO:63:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:63:

```
CCCCCCGGGC CCTTTGTAGA AGCAG                                    25
```

(2) INFORMATION FOR SEQ ID NO:64:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:64:

```
GACAACAGGA GTGCACTCTC AGGTGCAGCT GGTGCAGTCT GGAGCAGAGG TGAAGAAGCC    60

TGGAGCATCT G                                                         71
```

(2) INFORMATION FOR SEQ ID NO:65:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:65:

```
ACATTCACAA ATTACGGAAT GAATTGGGTG AGACAGGCAC CTGGACAGGG ACTCGAGTGG      60

A                                                                     61
```

(2) INFORMATION FOR SEQ ID NO:66:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:66:

```
CCTACGTACG CAGACGACTT CAAGGGAAGA TTCACATTCA CACTGGAGAC ATCTGCATCT      60

ACAGCATACA T                                                          71
```

(2) INFORMATION FOR SEQ ID NO:67:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:67:

```
CAGCAGTGTA CTACTGTGCA AGAGACATTA CAGCAGTGGT ACCTACAGGA TTCGACTACT      60

GGGGACAGGG A                                                          71
```

(2) INFORMATION FOR SEQ ID NO:68:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:68:

```
TGAGAGTGCA CTCCTGTTGT CACAGACAGG AAGAACAGGA ACACCCAAGA CCACTCCATG      60

GTGGCGGCAA GCTTCCCCCC                                                 80
```

(2) INFORMATION FOR SEQ ID NO:69:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:69:

```
CATTCCGTAA TTTGTGAATG TGAATCCAGA TGCCTTACAA GACACCTTCA CAGATGCTCC      60

AGGCTTCTTC A                                                          71
```

(2) INFORMATION FOR SEQ ID NO:70:

(i) SEQUENCE CHARACTERISTICS:
        (A) LENGTH: 71 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:70:

GAAGTCGTCT GCGTACGTAG GCTCTCTTGT GTATGTATTA ATCCATCCCA TCCACTCGAG        60

TCCCTGTCCA G                                                            71

(2) INFORMATION FOR SEQ ID NO:71:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:71:

TTGCACAGTA GTACACTGCT GTGTCCTCAG ATCTCAGAGA AGACAGCTCC ATGTATGCTG        60

TAGATGCAGA T                                                            71

(2) INFORMATION FOR SEQ ID NO:72:

(i) SEQUENCE CHARACTERISTICS:
            (A) LENGTH: 65 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:72:

CCCCCCGGGC CCTTTGTAGA AGCAGAAGAC ACTGTCACCA GTGTTCCCTG TCCCCAGTAG        60

TCGAA                                                                   65

(2) INFORMATION FOR SEQ ID NO:73:

(i) SEQUENCE CHARACTERISTICS:
            (A) LENGTH: 399 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 16..399

(xi) SEQUENCE DESCRIPTION: SEQ ID NO:73:

TTCGAAGCCG CCACC ATG AGG TGC TCT GCT GAG TTT CTG GGG TTG CTG CTG        51
                Met Arg Cys Ser Ala Glu Phe Leu Gly Leu Leu Leu
                 1               5                  10

CTG TGG CTT ACA GAT GCC AGA TGT GAC ATC CAG ATG ACT CAG TCT CCA         99
Leu Trp Leu Thr Asp Ala Arg Cys Asp Ile Gln Met Thr Gln Ser Pro
            15                  20                  25

GCC TCC CTA TCT GTA TCT GTG GGA GAA ACT GTC ACC ATC ACA TGT CGA        147
Ala Ser Leu Ser Val Ser Val Gly Glu Thr Val Thr Ile Thr Cys Arg
        30                  35                  40

GCA AGT GAG AAT ATT TAC AGT AAT TTA GCA TGG TAT CGT CAG AAA CAG        195
Ala Ser Glu Asn Ile Tyr Ser Asn Leu Ala Trp Tyr Arg Gln Lys Gln
    45                  50                  55                  60

GGA AAA TCT CCT CAG CTC CTG GTC TTT GCT GCA TCA AAC TTA GCA GAT        243
Gly Lys Ser Pro Gln Leu Leu Val Phe Ala Ala Ser Asn Leu Ala Asp

```
                  65                  70                  75
GGT GTG CCA TCA AGG TTC AGT GGC AGT GGA TCA GGC ACA CAG TAT TCC      291
Gly Val Pro Ser Arg Phe Ser Gly Ser Gly Ser Gly Thr Gln Tyr Ser
            80                  85                  90

CTC AAG ATC AAC AGC CTG CAG TCT GAA GAT TTT GGG GAT TAT TAC TGT      339
Leu Lys Ile Asn Ser Leu Gln Ser Glu Asp Phe Gly Asp Tyr Tyr Cys
        95                 100                 105

CAA CAT TTT TGG ACT ACT CCG TGG GCG TTC GGT GGA GGC ACC AAC CTG      387
Gln His Phe Trp Thr Thr Pro Trp Ala Phe Gly Gly Gly Thr Asn Leu
    110                 115                 120

GAA ATC AAA CGT                                                      399
Glu Ile Lys Arg
125

(2) INFORMATION FOR SEQ ID NO:74:

(i) SEQUENCE CHARACTERISTICS:
        (A) LENGTH: 128 amino acids
        (B) TYPE: amino acid
        (D) TOPOLOGY: linear (ii) MOLECULE TYPE: protein (xi) SEQUENCE DESCRIPTION: SEQ ID NO:74:

Met Arg Cys Ser Ala Glu Phe Leu Gly Leu Leu Leu Leu Trp Leu Thr
  1               5                  10                  15

Asp Ala Arg Cys Asp Ile Gln Met Thr Gln Ser Pro Ala Ser Leu Ser
                 20                  25                  30

Val Ser Val Gly Glu Thr Val Thr Ile Thr Cys Arg Ala Ser Glu Asn
             35                  40                  45

Ile Tyr Ser Asn Leu Ala Trp Tyr Arg Gln Lys Gln Gly Lys Ser Pro
         50                  55                  60

Gln Leu Leu Val Phe Ala Ala Ser Asn Leu Ala Asp Gly Val Pro Ser
 65                  70                  75                  80

Arg Phe Ser Gly Ser Gly Ser Gly Thr Gln Tyr Ser Leu Lys Ile Asn
                 85                  90                  95

Ser Leu Gln Ser Glu Asp Phe Gly Asp Tyr Tyr Cys Gln His Phe Trp
            100                 105                 110

Thr Thr Pro Trp Ala Phe Gly Gly Gly Thr Asn Leu Glu Ile Lys Arg
        115                 120                 125

(2) INFORMATION FOR SEQ ID NO:75:

(i) SEQUENCE CHARACTERISTICS:
        (A) LENGTH: 435 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 16..435

(xi) SEQUENCE DESCRIPTION: SEQ ID NO:75:

AAGCTTGCCG CCACC ATG GCT TGG GTG TGG AAC TTG CTA TTC CTG ATG GCA     51
                Met Ala Trp Val Trp Asn Leu Leu Phe Leu Met Ala
                  1               5                  10

GCT GCC CAA AGT GCC CAA GCA CAG ATC CAG TTG GTG CAG TCT GGA CCT      99
Ala Ala Gln Ser Ala Gln Ala Gln Ile Gln Leu Val Gln Ser Gly Pro
            15                  20                  25
```

```
GAG CTG AAG AAG CCT GGA GAG ACA GTC AAG ATC TCC TGC AAG GCT TCT      147
Glu Leu Lys Lys Pro Gly Glu Thr Val Lys Ile Ser Cys Lys Ala Ser
    30                  35                  40

GGG TTT ACC TTC ACA AAC TAT GGA ATG AAC TGG GTG AAG CAG GCT CCA      195
Gly Phe Thr Phe Thr Asn Tyr Gly Met Asn Trp Val Lys Gln Ala Pro
45                  50                  55                  60

GGA AAG GGT TTA AAG TGG ATG GGC TGG ATA AAC ACC TAC ACT AGA GAG      243
Gly Lys Gly Leu Lys Trp Met Gly Trp Ile Asn Thr Tyr Thr Arg Glu
                65                  70                  75

CCA ACA TAT GCT GAT GAC TTC AAG GGA CGG TTT GCC TTC TCT TTG GAA      291
Pro Thr Tyr Ala Asp Asp Phe Lys Gly Arg Phe Ala Phe Ser Leu Glu
            80                  85                  90

ACC TCT GCC AGC ACT GCC TAT TTG CAG ATC AAC AAC CTC AAA AAT GAG      339
Thr Ser Ala Ser Thr Ala Tyr Leu Gln Ile Asn Asn Leu Lys Asn Glu
        95                  100                 105

GAC ACG GCT AAA TAT TTC TGT GCA AGA GAT ATT ACT GCG GTT GTA CCT      387
Asp Thr Ala Lys Tyr Phe Cys Ala Arg Asp Ile Thr Ala Val Val Pro
    110                 115                 120

ACG GGT TTT GAC TAC TGG GGC CAA GGC ACC ACT CTC ACC GTC TCC TCA      435
Thr Gly Phe Asp Tyr Trp Gly Gln Gly Thr Thr Leu Thr Val Ser Ser
125                 130                 135                 140
```

(2) INFORMATION FOR SEQ ID NO:76:

(i) SEQUENCE CHARACTERISTICS:
        (A) LENGTH: 140 amino acids
        (B) TYPE: amino acid
        (D) TOPOLOGY: linear (ii) MOLECULE TYPE: protein (xi) SEQUENCE DESCRIPTION: SEQ ID NO:76:

```
Met Ala Trp Val Trp Asn Leu Leu Phe Leu Met Ala Ala Ala Gln Ser
1               5                   10                  15

Ala Gln Ala Gln Ile Gln Leu Val Gln Ser Gly Pro Glu Leu Lys Lys
                20                  25                  30

Pro Gly Glu Thr Val Lys Ile Ser Cys Lys Ala Ser Gly Phe Thr Phe
            35                  40                  45

Thr Asn Tyr Gly Met Asn Trp Val Lys Gln Ala Pro Gly Lys Gly Leu
        50                  55                  60

Lys Trp Met Gly Trp Ile Asn Thr Tyr Thr Arg Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Lys
            100                 105                 110

Tyr Phe Cys Ala Arg Asp Ile Thr Ala Val Val Pro Thr Gly Phe Asp
        115                 120                 125

Tyr Trp Gly Gln Gly Thr Thr Leu Thr Val Ser Ser
130                 135                 140
```

(2) INFORMATION FOR SEQ ID NO:77:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (ii) MOLECULE TYPE: cDNA (ix) FEATURE:

(A) NAME/KEY: CDS
        (B) LOCATION: 16..399

(xi) SEQUENCE DESCRIPTION: SEQ ID NO:77:

TTCGAAGCCG CCACC ATG TCT GTC CCC ACC CAA GTC CTC GGT CTC CTG CTG      51
               Met Ser Val Pro Thr Gln Val Leu Gly Leu Leu Leu
                 1               5                  10

CTG TGG CTT ACA GAT GCC AGA TGT GAC ATT CAA ATG ACC CAG AGC CCA       99
Leu Trp Leu Thr Asp Ala Arg Cys Asp Ile Gln Met Thr Gln Ser Pro
        15                  20                  25

TCC AGC CTG AGC GCA TCT GTA GGA GAC CGG GTC ACC ATC ACA TGT CGA      147
Ser Ser Leu Ser Ala Ser Val Gly Asp Arg Val Thr Ile Thr Cys Arg
 30                  35                  40

GCA AGT GAG AAT ATT TAC AGT AAT TTA GCA TGG TAT CAG CAG AAA CCA      195
Ala Ser Glu Asn Ile Tyr Ser Asn Leu Ala Trp Tyr Gln Gln Lys Pro
 45                  50                  55                  60

GGA AAA GCT CCT CAG CTC CTG ATC TTT GCT GCA TCA AAC TTA GCA GAT      243
Gly Lys Ala Pro Gln Leu Leu Ile Phe Ala Ala Ser Asn Leu Ala Asp
                 65                  70                  75

GGT GTG CCA TCA AGG TTC AGT GGC AGT GGA TCA GGC ACA CAG TAT ACC      291
Gly Val Pro Ser Arg Phe Ser Gly Ser Gly Ser Gly Thr Gln Tyr Thr
         80                  85                  90

CTA ACT ATC TCC AGC CTG CAG CCA GAA GAT TTT GCT ACT TAT TAC TGT      339
Leu Thr Ile Ser Ser Leu Gln Pro Glu Asp Phe Ala Thr Tyr Tyr Cys
             95                 100                 105

CAA CAT TTT TGG ACT ACT CCG TGG GCG TTC GGT CAA GGC ACC AAA GTG      387
Gln His Phe Trp Thr Thr Pro Trp Ala Phe Gly Gln Gly Thr Lys Val
        110                 115                 120

GAA ATC AAA CGT                                                      399
Glu Ile Lys Arg
125

(2) INFORMATION FOR SEQ ID NO:78:

(i) SEQUENCE CHARACTERISTICS:
        (A) LENGTH: 128 amino acids
        (B) TYPE: amino acid
        (D) TOPOLOGY: linear (ii) MOLECULE TYPE: protein (xi) SEQUENCE DESCRIPTION: SEQ ID NO:78:

Met Ser Val Pro Thr Gln Val Leu Gly Leu Leu Leu Trp Leu Thr
 1               5                  10                  15

Asp Ala Arg Cys Asp Ile Gln Met Thr Gln Ser Pro Ser Ser Leu Ser
                 20                  25                  30

Ala Ser Val Gly Asp Arg Val Thr Ile Thr Cys Arg Ala Ser Glu Asn
         35                  40                  45

Ile Tyr Ser Asn Leu Ala Trp Tyr Gln Gln Lys Pro Gly Lys Ala Pro
     50                  55                  60

Gln Leu Leu Ile Phe Ala Ala Ser Asn Leu Ala Asp Gly Val Pro Ser
 65                  70                  75                  80

Arg Phe Ser Gly Ser Gly Ser Gly Thr Gln Tyr Thr Leu Thr Ile Ser
                 85                  90                  95

Ser Leu Gln Pro Glu Asp Phe Ala Thr Tyr Tyr Cys Gln His Phe Trp
                100                 105                 110

Thr Thr Pro Trp Ala Phe Gly Gln Gly Thr Lys Val Glu Ile Lys Arg
        115                 120                 125

(2) INFORMATION FOR SEQ ID NO:79:

(i) SEQUENCE CHARACTERISTICS:
            (A) LENGTH: 399 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 16..399

(xi) SEQUENCE DESCRIPTION: SEQ ID NO:79:

TTCGAAGCCG CCACC ATG TCT GTC CCC ACC CAA GTC CTC GGT CTC CTG CTG            51
                Met Ser Val Pro Thr Gln Val Leu Gly Leu Leu Leu
                 1               5                  10

CTG TGG CTT ACA GAT GCC AGA TGT GAC ATT CAA ATG ACC CAG AGC CCA             99
Leu Trp Leu Thr Asp Ala Arg Cys Asp Ile Gln Met Thr Gln Ser Pro
         15                  20                  25

TCC AGC CTG AGC GCA TCT GTA GGA GAC CGG GTC ACC ATC ACA TGT CGA            147
Ser Ser Leu Ser Ala Ser Val Gly Asp Arg Val Thr Ile Thr Cys Arg
     30                  35                  40

GCA AGT GAG AAT ATT TAC AGT AAT TTA GCA TGG TAT CAG CAG AAA CCA            195
Ala Ser Glu Asn Ile Tyr Ser Asn Leu Ala Trp Tyr Gln Gln Lys Pro
 45                  50                  55                  60

GGA AAA GCT CCT AAG CTC CTG ATC TAT GCT GCA TCA AAC TTA GCA GAT            243
Gly Lys Ala Pro Lys Leu Leu Ile Tyr Ala Ala Ser Asn Leu Ala Asp
                 65                  70                  75

GGT GTG CCA TCT AGA TTC AGT GGC AGT GGA TCA GGC ACA GAC TTT ACC            291
Gly Val Pro Ser Arg Phe Ser Gly Ser Gly Ser Gly Thr Asp Phe Thr
     80                  85                  90

CTA ACT ATC TCC AGC CTG CAG CCA GAA GAT TTT GCT ACT TAT TAC TGT            339
Leu Thr Ile Ser Ser Leu Gln Pro Glu Asp Phe Ala Thr Tyr Tyr Cys
         95                 100                 105

CAA CAT TTT TGG ACT ACT CCG TGG GCG TTC GGT CAA GGC ACC AAA GTG            387
Gln His Phe Trp Thr Thr Pro Trp Ala Phe Gly Gln Gly Thr Lys Val
    110                 115                 120

GAA ATC AAA CGT                                                            399
Glu Ile Lys Arg
125

(2) INFORMATION FOR SEQ ID NO:80:

(i) SEQUENCE CHARACTERISTICS:
            (A) LENGTH: 128 amino acids
            (B) TYPE: amino acid
            (D) TOPOLOGY: linear (ii) MOLECULE TYPE: protein (xi) SEQUENCE DESCRIPTION: SEQ ID NO:80:

Met Ser Val Pro Thr Gln Val Leu Gly Leu Leu Leu Trp Leu Thr
 1               5                  10                  15

Asp Ala Arg Cys Asp Ile Gln Met Thr Gln Ser Pro Ser Ser Leu Ser
                 20                  25                  30

Ala Ser Val Gly Asp Arg Val Thr Ile Thr Cys Arg Ala Ser Glu Asn
         35                  40                  45

Ile Tyr Ser Asn Leu Ala Trp Tyr Gln Gln Lys Pro Gly Lys Ala Pro
     50                  55                  60

Lys Leu Leu Ile Tyr Ala Ala Ser Asn Leu Ala Asp Gly Val Pro Ser
 65                  70                  75                  80

Arg Phe Ser Gly Ser Gly Ser Gly Thr Asp Phe Thr Leu Thr Ile Ser

```
                            85                  90                  95
Ser Leu Gln Pro Glu Asp Phe Ala Thr Tyr Tyr Cys Gln His Phe Trp
                100                 105                 110

Thr Thr Pro Trp Ala Phe Gly Gln Gly Thr Lys Val Glu Ile Lys Arg
        115                 120                 125
```

(2) INFORMATION FOR SEQ ID NO:81:

(i) SEQUENCE CHARACTERISTICS:
        (A) LENGTH: 435 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 16..435

(xi) SEQUENCE DESCRIPTION: SEQ ID NO:81:

```
AAGCTTGCCG CCACC ATG GAG TGG TCT TGG GTG TTC CTG TTC TTC CTG TCT        51
                Met Glu Trp Ser Trp Val Phe Leu Phe Phe Leu Ser
                 1               5                  10

GTG ACA ACA GGA GTG CAC TCT CAG GTG CAG CTG GTG CAG TCT GGA GCA         99
Val Thr Thr Gly Val His Ser Gln Val Gln Leu Val Gln Ser Gly Ala
            15                  20                  25

GAG GTG AAG AAG CCT GGA GCA TCT GTG AAG GTG TCT TGT AAG GCA TCT        147
Glu Val Lys Lys Pro Gly Ala Ser Val Lys Val Ser Cys Lys Ala Ser
         30                  35                  40

GGA TTC ACA TTC ACA AAT TAC GGA ATG AAT TGG GTG AGA CAG GCA CCT        195
Gly Phe Thr Phe Thr Asn Tyr Gly Met Asn Trp Val Arg Gln Ala Pro
 45                  50                  55                  60

GGA CAG GGA CTC GAG TGG ATG GGA TGG ATT AAT ACA TAC ACA AGA GAG        243
Gly Gln Gly Leu Glu Trp Met Gly Trp Ile Asn Thr Tyr Thr Arg Glu
                 65                  70                  75

CCT ACG TAC GCA GAC GAC TTC AAG GGA AGA TTC ACA TTC ACA CTG GAG        291
Pro Thr Tyr Ala Asp Asp Phe Lys Gly Arg Phe Thr Phe Thr Leu Glu
             80                  85                  90

ACA TCT GCA TCT ACA GCA TAC ATG GAG CTG TCT TCT CTG AGA TCT GAG        339
Thr Ser Ala Ser Thr Ala Tyr Met Glu Leu Ser Ser Leu Arg Ser Glu
         95                  100                 105

GAC ACA GCA GTG TAC TAC TGT GCA AGA GAC ATT ACA GCA GTG GTA CCT        387
Asp Thr Ala Val Tyr Tyr Cys Ala Arg Asp Ile Thr Ala Val Val Pro
110                 115                 120

ACA GGA TTC GAC TAC TGG GGA CAG GGA ACA CTG GTG ACA GTG TCT TCT        435
Thr Gly Phe Asp Tyr Trp Gly Gln Gly Thr Leu Val Thr Val Ser Ser
125                 130                 135                 140
```

(2) INFORMATION FOR SEQ ID NO:82:

(i) SEQUENCE CHARACTERISTICS:
        (A) LENGTH: 140 amino acids
        (B) TYPE: amino acid
        (D) TOPOLOGY: linear (ii) MOLECULE TYPE: protein (xi) SEQUENCE DESCRIPTION: SEQ ID NO:82:

```
Met Glu Trp Ser Trp Val Phe Leu Phe Phe Leu Ser Val Thr Thr Gly
 1               5                  10                  15

Val His Ser Gln Val Gln Leu Val Gln Ser Gly Ala Glu Val Lys Lys
            20                  25                  30
```

```
Pro Gly Ala Ser Val Lys Val Ser Cys Lys Ala Ser Gly Phe Thr Phe
            35                  40                  45

Thr Asn Tyr Gly Met Asn Trp Val Arg Gln Ala Pro Gly Gln Gly Leu
 50                  55                  60

Glu Trp Met Gly Trp Ile Asn Thr Tyr Thr Arg Glu Pro Thr Tyr Ala
 65                  70                  75                  80

Asp Asp Phe Lys Gly Arg Phe Thr Phe Thr Leu Glu Thr Ser Ala Ser
                85                  90                  95

Thr Ala Tyr Met Glu Leu Ser Ser Leu Arg Ser Glu Asp Thr Ala Val
             100                 105                 110

Tyr Tyr Cys Ala Arg Asp Ile Thr Ala Val Val Pro Thr Gly Phe Asp
            115                 120                 125

Tyr Trp Gly Gln Gly Thr Leu Val Thr Val Ser Ser
130                 135                 140
```

(2) INFORMATION FOR SEQ ID NO:83:

(i) SEQUENCE CHARACTERISTICS:
        (A) LENGTH: 446 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 86..130

(ix) FEATURE:
        (A) NAME/KEY: CDS
        (B) LOCATION: 249..446

(xi) SEQUENCE DESCRIPTION: SEQ ID NO:83:

```
ACCCCAAAGG CCAAACTCTC CACTCCCTCA GCTCGGACAC CTTCTCTCCT CCCAGATCTG      60

AGTAACTCCC AATCTTCTCT CTGCA GAG CCC AAA TCT TGT GAC AAA ACT CAC      112
                           Glu Pro Lys Ser Cys Asp Lys Thr His
                            1               5

ACA TGC CCA CCG TGC CCA GGTAAGCCAG CCCAGGCCTC GCCCTCCAGC              160
Thr Cys Pro Pro Cys Pro
 10              15

TCAAGGCGGG ACAGGTGCCC TAGAGTAGCC TGCATCCAGG GACAGGCCCC AGCCGGGTGC     220

TGACACGTCC ACCTCCATCT CTTCCTCA GCA CCT GAA CTC CTG GGG GGA CCG       272
                                Ala Pro Glu Leu Leu Gly Gly Pro
                                 1               5

TCA GTC TTC CTC TTC CCC CCA AAA CCC AAG GAC ACC CTC ATG ATC TCC      320
Ser Val Phe Leu Phe Pro Pro Lys Pro Lys Asp Thr Leu Met Ile Ser
 10                  15                  20

CGG ACC CCT GAG GTC ACA TGC GTG GTG GTG GAC GTG AGC CAC GAA GAC      368
Arg Thr Pro Glu Val Thr Cys Val Val Val Asp Val Ser His Glu Asp
 25                  30                  35                  40

CCT GAG GTC AAG TTC AAC TGG TAC GTG GAC GGC GTG GAG GTG CAT AAT      416
Pro Glu Val Lys Phe Asn Trp Tyr Val Asp Gly Val Glu Val His Asn
                 45                  50                  55

GCC AAG ACA AAG CCG CGG GAG GAG CAG TAC                              446
Ala Lys Thr Lys Pro Arg Glu Glu Gln Tyr
             60                  65
```

(2) INFORMATION FOR SEQ ID NO:84:

(i) SEQUENCE CHARACTERISTICS:
        (A) LENGTH: 15 amino acids (B) TYPE: amino acid
            (D) TOPOLOGY: linear (ii) MOLECULE TYPE: protein (xi) SEQUENCE DESCRIPTION: SEQ ID NO:84:

Glu Pro Lys Ser Cys Asp Lys Thr His Thr Cys Pro Pro Cys Pro
 1               5                  10                  15

(2) INFORMATION FOR SEQ ID NO:85:

(i) SEQUENCE CHARACTERISTICS:
        (A) LENGTH: 66 amino acids
        (B) TYPE: amino acid
        (D) TOPOLOGY: linear (ii) MOLECULE TYPE: protein (xi) SEQUENCE DESCRIPTION: SEQ ID NO:85:

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr
 65

(2) INFORMATION FOR SEQ ID NO:86:

(i) SEQUENCE CHARACTERISTICS:
        (A) LENGTH: 129 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 16..129

(xi) SEQUENCE DESCRIPTION: SEQ ID NO:86:

TTCGAAGCCG CCACC ATG TGG GGA TCT GTT TTC CAT TTT TCA ATT GTA GAT        51
              Met Trp Gly Ser Val Phe His Phe Ser Ile Val Asp
               1               5                  10

GCC AGA TGT GAC ATC CAG ATG ACT CAG TCT CCA GCC TCC CTA TCT GTA         99
Ala Arg Cys Asp Ile Gln Met Thr Gln Ser Pro Ala Ser Leu Ser Val
         15                  20                  25

TCT GTG GGA GAA ACT GTC ACC ATC ACA TGT                                129
Ser Val Gly Glu Thr Val Thr Ile Thr Cys
         30                  35

(2) INFORMATION FOR SEQ ID NO:87:

(i) SEQUENCE CHARACTERISTICS:
        (A) LENGTH: 38 amino acids
        (B) TYPE: amino acid
        (D) TOPOLOGY: linear (ii) MOLECULE TYPE: protein (xi) SEQUENCE DESCRIPTION: SEQ ID NO:87:

Met Trp Gly Ser Val Phe His Phe Ser Ile Val Asp Ala Arg Cys Asp

```
             1               5              10              15
Ile Gln Met Thr Gln Ser Pro Ala Ser Leu Ser Val Ser Val Gly Glu
                    20              25              30

Thr Val Thr Ile Thr Cys
            35

(2) INFORMATION FOR SEQ ID NO:88:

(i) SEQUENCE CHARACTERISTICS:
        (A) LENGTH: 144 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 16..144

(xi) SEQUENCE DESCRIPTION: SEQ ID NO:88:

TTCGAAGCCG CCACC ATG AGG TGC TCT GCT GAG TTT CTG GGG TTG CTG CTG      51
                Met Arg Cys Ser Ala Glu Phe Leu Gly Leu Leu Leu
                 1               5                      10

CTG TGG CTT ACA GAT GCC AGA TGT GAC ATC CAG ATG ACT CAG TCT CCA       99
Leu Trp Leu Thr Asp Ala Arg Cys Asp Ile Gln Met Thr Gln Ser Pro
             15                  20                  25

GCC TCC CTA TCT GTA TCT GTG GGA GAA ACT GTC ACC ATC ACA TGT          144
Ala Ser Leu Ser Val Ser Val Gly Glu Thr Val Thr Ile Thr Cys
     30                  35                  40

(2) INFORMATION FOR SEQ ID NO:89:

(i) SEQUENCE CHARACTERISTICS:
        (A) LENGTH: 43 amino acids
        (B) TYPE: amino acid
        (D) TOPOLOGY: linear (ii) MOLECULE TYPE: protein (xi) SEQUENCE DESCRIPTION: SEQ ID NO:89:

Met Arg Cys Ser Ala Glu Phe Leu Gly Leu Leu Leu Trp Leu Thr
 1               5                  10                  15

Asp Ala Arg Cys Asp Ile Gln Met Thr Gln Ser Pro Ala Ser Leu Ser
             20                  25                  30

Val Ser Val Gly Glu Thr Val Thr Ile Thr Cys
         35                  40

(2) INFORMATION FOR SEQ ID NO:90:

(i) SEQUENCE CHARACTERISTICS:
        (A) LENGTH: 168 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 16..168

(xi) SEQUENCE DESCRIPTION: SEQ ID NO:90:

TTCGAAGCCG CCACC ATG GGC ATC AAG ATG GAG TCA CAG TTC CAG GTC TTC      51
                Met Gly Ile Lys Met Glu Ser Gln Phe Gln Val Phe
                 1               5                      10
```

```
ATA TCC ATA CTG CTC TGG TTA TAT GGA GCT GAT GGG AAC ATT GTA ATG    99
Ile Ser Ile Leu Leu Trp Leu Tyr Gly Ala Asp Gly Asn Ile Val Met
        15                  20                  25

ACC CAA TCT CCC AAA TCC ATG TCC ATG TCA GTA GGA GAG AGG GTC ACC   147
Thr Gln Ser Pro Lys Ser Met Ser Met Ser Val Gly Glu Arg Val Thr
    30                  35                  40

TTG ACC TGC AAG GCC AGT GAG                                       168
Leu Thr Cys Lys Ala Ser Glu
45                  50
```

(2) INFORMATION FOR SEQ ID NO:91:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO:91:

```
Met Gly Ile Lys Met Glu Ser Gln Phe Gln Val Phe Ile Ser Ile Leu
1               5                   10                  15

Leu Trp Leu Tyr Gly Ala Asp Gly Asn Ile Val Met Thr Gln Ser Pro
            20                  25                  30

Lys Ser Met Ser Met Ser Val Gly Glu Arg Val Thr Leu Thr Cys Lys
        35                  40                  45

Ala Ser Glu
    50
```

(2) INFORMATION FOR SEQ ID NO:92:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:92:

```
Asp Ile Gln Met Trp Gln Ser Phe Ala Ser
1               5                   10
```

(2) INFORMATION FOR SEQ ID NO:93:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:93:

```
GCCGCCACC                                                           9
```

(2) INFORMATION FOR SEQ ID NO:94:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:94:

```
                                                          -continued

GCGCGCAAGC TTGCCGCCAC C                                                     21

(2) INFORMATION FOR SEQ ID NO:95:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:95:

GGACTGTTCG AAGCCGCCAC C                                                     21
```

US 6,180,377 B1

HUMANIZED ANTIBODIES

REFERENCE TO RELATED APPLICATIONS

This application is a national phase of International Application No. PCT/GB94/01291, filed Jun. 15, 1994, which claims priority to GB 9312415.4, filed Jun. 16, 1993, GB 9401597.1, filed Jan. 27, 1994, GB 9402499.9, filed Feb. 9, 1994 and GB 9406222.1, filed Mar. 29, 1994.

FIELD OF THE INVENTION

This invention relates to humanised antibodies, having specificity for the epitope recognised by the murine monoclonal antibody L243, to processes for preparing said antibodies, to pharmaceutical compositions containing said antibodies, and to medical uses of said antibodies.

The term humanised antibody molecule is used to describe a molecule having an antigen binding site derived from an immunoglobulin from a non-human species, the remaining immunoglobulin-derived parts of the molecule being derived from a human immunoglobulin. The antigen binding site may comprise either complete variable regions fused onto human constant domains or only the complementarity determining regions (CDRs) grafted onto appropriate human framework regions in the variable domains.

BACKGROUND OF THE INVENTION

The proteins encoded in the Major Histocompatibility Complex region of the genome are involved in many aspects of immunological recognition. It is known that all mammals and probably all vertebrates possess basically equivalent MHC systems and that immune response genes are linked to the MHC.

In man the major histocompatibility complex is the HLA gene cluster on chromosome 6. The main regions are D, B, C, and A. The D region contains genes for Class II proteins which are involved in cooperation and interaction between cells of the immune system. Many diseases have been found to be associated with the D region of the HLA gene cluster. Studies to date have shown associations with an enormous variety of diseases including most autoimmune diseases (see for example European Patent No. 68790). European Patent No. 68790 suggests controlling diseases associated with a particular allele of certain regions of the MHC such as the HLA-D region in humans by selectively suppressing the immune response(s) controlled by a monoclonal antibody specific for an MHC-Class II antigen.

L243 is a murine IgG2A anti-HLA DR antibody which we believe to be of particular use in treatment of diseases such as autoimmune diseases since it shows particularly potent suppression of in vitro immune function and is monomorphic for all HLA-DR.

Since most available monoclonal antibodies are of rodent origin, they are naturally antigenic in humans and thus can give rise to an undesirable immune response termed the HAMA (Human Anti-Mouse Antibody) response. Therefore, the use of rodent monoclonal antibodies as therapeutic agents in humans is inherently limited by the fact that the human subject will mount an immunological response to the antibody and will either remove it entirely or at least reduce its effectiveness.

Proposals have been made for making non-human MAbs less antigenic in humans. Such techniques can be generically termed 'humanisation' techniques. These techniques generally involve the use of recombinant DNA technology to manipulate DNA sequences encoding the polypeptide chains of the antibody molecule. A simple form of humanisation involves the replacement of the constant regions of the murine antibody with those from a human antibody [Morrison et al (1984) Proc. Natl. Acad. Sci. USA 81 6851–55; Whittle et al (1987) Prot. Eng. 1 499–505]. The lowering of the level of the HAMA response to the chimeric antibodies leads to the expectation that further humanisation of the variable region outside of the antigen binding site may abolish the response to these regions and further reduce any adverse response.

A more complex form of humanisation of an antibody involves the redesign of the variable region domain so that the amino acids constituting the murine antibody binding site are integrated into the framework of a human antibody variable region. Humanisation has led to the reconstitution of full antigen binding activity in a number of cases [Co et al (1990) J. Immunol. 148 1149–1154; Co et al (1992) Proc. Natl. Acad. Sci. USA 88 2869–2873; Carter et al (1992) Proc. Natl. Acad. Sci. 89 4285–4289; Routledge et al (1991) Eur. J. Immunol. 21 2717–2725 and International Patent Specifications Nos. WO 91/09967; WO 91/09968 and WO 92/113831.

It can therefore be anticipated that the humanisation of L243 may lead to reduced immunogenicity in man and overcome the potential problem of the HAMA response previously associated with the use of murine antibodies in humans.

We have now prepared recombinant antibody molecules having specificity for the epitope recognised by the murine monoclonal antibody L243.

SUMMARY OF THE INVENTION

Thus according to a first aspect the invention provides a recombinant antibody molecule having specificity for antigenic determinants dependent on the DRα chain.

The term recombinant antibody molecule is used to denote an antibody produced using recombinant DNA techniques. The antibody is preferably a humanised antibody, e.g. a chimeric or CDR-grafted antibody.

In a preferred embodiment of the first aspect the invention provides a recombinant antibody molecule have specificity for the epitope recognised by the murine monoclonal antibody L243.

In a preferred embodiment of the first aspect of the present invention there is provided a humanised antibody molecule having specificity for the epitope recognised by the murine monoclonal antibody L243 and having an antigen binding site wherein at least one of the complementarity determining regions (CDRs) of the variable domain is derived from the mouse monoclonal antibody L243 (MAb L243) and the remaining immunoglobulin-derived parts of the humanised antibody molecule are derived from a human immunoglobulin or an analogue thereof, said humanised antibody molecule being optionally conjugated to an effector or reporter molecule.

The humanised antibody molecule may comprise a chimeric humanised antibody or a CDR-grafted humanised antibody. When the humanised antibody molecule comprises a CDR-grafted humanised antibody, the heavy and/or light chain variable domains may comprise only one or two MAb L243 derived CDRs; though preferably all three heavy and light chain CDRs are derived from MAb L243.

As described above L243 is a monoclonal antibody previously described by Lampson & Levy [J. Immunol. (1980) 125 293]. The amino acid sequences of the light and heavy chain variable regions of the antibody are shown in FIGS. 1 and 2 hereinafter. L243 has been deposited at the American Type Culture Collection, Rockville, Md. USA under Accession number ATCC HB55.

DETAILED DESCRIPTION OF THE INVENTION

The humanised antibody of the present invention may have attached to it an effector or reporter molecule. For instance a macrocycle for chelating a heavy metal atom, or a toxin such as ricin, may be attached to the humanised antibody by a covalent bridging structure. Alternatively, the procedure of recombinant DNA technology may be used to produce a humanised antibody molecule in which the Fc fragment, $C_H3$ or $C_H2$ domain of a complete antibody molecule has been replaced by or has attached thereto by peptide linkage a functional non-immunoglobulin protein such as an enzyme or toxin molecule.

The humanised antibody of the present invention may comprise a complete antibody molecule, having full length heavy and light chains; a fragment thereof, such as a Fab, Fab', (Fab')$_2$, or Fv fragment; a single chain antibody fragment, e.g. a single chain Fv, a light chain or heavy chain monomer or dimer; multivalent monospecific antigen binding proteins comprising two, three, four or more antibodies or fragments thereof bound to each other by a connecting structure; or a fragment or analogue of any of these or any other molecule with the same specificity as MAb L243.

In a preferred embodiment the antibody comprises a complete antibody molecule, having full length heavy and light chains.

The remaining non-L243 immunoglobulin derived parts of the humanised antibody molecule may be derived from any suitable human immunoglobulin. For instance where the humanised antibody molecule is a CDR-grafted humanised antibody molecule, appropriate variable region framework sequences may be used having regard to class/type of the donor antibody from which the antigen binding regions are derived. Preferably the type of human framework used is of the same/similar class/type as the donor antibody. Advantageously the framework is chosen to maximise/optimise homology with the donor antibody sequence particularly at positions spacially close or adjacent to the CDRS. Examples of human frameworks which may be used to construct CDR-grafted antibodies are LAY, POM, TUR, TEI, KOL, NEWM, REI and EU; for instance KOL and NEWM for the heavy chain and REI for the light chain or EU for both the heavy chain and light chain.

An alternative procedure for the selection of a suitable human framework involves aligning the framework regions of the light chain of the non-human framework with those of the four human light chain subgroups identified by Kabat et al (1991) [in: Sequences of Proteins of Immunological Interest, Fifth Edition]. The consensus sequence for the light chain subgroup most homologous to the non-human antibody light chain is chosen.

Any differences between the framework residues of the non-human antibody and the consensus human group light chain sequence are analysed for the potential contribution they may have to antigen binding as described in Published International Patent Application No. WO91/09967. Based on this analysis some or all of the residues identified may be altered. The same procedure is carried out for the selection of a suitable framework to accept the non-human heavy chain CDRs.

For constructing the L243 CDR grafted light chain, the human subgroup 1 consensus sequence was found to be particularly suitable, and for constructing the L243 grafted heavy chain the human subgroup 1 consensus sequence was also found to be particularly suitable.

The light or heavy chain variable domains of the humanised antibody molecule may be fused to human light or heavy chain constant domains as appropriate, (the term 'heavy chain constant domains' as used herein are to be understood to include hinge regions unless specified otherwise). The human constant domains of the humanised antibody molecule, where present, may be selected having regard to the proposed function of the antibody, in particular the lack of effector functions which may be required. For example, the heavy chain constant domains fused to the heavy chain variable region may be human IgA, IgG or IgM domains. Preferably human IgG domains are used. Light chain human constant domains which may be fused to the light chain variable region include human Lambda or human Kappa chains.

Analogues of human constant domains may alternatively be advantageously used. These include those constant domains containing one or more additional amino acids than the corresponding human domain or those constant domains wherein one or more existing amino acids of the corresponding human domain has been deleted or altered. Such domains may be obtained, for example, by oligonucleotide directed mutagenesis.

The remainder of the humanised antibody molecule need not comprise only protein sequences from human immunoglobulins. For instance, a gene may be constructed in which a DNA sequence encoding part of a human immunoglobulin chain is fused to a DNA sequence encoding the amino acid sequence of a polypeptide effector or reporter molecule.

We have found that by modifying one or more residues in the N-terminal region of the $C_H2$ domain of the L243 antibody we produce an antibody with an altered ability to fix complement as compared to unaltered antibody.

The amino acid residue which is altered preferably lies within amino acid positions 231 to 239, preferably within amino acid positions 234 and 239.

In a particularly preferred embodiment the amino acid residue which is altered is either Leu 235 and/or Gly 237.

As used herein the term 'altered' when used in conjunction with the ability of an antibody to fix complement most usually indicates a decrease in the ability of antibody to fix complement compared to the starting unaltered antibody. By choosing an appropriate amino acid to alter it is possible to produce an antibody the ability of which to fix complement is substantially reduced such as for example by altering residue Leu 235. It is also possible to produce an antibody with an intermediate ability to fix complement as compared to unaltered antibody by for example altering amino acid residue Gly 237.

As used herein the phrase 'substantially' reduce complement fixation denotes that human complement fixation is preferably $\leq 30\%$, more preferably $\leq 20\%$ and is most preferably $\leq 10\%$ of the level seen with wild type antibody.

Due to the alteration of one or more amino acid residues in the N-terminal region of the $C_H2$ domain the antibody will preferably not bind significantly to FcRI and will bind to FcRIII receptor.

The residue numbering used herein is according to the Eu index described in Kabat et al [(1991) in: Sequences of Proteins of Immunological Interest, 5th Edition, United States Department of Health and Human Services].

The alterations at position 235 of replacing leucine by glutamic acid or alanine have been found particularly effective at producing a potent immunosuppressive L243 antibody with minimal toxicity in vitro.

The alteration at position 237 of replacing glycine by alanine has been found to produce an antibody with an intermediate ability to fix complement i.e. the complement fixation level is approximately 15–80%, preferably 20–60% most preferably 20–40% of that seen with the wild type antibody.

The residue(s) could similarly be replaced using an analogous process to that described herein, by any other amino acid residue or amino acid derivative, having for example an inappropriate functionality on its side chain. This may be achieved by for example changing the charge and/or polarity of the side chain.

The term 'significantly' as used with respect to FcRI binding denotes that the binding of antibody to FcRI is typically $\leq 20\%$, and is most preferably >10% of that seen with unaltered antibody.

The standard techniques of molecular biology may be used to prepare DNA sequences coding for the antibodies according to the invention. Desired DNA sequences may be synthesised completely or in part using oligonucleotide synthesis techniques. Site-directed mutagenesis and polymerase chain reaction (PCR) techniques may be used as appropriate.

Suitable processes include the PCR strand overlap procedure and PCR mutagenesis as described in for example "PCR Technology Principles and Applications for DNA Amplification" (1989), Ed. H. A. Erlich, Stockholm Press, N.Y., London, and oligonucleotide directed mutagenesis [Kramer et al, Nucleic. Acid. Res. 12 9441 (1984)]. Suitable techniques are also disclosed in Published European Patent No. EP307434B.

The altered L243 with altered complement fixing ability may also be produced by for example, deleting residues such as 235, or by for example, inserting a glycosylation site at a suitable position in the molecule. Such techniques are well known in the art, see for example the teaching of published European patent application EP-307434.

The altered L243 may also be produced by exchanging lower hinge regions of antibodies of different isotypes. For example a G1/G2 lower hinge exchange abolished complement fixation.

The G1/G2 lower hinge exchange results in an antibody with altered residues in the 231–238 region of the N-terminal region of the $C_H2$ domain, wherein one or more residues may be altered or deleted.

According to a second aspect of the invention there is provided a process for producing the humanised antibody of the first aspect of the invention which process comprises:
a) producing in an expression vector an operon having a DNA sequence which encodes an antibody heavy or light chain comprising a variable domain wherein at least one of the CDRs of the variable domain is derived from the L243 MAb and the remaining immunoglobulin-derived parts of the antibody chain are derived from a human immunoglobulin;
b) producing in an expression vector an operon having a DNA sequence which encodes a complementary antibody light or heavy chain comprising a variable domain wherein at least one of the CDRs of the variable domain is derived from the MAb L243 and the remaining immunoglobulin-derived parts of the antibody chain are derived from a human immunoglobulin;
c) transfecting a host cell with both operons; and
d) culturing the transfectec cell line to produce the humanised antibody molecule.

In a preferred embodiment of this aspect of the invention at least one of the expression vectors contains a DNA sequence encoding an antibody heavy chain in which one or more amino acid residues the N-terminal region of the $C_H2$ domain of said antibody has been altered from that in the corresponding unaltered antibody.

The alteration in the N-terminal region of the $C_H2$ domain may be made after the whole unmodified antibody has been expressed using techniques such as site directed mutagenesis.

The cell line may be transfected with two vectors, the first vector containing the operon encoding the light chain-derived polypeptide and the second vector containing the operon encoding the heavy chain derived polypeptide. Preferably the vectors are identical except in so far as the coding sequences and selectable markers are concerned so as to ensure as far as possible that each polypeptide chain is equally expressed.

Alternatively, a single vector may be used, the vector including the operons encoding both light chain- and heavy chain-derived polypeptides, and a selectable marker.

The alteration in the N-terminal region of the $C_H2$ domain, e.g. at position 235 of the $C_H2$ domain of the molecule may be introduced at any convenient stage in the humanisation e.g. CDR-grafting process. It is conveniently introduced after the variable domains have been grafted onto the heavy chains.

In further aspects, the invention also includes DNA sequences coding for the heavy and light chains of the antibodies of the present invention, cloning and expression vectors containing these DNA sequences, host cells transformed with these DNA sequences and processes for producing the heavy or light chains and antibody molecules comprising expressing these DNA sequences in a transformed host cell.

The general methods by which the vectors may be constructed, transfection methods and culture methods are well known per se [see for example Maniatis et al (1982) (Molecular Cloning, Cold Spring Harbor, New York) and Primrose and Old (1980) (Principles of Gene Manipulation, Blackwell, Oxford) and the examples hereinafter].

The DNA sequences which encode the L243 light and heavy chain variable domain amino acid sequences (and the corresponding deduced amino acid sequences) are given hereafter in FIGS. 1 and 2 respectively.

DNA coding for human immunoglobulin sequences may be obtained in any appropriate way. For example, amino acid sequences of preferred human acceptor frameworks such as, LAY, POM, KOL, REI, EU, TUR, TEI and NEWM are widely available to workers in the art. Similarly the consensus sequences for human light and heavy chain subgroups are available to workers in the art.

The standard techniques of molecular biology may be used to prepare DNA sequences coding for CDR-grafted products. Desired DNA sequences may be synthesised completely or in part using oligonucleotide synthesis techniques. Site-directed mutagenesis and polymerase chain reaction (PCR) techniques may be used as appropriate. For example, oligonucleotide directed synthesis [Jones et al (1986) Nature 321 522–525] and also oligonucleotide directed mutagenesis of a pre-existing variable domain region [Verhoeyen et al (1988) Science 23 1534–1536; Reichmann et al (1988) Nature =323–327].

Enzymatic filling-in of gapped oligonucleotides using T4 DNA polymerase [Queen et al (1989) Proc. Natl. Acad. Sci. USA 86 10029–10033; International Patent Application No. WO 90/07861] may be used.

Any suitable host cell/vector system may be used for expression of the DNA sequences coding for the chimeric or CDR-grafted heavy and light chains. Bacterial e.g. *E. coli* and other microbial systems may be used advantageously in particular for expression of antibody fragments, e.g. Fv, Fab and Fab' fragment and single chain antibody fragments e.g. single chain Fvs. Eucaryotic e.g. mammalian host cell expression systems may also be used to obtain antibodies according to the invention, particularly for production of larger chimeric or CDR-grafted antibody products. Suitable mammalian host cells include COS cells and CHO cells [Bebbington C R (1991) Methods 2 136–145] and myeloma or hybridoma cell lines, for example NSO cells (Bebbington C R et al (1992) BiofTechnology 10 169–175]. The use of CHO cells is especially preferred.

In the humanised antibody according to the invention, the heavy and light chain variable domains may comprise either the entire variable domains of MAb L243, or may comprise framework regions of a human variable domain having grafted thereon one, some or all of the CDRs of MAb L243. Thus the humanised antibody may comprise a chimeric humanised antibody or a CDR-grafted humanised antibody.

When the humanised antibody is a CDR-grafted humanised antibody, in addition to the CDRs, specific variable region framework residues may be altered to correspond to non-human i.e. L243 mouse residues. Preferably the CDR-grafted humanised antibodies of the present invention include CDR-grafted humanised antibodies as defined in our International Patent Specification No. WO-A-91/09967. The disclosure of WO-A-91/09967 is incorporated herein by reference.

Preferably the CDRs of the heavy chain correspond to the L243 residues at all of CDR1 (31 to 35), CDR2 (50 to 65) and CDR3 (95 to 102). Preferably the CDRs of the light chain correspond to L243 residues at all of CDR1 (24 to 34) CDR2 (50 to 56) and CDR3 (89 to 97). In addition the heavy chain may have mouse L243 residues at one or more of residues 27, 67, 69, 71, 72 and 75. Similarly the light chain may have mouse L1243 residues at one or more positions 45, 49, 70 and 71.

The invention further provides a CDR-grafted humanised antibody heavy chain having a variable region domain comprising acceptor frameworks derived from human subgroup consensus sequence 1 and L243 donor antigen binding regions wherein the framework comprises L243 donor residues at one or more of positions 27, 67, 69, 71, 72 and 75.

The invention further provides a CDR-grafted humanised antibody light chain having a variable region domain comprising acceptor frameworks derived from human subgroup consensus sequence 1 and L243 donor antigen binding regions wherein the framework comprises L243 donor residues at one or more of positions 45, 49, 70 and 71.

The heavy chain may further have mouse L243 residues at one or more of residues 2, 9, 11, 16, 17, 20, 38, 43, 46, 80, 81, 82, 82a, 82b, 83, 84, 89, 91,108 and 109.

The light chain may further have mouse L243 residues at one or more of residues 9, 13, 17, 18, 37, 40, 43, 45, 48, 49, 72, 74, 76, 80, 84, 85, 100, 103 and 104.

The antibody according to the invention may be a complete antibody or as explained above, a fragment thereof, a monomer or dimer or a multivalent monospecific antigen binding protein. Certain compounds of this latter group are particularly advantageous in that they possess high avidity. See for example Published International Patent Specification No. WO 92/01472 the teaching of which is incorporated herein.

Thus according to a further particular aspect of the invention we provide a multivalent monospecific antigen binding protein comprising two, three, four or more antibodies or fragments thereof bound to each other by a connecting structure which protein is not a natural immunoglobulin, each of said antibodies or fragments having a specificity for the epitope recognised by murine MAb L243 said antigen binding protein being optionally conjugated with an effector or reporter molecule.

In this aspect of the invention each antibody or fragment is preferably a humanised antibody or a fragment thereof as defined above and the multivalent monospecific antigen binding protein is thus a humanised multivalent monospecific antigen binding protein. Non-humanised e.g. murine, multivalent monospecific antigen binding proteins can, however, be contemplated and the invention is to be understood to also extend to these.

The multivalent antigen binding protein, preferably comprises two, three or four antibodies or fragments thereof bound to each other by a connecting structure.

Immunological diseases which may be treated with the antibodies of the invention include for example joint diseases such as ankylosing spondylitis, juvenile rheumatoid arthritis, rheumatoid arthritis; neurological disease such as multiple sclerosis; pancreatic disease such as diabetes, juvenile onset diabetes; gastrointestinal tract disease such as chronic active hepatitis, celiac disease, ulcerative colitis, Crohns disease, pernicious anaemia; skin diseases such as psoriasis; allergic diseases such as asthma and in transplantation related conditions such as graft versus host disease and allograft rejection. Other diseases include those described in European Patent No. 68790.

The present invention also includes therapeutic and diagnostic compositions containing the antibodies of the invention. Such compositions typically comprise an antibody according to the invention together with a pharmaceutically acceptable excipient, diluent or carrier, e.g. for in vivo use.

Thus in a further aspect the invention provides a therapeutic, pharmaceutical or diagnostic composition comprising an antibody according to the invention, in combination with a pharmaceutically acceptable excipient, diluent or carrier.

The invention also provides a process for the preparation of a therapeutic, pharmaceutical or diagnostic composition comprising admixing an antibody according to the invention together with a pharmaceutically acceptable excipient, diluent or carrier.

The antibodies and compositions may be for administration in any appropriate form and amount according to the therapy in which they are employed.

The therapeutic, pharmaceutical or diagnostic composition may take any suitable form for administration, and, preferably is in a form suitable for parenteral administration e.g. by injection or infusion, for example by bolus injection or continuous infusion. Where the product is for injection of infusion, it may take the form of a suspension, solution or emulsion in an oily or aqueous vehicle and it may contain formulatory agents such as suspending, preservative, stabilising and/or dispersing agents.

Alternatively, the antibody or composition may be in dry form, for reconstitution before use with an appropriate sterile liquid.

If the antibody or composition is suitable for oral administration the formulation may contain, in addition to the active ingredient, additives such as: starch e.g. potato, maize or wheat starch or cellulose or starch derivatives such as microcrystalline cellulose; silica; various sugars such as lactose; magnesium carbonate and/or calcium phosphate. It is desirable that, if the oral formulation is for administration it will be well tolerated by the patient's digestive system. To this end, it may be desirable to include in the formulation mucus formers and resins. It may also be desirable to improve tolerance by formulating the antibody or compositions in a capsule which is insoluble in the gastric juices. It may also be preferable to include the antibody or composition in a controlled release formulation.

If the antibody or composition is suitable for rectal administration the formulation may contain a binding and/or lubricating agent; for example polymeric glycols, gelatins, cocoa-butter or other vegetable waxes or fats.

Therapeutic and diagnostic uses typically comprise administering an effective amount of an antibody according to the invention to a human subject. The exact dose to be administered will vary according to the use of the antibody and on the age, sex and condition of the patient but may typically be varied from about 0.1 mg to 1000 mg for example from about 1 mg to 500 mg. The antibody may be administered as a single dose or in a continuous manner over a period of time. Doses may be repeated as appropriate.

The antibodies and compositions may be for administration in any appropriate form and amount according to the therapy in which they are employed. The dose at which the antibody is administered depends on the nature of the condition to be treated and on whether the antibody is being used prophylactically or to treat an existing condition. The dose will also be selected according to the age and conditions of the patient. A therapeutic dose of the antibodies according to the invention may be, for example, between preferably 0.1–25 mg/kg body weight per single therapeutic dose and most preferably between 0.1–10 mg/kg body weight for single therapeutic dose.

The antibody may be formulated in accordance with conventional practice for administration by any suitable route and may generally be in a liquid form (e.g. a solution of the antibody in a sterile physiologically acceptable buffer) for administration by for example an intravenous, intraperitoneal or intramuscular route.

The present invention is now described by way of example only, by reference to the accompanying drawings in which:

FIG. 1: shows the nucleotide SEQ ID NO: 73 and amino acid SEQ ID NO: 74 sequence of L243 Vl region FIG. 2: shows the nucleotide SEQ ID NO: 75 and amino acid SEQ ID NO: 76 sequence of L243 Vh region FIG. 3: shows a diagrammatic map of plasmid pMR15.1

FIG. 4: shows the nucleotide SEQ ID NO: 77 and amino acid SEQ ID NO: 78 sequence of Vl region in L243-gL1

FIG. 5: shows the nucleotide SEQ ID NO: 79 and amino acid SEQ ID NO: 80 sequence of Vl region of L243-gL2

Figure 6:
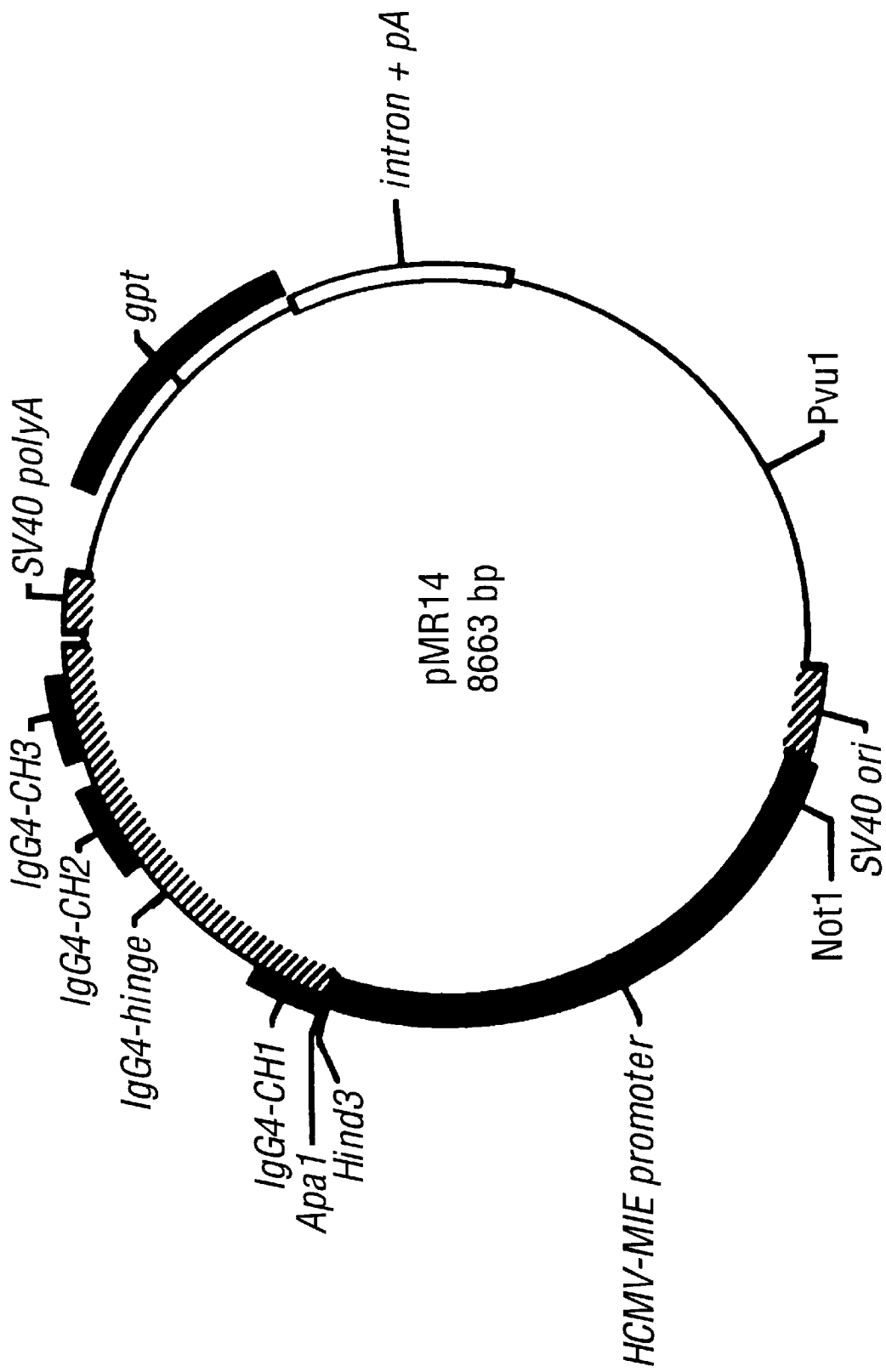

FIG. 6: shows a diagrammatic map of plasmid pMR14.

FIG. 7: shows the nucleotide SEQ ID NO: 81 and amino acid SEQ ID NO: 82 sequence of Vh region of L243-gH.

Figure 8:
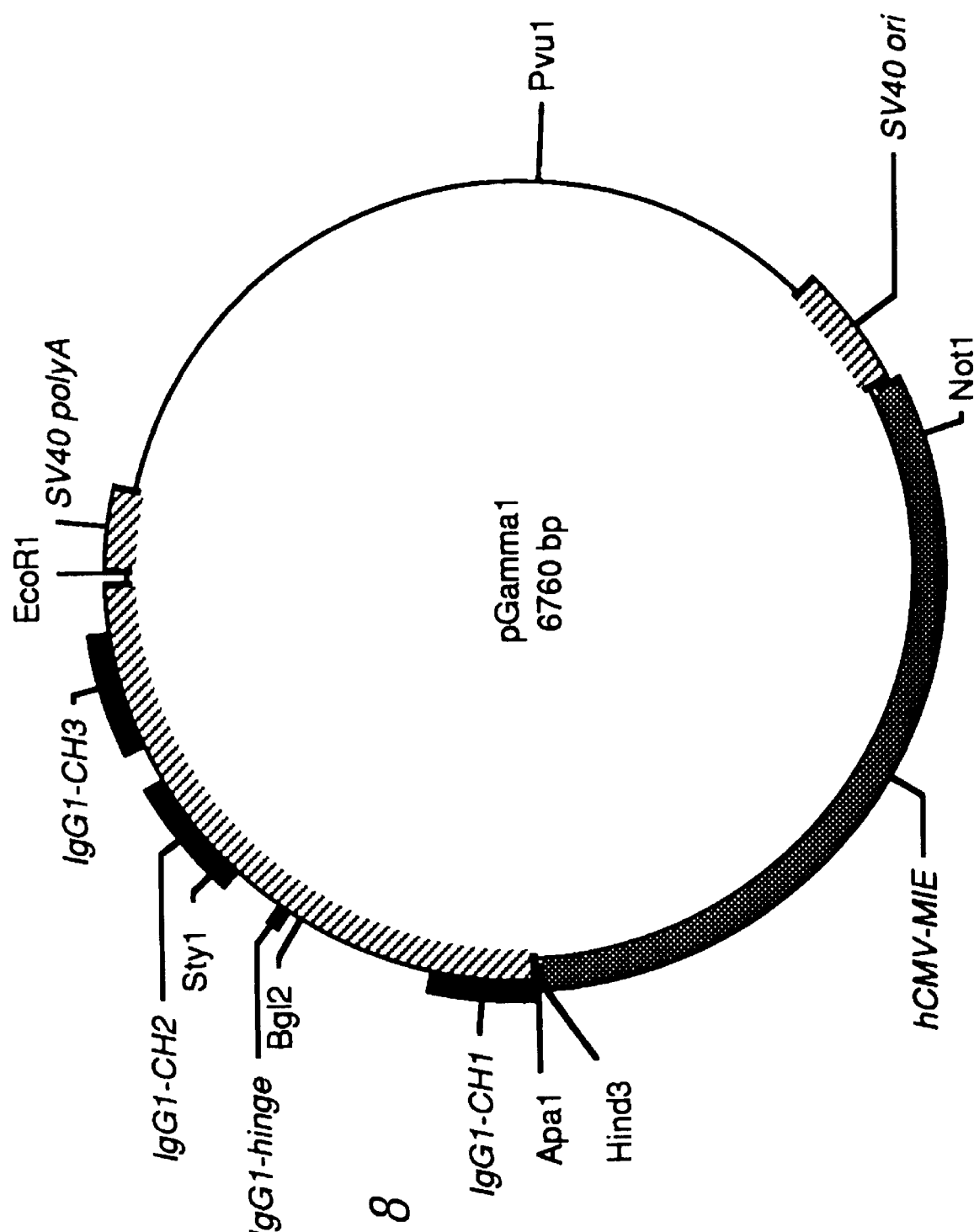

FIG. 8: shows a diagrammatic map of plasmid pGamma 1.

Figure 9:
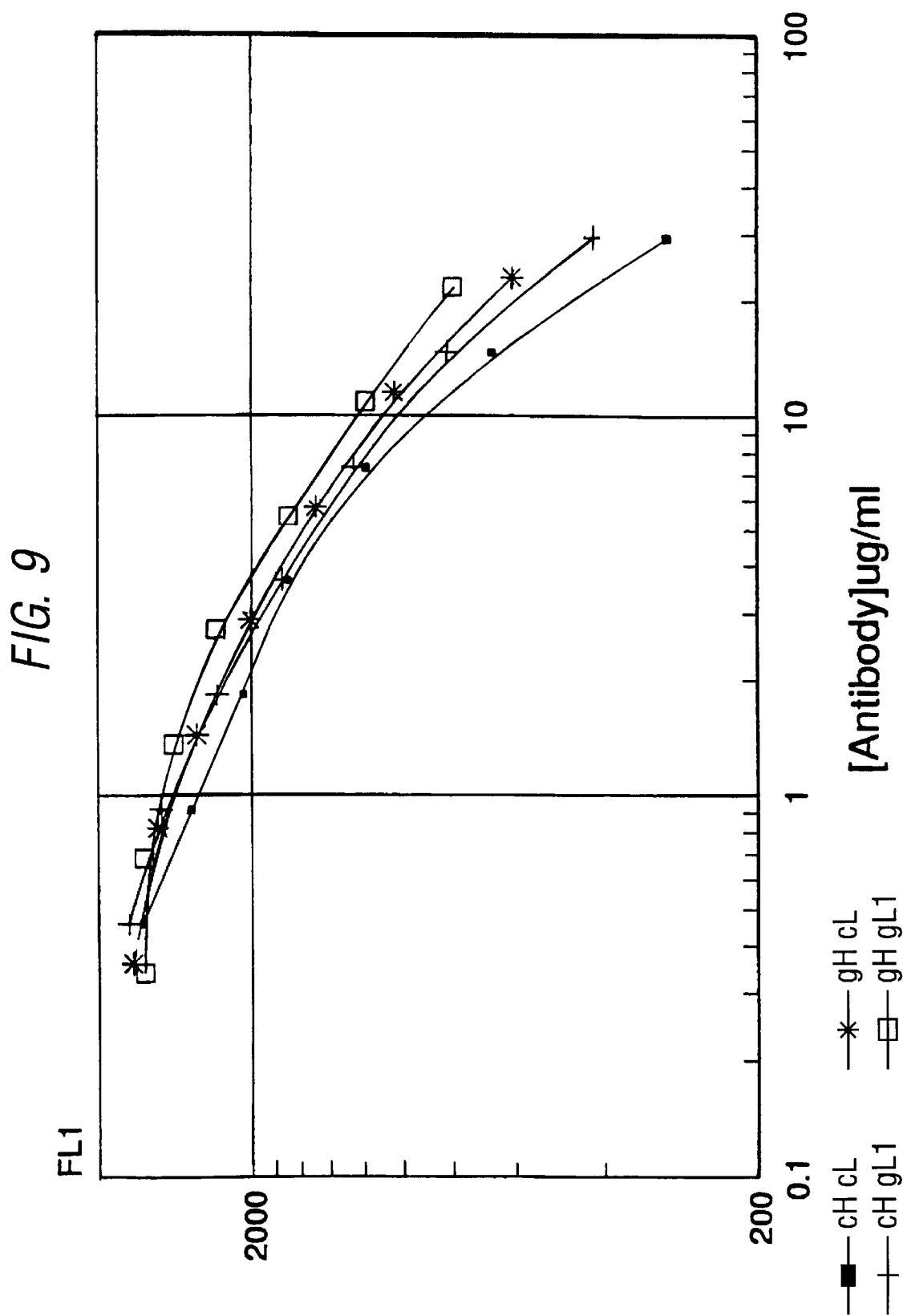

FIG. 9: shows a graph of the results of a competition assay for L243 grafts vs FITC-chimeric L243
- cH cL
+ cH gL1
* gH cL
◦ gH gL1

Figure 10:
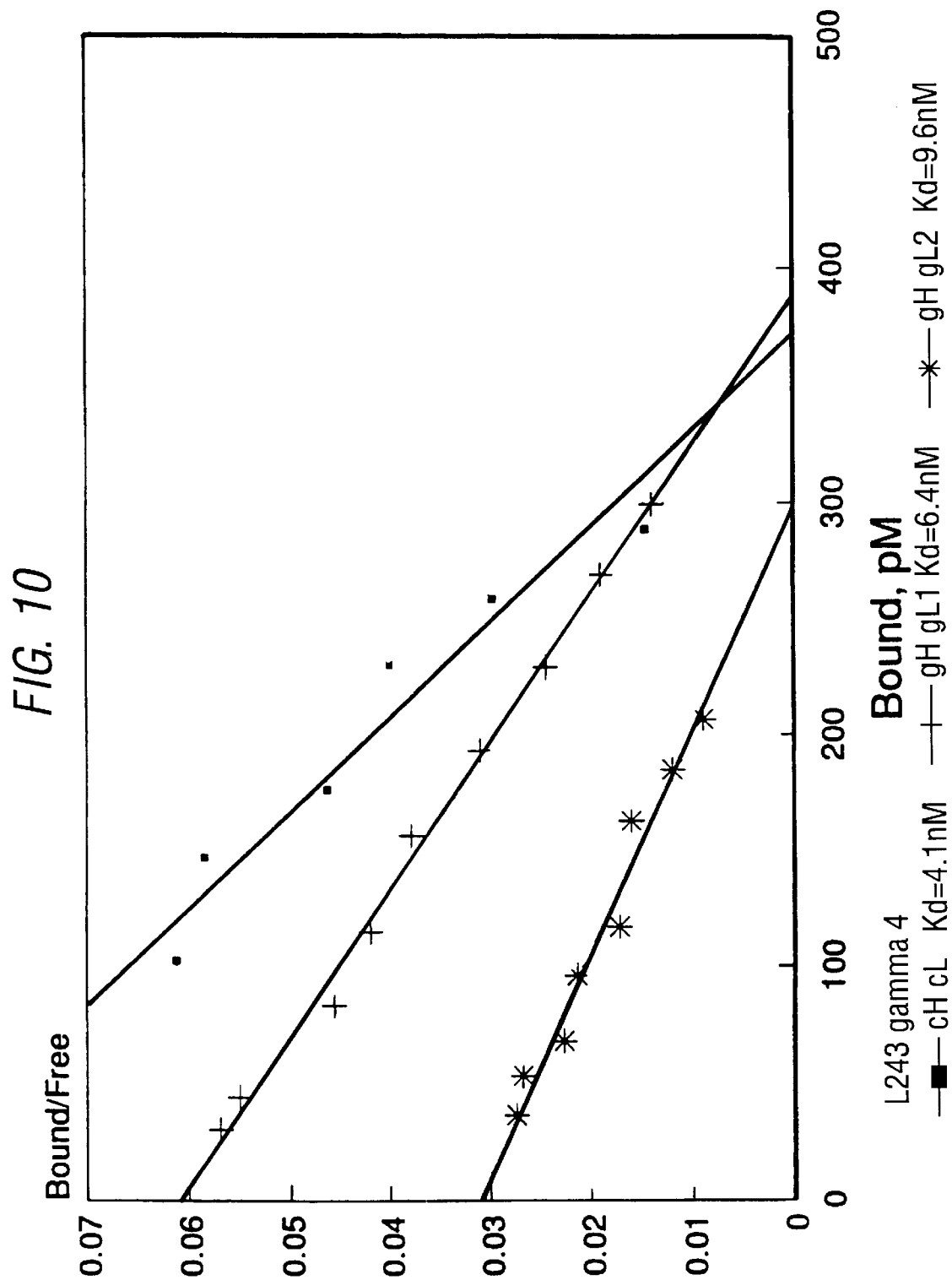

FIG. 10: shows a graph of a Scatchard analysis for 1L243 gamma 4

| | | |
|---|---|---|
| ■ | cH cL | Kd = 4.1 nM |
| + | gH gL1 | Kd = 6.4 nM |
| * | gH gL2 | Kd = 9.6 nM |

Figure 11:
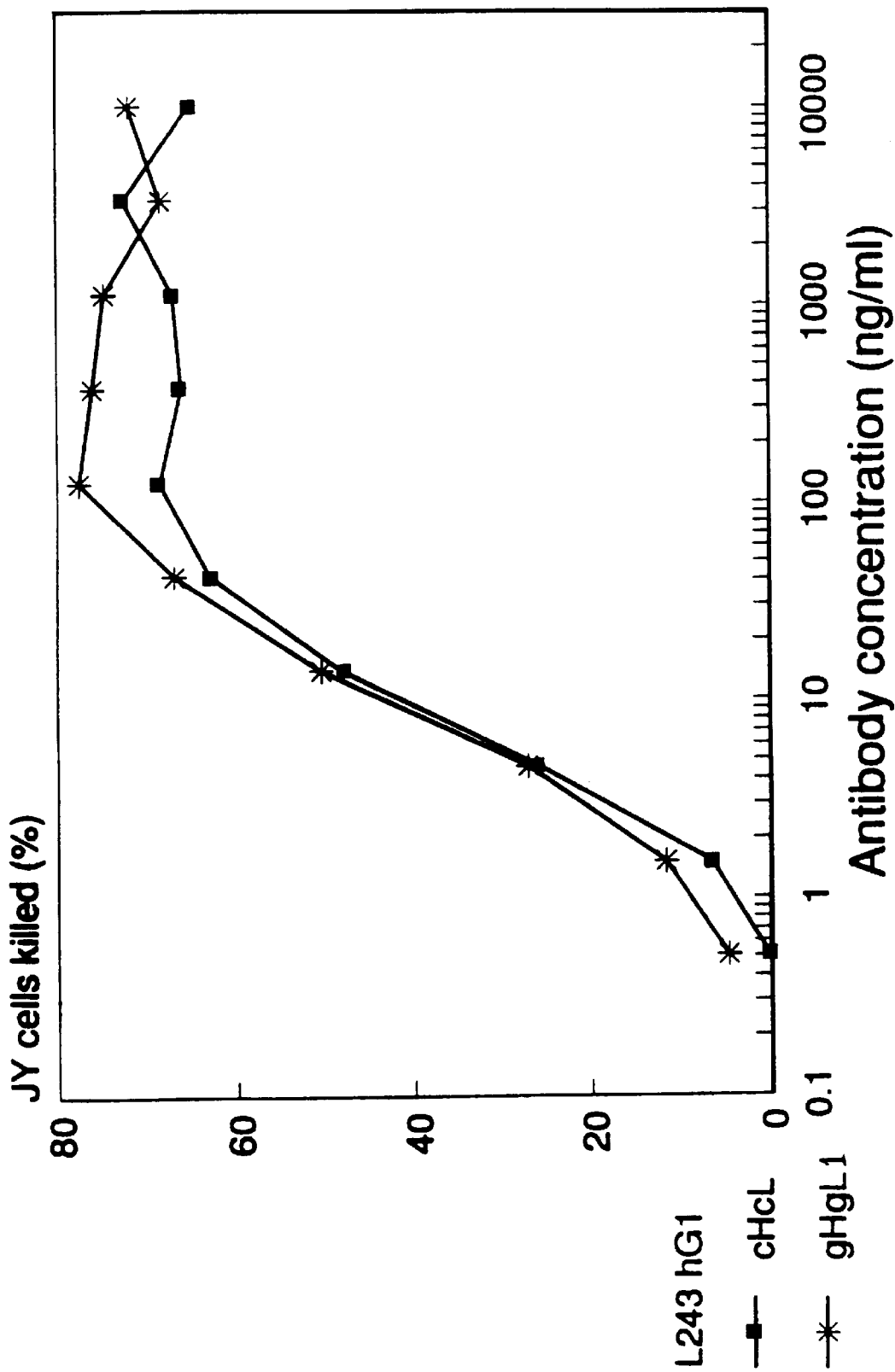

FIG. 11: shows a graph of FcRIII binding of chimeric and grafted L243 as measured by ADCC
- cH cL
+ gH gL1

Figure 12:
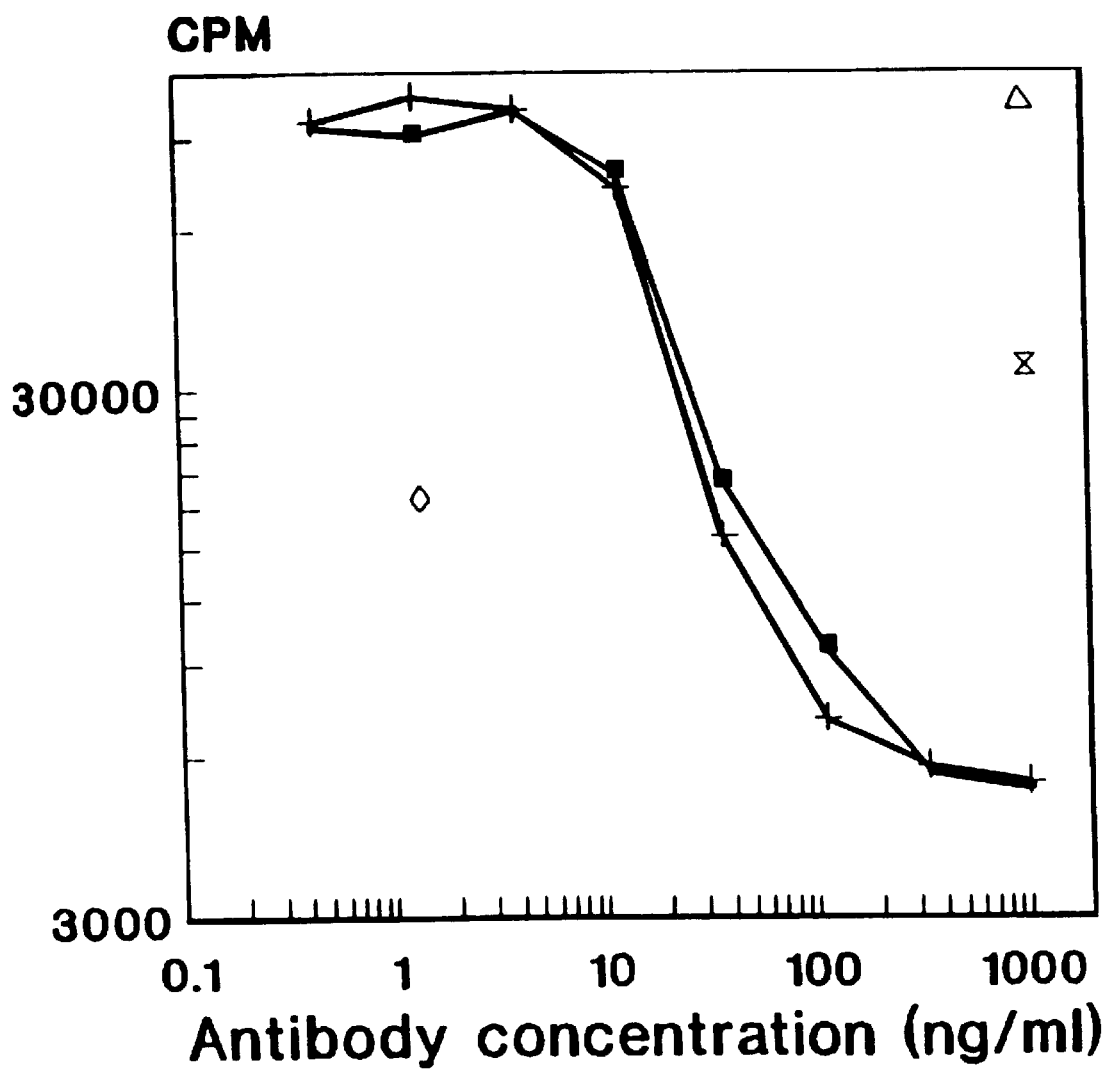

FIG. 12: shows a graph of L243 Isotype series MLR
- G1 L243cHcL
+ G1 L243 gH gL1
◇ Cyclosporin A
△ Medium control
x Responder alone FIG. 13: shows a graph of L243 Isotype Series UT Response
- G1 L243 cH cL
+ G1 L243 gH gL1
◇ Cyclosporin A
△ Medium control
x Responder alone FIG. 14: shows the nucleotide and amino acid SEQ ID NO: 84 sequence of the hinge and part of the $C_H2$ region SEQ ID NO: 85 of human C-gamma 1

Figure 15:
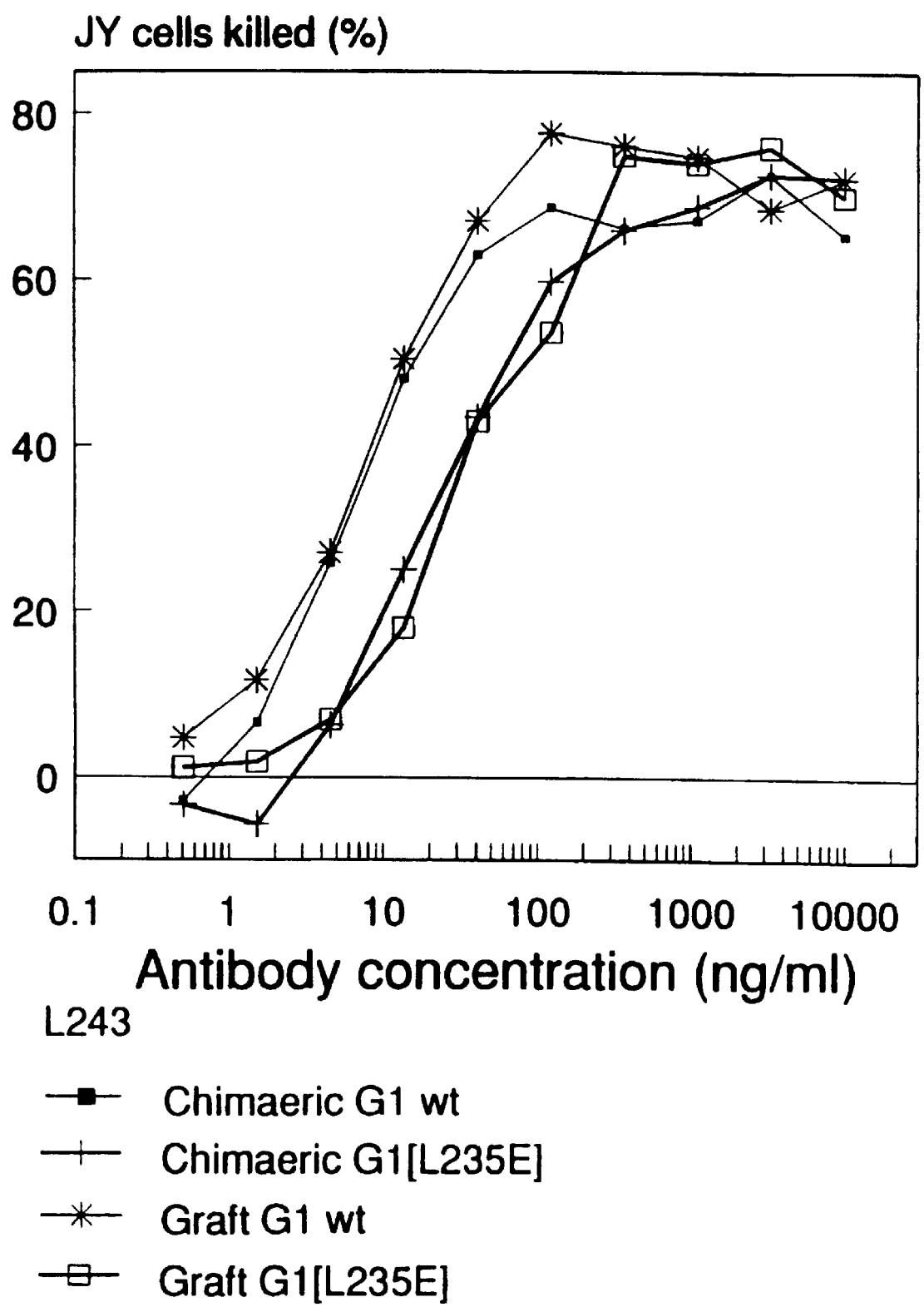

FIG. 15: shows a graph of FcRIII binding of chimeric, grafted and grafted [1L235E] L243 as measured by ADCC
- Chimeric G1 wt
+ Chimeric G1 [L235E]
* Graft G1 wt
◦ Graft G1 [L235E]

Figure 16:
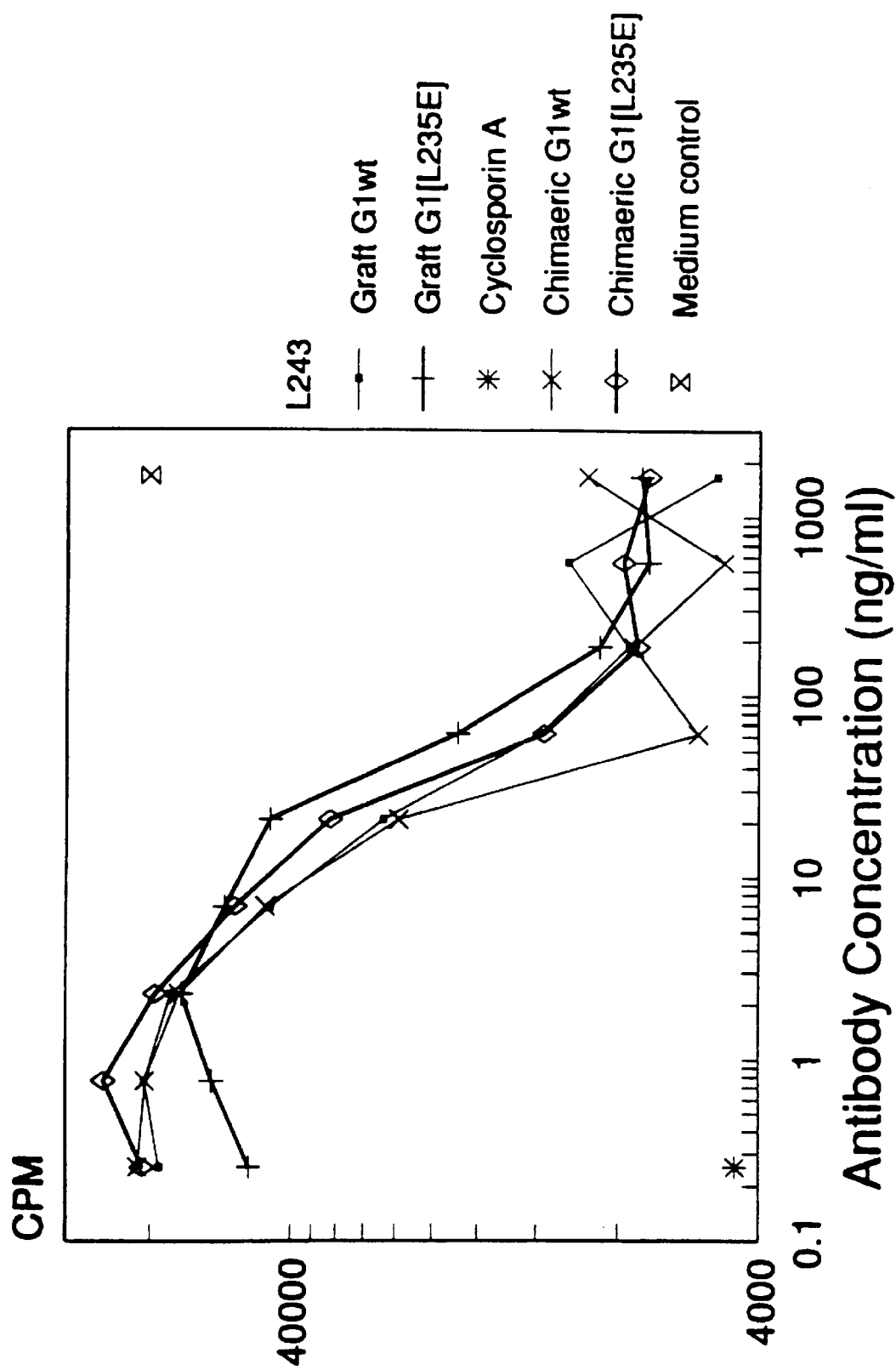
Figure 17:
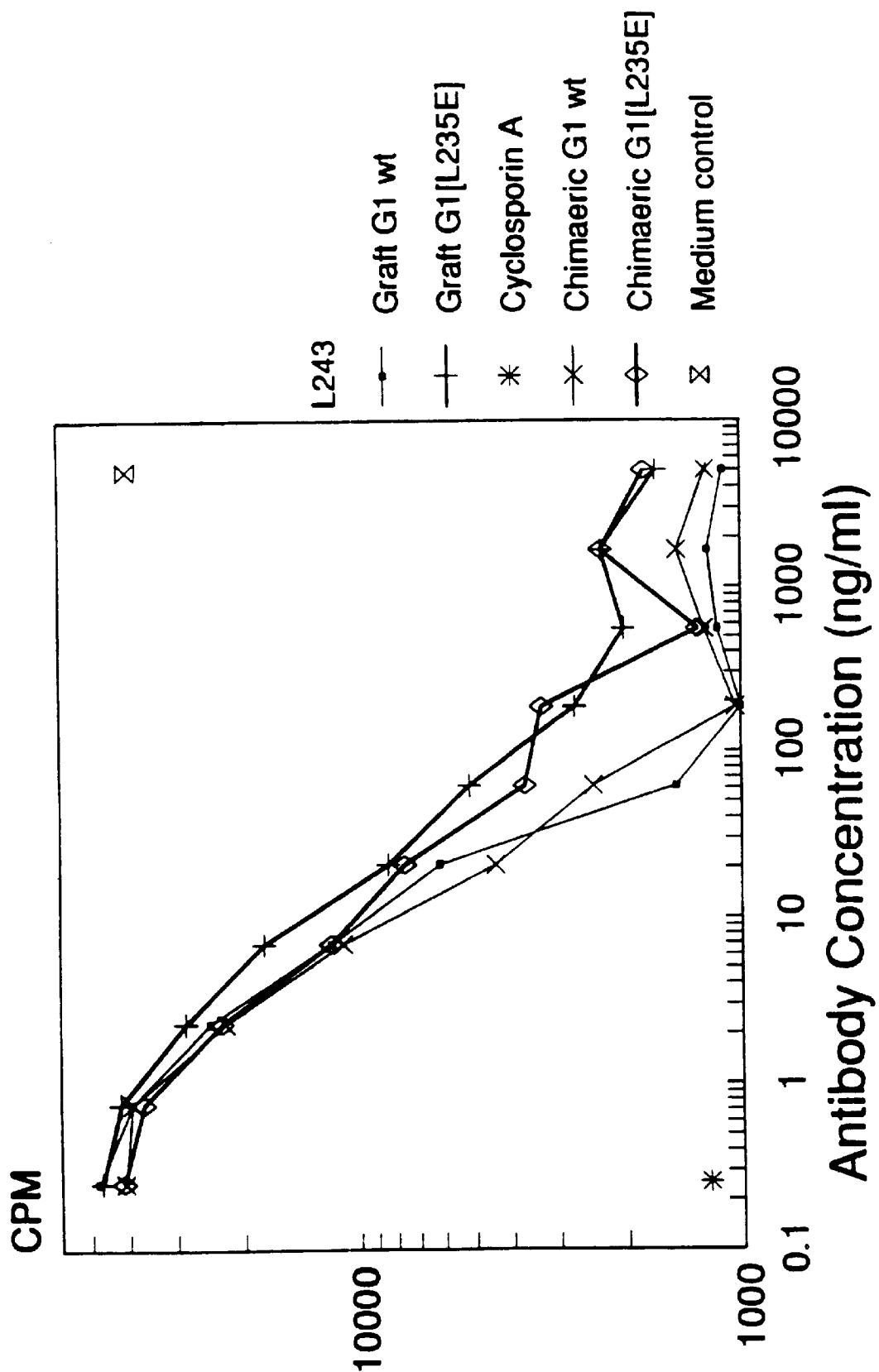
Figure 18:
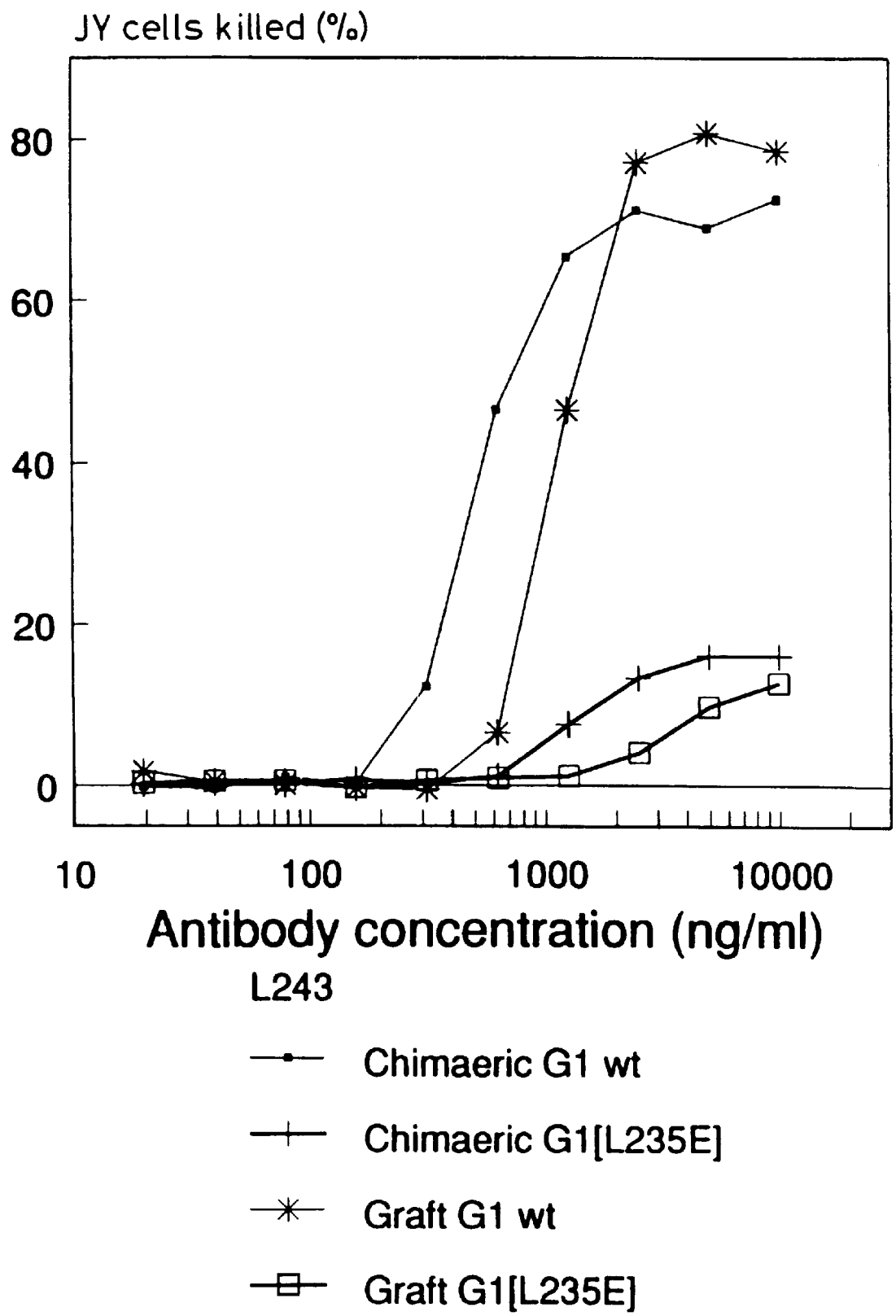

FIG. 16: shows a graph of immunosuppressive activity of CDR grafted L243 measured by MLR
- Graft G1 wt
+ Graft G[1 L235E]
* Cyclosporin A
* Chimeric G1 wt
◦ Chimeric G1 [L235E]
x Medium Control FIG. 17: shows a graph of CDR grafted L243 and grafted [L235E] L243 TT recall response
- Graft G1 wt
+ Graft G1 [L235E]
* Cyclosporin A
* Chimeric G1 wt
◦ Chimeric G1 [L235E]
x Medium Control FIG. 18: shows a graph of complement mediated cytotoxic potency of CDR grafted I243 and CDR grafted [L235E] L243
- Chimeric G1 wt
+ Chimeric G1 [L235E]
* Graft G1 wt
◦ Graft G1 [L235E]

FIG. 19: shows the nucleotide and amino acid sequences of
a) Clone 43 SEQ ID NO: 86 and 87, respectively
b) Clone 183 SEQ ID NO: 88 and 89, respectively and
c) Clone 192 SEQ ID NO: 90 and 91

Figure 20:
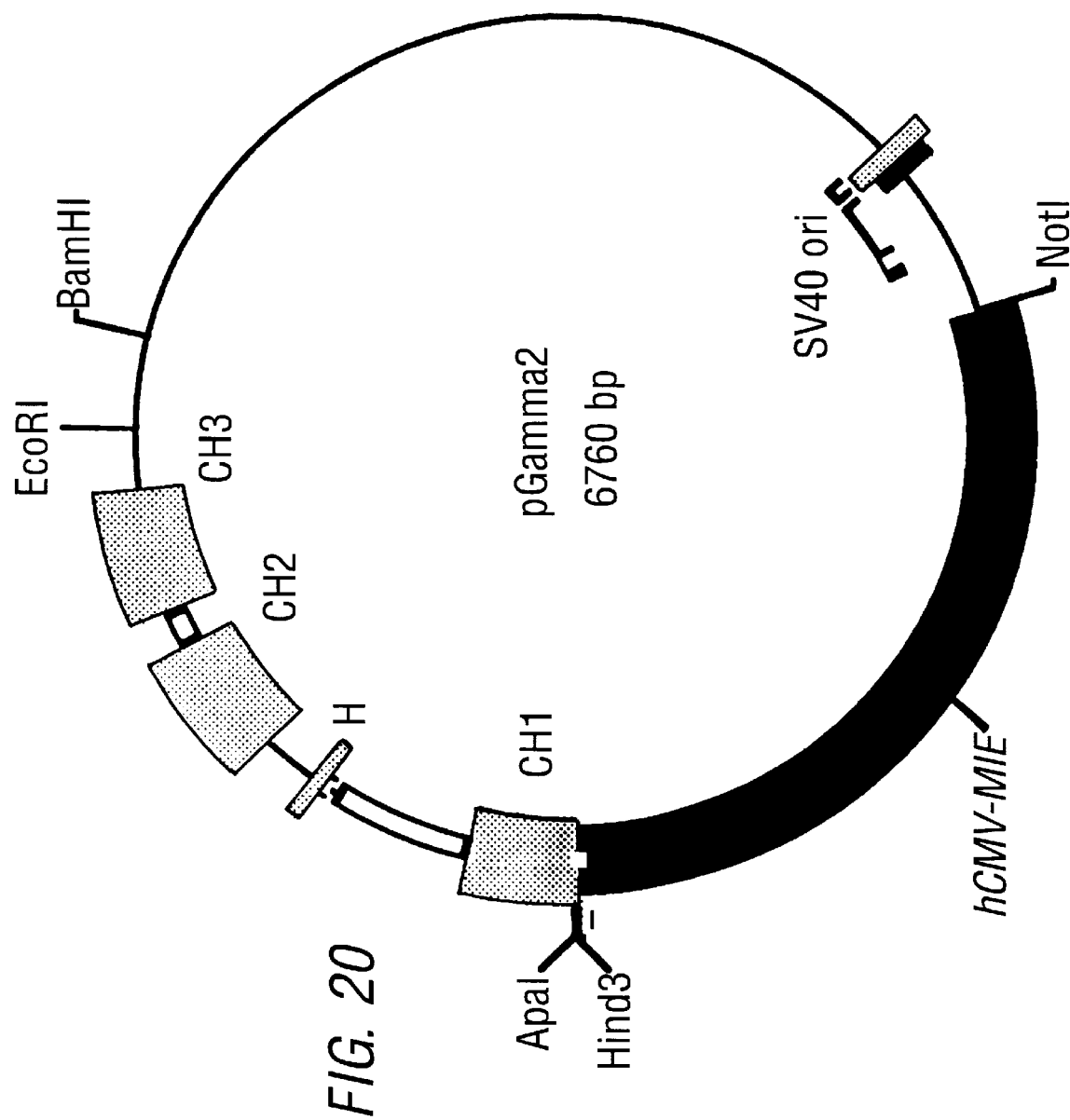

FIG. 20: shows a diagrammatic map of plasmid pGamma 2.

DETAILED DESCRIPTION OF THE SPECIFIC EMBODIMENTS OF THE INVENTION

EXAMPLE 1

Gene Cloning and Expression

RNA preparation from L243 hybridoma cells

Total RNA was prepared from 3×10 exp7 L243 hybridoma cells as described below. Cells were washed in physiological saline and dissolved in RNAzol (0.2 ml per 10 exp6 cells). Chloroform (0.2 ml per 2 ml homogenate) was added, the mixture shaken vigorously for 15 seconds and then left on ice for 15 minutes. The resulting aqueous and organic phases were separated by centrifugation for 15 minutes in an Eppendorf centrifuge and RNA precipitated from the aqueous phase by the addition of an equal volume of isopropanol. After 15 minutes ice, the RNA was pelleted by centrifugation, washed with 70% ethanol, dried and dissolved in sterile, RNAase free water. The yield of RNA was 350 µg.

Amino acid sequence of the L243 light chain.

The sequence of the first nine amino acids of the mature L243 light chain was determined to be NH2-DIQMTQSPAS SEQ ID NO: 92.

PCR cloning of L243 Vh and VI

The cDNA genes for the variable regions of L243 heavy and light chains were synthesised using reverse transcriptase to produce single stranded cDNA copies of the mRNA present in the total RNA, followed by Polymerase Chain Reaction (PCR) on the cDNAs with specific oligonucleotide primers.

a) cDNA synthesis cDNA was synthesised in a 20l reaction containing the following reagents: 50 mM Tris-HCl PH8.3, 75 mM KCl, 10 mM dithiothreitol, 3 mM $MgCl_2$, 0.5mM each deoxyribonucleoside triphosphates, 20 units RNAsin, 75 ng random hexanucleotide primer, 2 µg L243 RNA and 200 units Moloney Murine Leukemia Virus reverse transcriptase. After incubation at 42° C. for 60 mins the reaction was terminated by heating at 95OC for 5 minutes.

b) PCR

Aliquots of the cDNA were subjected to PCR using combinations of primers for the heavy and light chains. The nucleotide sequences of the 5' primers for the heavy and light chains are shown in Tables 1 and 2 respectively. These sequences, all of which contain a restriction site starting 6 nucleotides from their 5' ends, followed by the sequence GCCGCCACC SEQ ID NO: 93 to allow optimal translation of the resulting mRNAs, an initiator codon and a further 20–30 nucleotides, are a compilation based on the leader peptide sequences of known mouse antibodies [Kabat et al (1991) in Sequences of Proteins of Immunological Interest, 5th Edition—United States Department of Health and Human Services].

The 3' primers are shown in Table 3. The light chain primer spans the V-C junction of the antibody and contains a restriction site for the enzyme Spil to facilitate cloning of the VI PCR fragment. The heavy chain 3' primers are a mixture designed to span the J-C junction of the antibody. The first 23 nucleotides are identical to those found at the start of human C-gamma 1, 2, 3 and 4 genes and include the Apa1 restriction site common to these human isotypes. The 3' region of the primers contain a mixed sequence based on those found in known mouse antibodies [Kabat E A, Wu, T. T.; Perry H M, Gottesman K S, and Foeller L; In: Sequences of Proteins of Immunological Interest, 5th Edition, US Department of Health and Human Services (1991)].

The combinations of primers described above enables the PCR products for Vh and VI to be cloned directly into the appropriate expression vector (see below) to produce chimeric (mouse-human) heavy and light chains and for these genes to be expressed in mammalian cells to produce chimeric antibodies of the desired isotype.

Incubations (20 µl) for the PCR were set up as follows. Each reaction contained 10 mM Tris-HCl pH 8.3, 1.5 mM $MgCl_2$, 50 mM KCl, 0.01% w/v gelatin, 0.25 mM each deoxyribonucleoside triphosphate, 1–6 pmoles 5' primer mix (Table 4), 6 pmoles 3' primer, 1 λl cDNA and 0.25 units Taq polymerase. Reactions were incubated at 95° C. for 5 minutes and then cycled through 94° C. for 1 minute, 55° C. for 1 minute and 72° C. for 1 minute. After 30 cycles, aliquots of each reaction were analysed by electrophoresis on an agarose gel. Reactions containing 5' primer mixes B1, B2, B3 and B5 produced bands with sizes consistent with full length VI fragments while reaction B9 produced a fragment with a size expected of a Vh gene. The band produced by the Bi primers was not followed up as previous results had shown that this band corresponds to a light chain pseudogene produced by the hybridoma cell.

c) Molecular cloning of the PCR fragments.

DNA fragments produced in reactions B2, B3 and B5 were digested with the enzymes BstB1 and Spl1, concentrated by ethanol precipitation, electrophoresed on a 1.4% agarose gel and DNA bands in the range of 400 base pairs recovered. These were cloned by ligation into the vector pMR15.1 (FIG. 3) that had been restricted with BstB1 and Spi1. After ligation, mixtures were transformed into *E. coli* LM1035 and plasmids from the resulting bacterial colonies screened for inserts by digestion with BstB1 and Spl1. Representatives with inserts from each ligation were analysed further by nucleotide sequencing.

In a similar manner, the DNA fragments produced in reaction B9 and digested with HindIII and Apa1 were cloned into the vector pMR14 (FIG. 6) that had been restricted with HindIII and Apa1. Again, representative plasmids containing inserts were analysed by nucleotide sequencing.

d) Nucleotide sequence analysis

Plasmid DNA (pE1701 and pE1702) from two isolates containing Vh inserts from reaction B9 was sequenced using the primers R1053 (which primes in the 3' region of the HCMV promoter in pMR14) and R720 (which primes in the 5' region of human C-gamma 4 and allows sequencing through the DNA insert on pMR14). The determined nucleotide sequence and predicted amino acid sequence of L243 Vh in pE1702 is given in FIG. 2. The nucleotide sequence for the Vh insert in pE1701 was found to be identical to that in pE1702 except at nucleotide 20 (A in pE1701) and nucleotide 426 (A in pE1701). These two differences are in the signal peptide and J regions of Vh respectively and indicate that the two clones examined are independent isolates arising from the use of different primers from the mixture of oligonucleotides during the PCR stage.

To analyse the light chain clones, sequence derived from priming with R1053 was examined. The nucleotide sequence and predicted amino acid sequence of the VI genes arising from reactions B2 (clone 183), B3 (clone 43 and B5 (clone 192) are shown in FIG. 19. Comparison of the predicted protein sequences shows the following:

i) clones 182, 183, 43 and 45 all code for a VI gene which, when the signal peptide is removed, produces a light chain whose sequence is identical to that determined by amino acid sequence analysis for L243 light chain (see above).
ii) clones 182 and 183 contain a VI gene that codes for a signal peptide of 20 amino acids, while the VI gene in clones 43 and 45 results from priming with a different set of oligonucleotides and has a leader sequence of only 15 amino acids.
iii) Clone 192 does not code for L243 VI. Instead, examination of the database of antibody sequences (Kabat, 1991) indicates that clone 192 contains the VI gene for MOPC21, a light chain synthesised by the NS1 myeloma fusion partner used in the production of the L243 hybridoma.
iv) Clones 182 and 183 are identical except at nucleotide 26 (T in clone 182, C in clone 183). This difference can be accounted for by the use of different primers in the PCR and indicates that clones 182 and 183 are independent isolates of the same gene. The nucleotide sequence and predicted amino acid sequence of the complete VI gene from clone 183 is shown in FIG. 1.

Construction of human gamma 1 and gamma 2 isotypes.

The L243 Vh gene was subcloned on a HindIII-Apa1 fragment into pGamma 1 and pGamma 2, vectors containing the human C-gamma 1 and C-gamma 2 genes respectively (FIGS. 8 and 20).

Human Isotype mutants

PCR mutagenesis was used to change residue 235 in human C-gamma1 contained in the vector pGamma 1 from leucine to either glutamic acid or to alanine and to change residue 237 from glycine to alanine. The lower hinge region of human C-gamma 1 was also replaced by the corresponding region of human C-gamma 2. The following oligonucleotides were used to effect these changes:

I) L235E change

R4911 5'GCACCTGAACTCGAGGGGGGACCGT-CAGTC3' SEQ ID NO: 1

R4910 5'CCCCCCTCGAGTTCAGGTGCTGAGGMG3' SEQ ID NO: 2

II) L235A change

R5081 5'GCACCTGAACTCGCAGGGGGACCGT-CAGTC3' SEQ ID NO: 3

R5082 5'GACTGACGGTCCCCCTGCGAGTTCAG-GTGC3' SEQ ID NO: 4

III) G237A change

R5088 5'GCACCTGMCTCCTGGGTGCACCGT-CAGTC3' SEQ ID NO: 5

R5087 5'GACTGACGGTGCACCCAGGAGTTCAG-GTGC3' SEQ ID NO: 6

IV) Exchange of lower hinge regions

R4909 5'GCACCTCCAGTGGCAGGACCGTCAGTCT-TCCTC3' SEQ ID NO: 7

R4908 5'CGGTCCTGCCACTGGAGGTGCTGAGGM-GAG3' SEQ ID NO: 8

Other oligonucleotides used in the PCR mutagenesis are:

R4732 5'CAGCTCGGACACCTTCTCTCCTCC3' SEQ ID NO: 9

R4912 5'CCACCACCACGCATGTGACC3' SEQ ID NO: 10

R4732 and R4912 prime between nucleotides 834 and 858 and between nucleotides 1156 and 1137 respectively in human C-gamma 1 (FIG. 14).

The general strategy for the PCR mutagenesis was as follows. For each amino acid change, two rounds of PCR were used to generate DNA fragments containing the required substitutions. These fragments were then restricted with the enzymes BgI II and Sty1 and used to replace the corresponding fragments containing the wild type sequence in the pGamma 1 vector, (FIG. 8).

For the first round PCR, reactions (20 µl) were prepared containing the following reagents: 10 mM Tris-HCl pH 8.3, 1.5 mM $MgCl_2$, 50 mM KCl, 0.01% gelatin, 0.25 mM each deoxyribonucleoside triphosphate, 50 µg pGamma 1 DNA, 0.4 unit Taq polymerase and 6 pmoles of each of the primer. The following combinations of primers were used:

R4911/R4912,
R4910/R4732,
R5081/R4912,
R5082/R4732,
R5088/R4912,
R5087/R4732,
R4909/R4912,
R4908/R4732.

After 30 cycles through 94° C. for 1 minute, 55° C. for 1 minute and 72° C. for 1 minute, the reactions were extracted with chloroform, the newly synthesised DNA precipitated with ethanol, dissolved in water and electrophoresed on a 1.4% agarose gel. Gel slices containing the DNA fragments were excised from the gel, the DNA recovered from the agarose using a "Mermaid"™ kit (from Stratech Scientific Ltd., Luton, England) and eluted into 20 µl sterile water.

Second round PCR was in a 100 µl reaction containing 10 mM Tris-HCl pH 8.3, 1.5 mM $MgCl_2$, 50 mM KCl, 0.01% gelatin, 0.25 mM each deoxyribonucleoside triphosphate, 2 units Taq polymerase, ½₀ of each pair of DNA fragments from the first round reaction and 30 pmoles of each of R4732 and R4912. After 30 cycles, see above, the reactions were extracted with phenol/chloroform (1/1) and precipitated with ethanol. Fragments were digested with BgI11 and Sty1, electrophoresed on a 1.4% agarose gel and DNA bands of 250 base-pairs recovered from gel slices as previously described.

These BgI II-StyI fragments were ligated in a 3- way ligation to the 830 base-pair Sty1-EcoR1 fragment, containing the C-terminal part of the $C_H2$ domain and the entire $C_H3$ domain of human C-gamma 1, and the BglII-EcoR1 vector fragment from pGamma1 (see FIG. 8). After transformation into LM1035, plasmid minipreps from resulting colonies were screened for the presence of the BgI II-Sty1 fragment and representatives of each taken for nucleotide sequence analysis. From this, plasmids containing the desired sequence were identified and, for future reference, named as follows:

pGamma1[L235E] containing glutamic acid at residue 235,
pGamma1[L235A] containing alanine at residue 235,
pGamma1[G237A] containing alanine at residue 237,
pGamma 1 [g1→g2] containing the C-gamma 2 lower hinge region.

The above plasmids were each restricted with HindIII and Apa1 and the HindIII-Apa1 fragment containing L243 Vh inserted to produce the following plasmids:

L243Gamma1[L1235E]
L243Gamma1[L235A]
L243Gamma1[G237A]
L243Gamma [g1→g2]

Production of chimeric L243 antibody

Antibody for biological evaluation was produced by transient expression of the appropriate heavy and light chain pairs after co-transfection into Chinese Hamster Ovary (CHO) cells using calcium phosphate precipitation.

On the day prior to transfection, semi-confluent flasks of CHO-L761 cells were trypsinised, the cells counted and T75 flasks set up each with 10 exp7 cells.

On the next day, the culture medium was changed 3 hours before transfection. For transfection, the calcium phosphate precipitate was prepared by mixing 1.25 ml of 0.25 M $CaCl_2$ containing 50 μg of each of heavy and light chain expression vectors with 1.25 ml of 2× HBS (16.36 gm NaCl, 11.9 gm HEPES and 0.4 gm $Na_2HPO_4$ in 1 liter water with the pH adjusted to 7.1 with NaOH) and adding immediately into the medium on the cells. After 3 hours at 37 C in a CO2 incubator, the medium and precipitate were removed and the cells shocked by the addition of 15 ml 15% glycerol in phosphate buffered saline (PBS) for 1 minute. The glycerol was removed, the cells washed once with PBS and incubated for 48–96 hours in 25 ml medium containing 10 mM sodium butyrate. Antibody was purified from the culture medium by binding to and elution from protein A-Sepharose. Antibody concentration was determined using a human Ig ELISA (see below).

ELISA

For the ELISA, Nunc ELISA plates were coated overnight at 4° C. with a F(ab)2 fragment of a polyclonal goat anti-human Fc fragment specific antibody (Jackson Immuno-research, code 109-006-098) at 5 μg/ml in coating buffer (15 mM sodium carbonate, 35 mM sodium hydrogen carbonate, pH6.9). Uncoated antibody was removed by washing 5 times with distilled water. Samples and purified standards to be quantitated were diluted to approximately 1 μg/ml in conjugate buffer (0.1 M Tris-HCl pH7.0, 0.1M NaCl, 0.2% v/v Tween 20, 0,2% w/v Hammersten casein). The samples were titrated in the microtitre wells in 2-fold dilutions to give a final volume of 0.1 ml in each well and the plates incubated at room temperature for 1 hr with shaking. After the first incubation step the plates were washed 10 times with distilled water and then incubated for 1 hr as before with 0.1 ml of a mouse monoclonal anti-human kappa (clone GD12) peroxidase conjugated antibody (The Binding Site, code MP135) at a dilution of 1 in 700 in conjugate buffer. The plate was washed again and substrate solution (0.1 ml) added to each well. Substrate solution contained 150 μl N,N,N,N-tetramethylbenzidine (10 mg/ml in DMSO), 150 μl hydrogen peroxide (30% solution) in 10 ml 0.1M sodium acetate/sodium citrate, pH6.0. The plate was developed for 5-10 minutes until the absorbance at 630 nm was approximately 1.0 for the top standard. Absorbance at 630 nm was measured using a plate reader and the concentration of the sample determined by comparing the titration curves with those of the standard.

TABLE 1

Oligonucleotide primers for the 5' region of mouse heavy chains.

| | | |
|---|---|---|
| CH1 : | 5'ATGAAATGCAGCTGGGTCAT(G,C)TTCTT3' | SEQ ID NO: 11 |
| CH2 : | 5'ATGGGATGGAGCT(A,G)TATCAT(C,G)(C,T)TCTT3' | SEQ ID NO: 12 |
| CH3 : | 5'ATGAAG(A,T)TGTGGTTAAACTGGGTTTT3' | SEQ ID NO: 13 |
| CH4 : | 5'ATG(G,A)ACTTTGGG(T,C)TCAGCTTG(G,A)T3' | SEQ ID NO: 14 |
| CH5 : | 5'ATGGACTCCAGGCTCAATTTAGTTTT3' | SEQ ID NO: 15 |
| CH6 : | 5'ATGGCTGTC(C,T)T(G,A)G(G,C)GCT(G,A)CTCTTCTG3' | SEQ ID NO: 16 |
| CH7 : | 5'ATGG(G,A)ATGGAGC(G,T)GG(G,A)TCTTT(A,C)TCTT3' | SEQ ID NO: 17 |
| CH8 : | 5'ATGAGAGTGCTGATTCTTTTGTG3' | SEQ ID NO: 18 |
| CH9 : | 5'ATGG(C,A)TTGGGTGTGGA(A,C)CTTGCTATT3' | SEQ ID NO: 19 |
| CH10: | 5'ATGGGCAGACTTACATTCTCATTCCT3' | SEQ ID NO: 20 |
| CH11: | 5'ATGGATTTTGGGCTGATTTTTTTTATTG3' | SEQ ID NO: 21 |
| CH12: | 5'ATGATGGTGTTAAGTCTTCTGTACCT3' | SEQ ID NO: 22 |

Each of the above primers has the sequence 5'GCGCGCAAGCTTGCCGCCACC3' SEQ ID NO: 94 added to its 5' end.

TABLE 2

Oligonucleotide primers for the 5' region of mouse light chains.

| | | |
|---|---|---|
| CL1: | 5'ATGAAGTTGCCTGTTAGGCTGTTGGTGCT3' | SEQ ID NO: 23 |
| CL2: | 5'ATGGAG(T,A)CAGACACACTCCTG(T,C)TATGGGT3' | SEQ ID NO: 24 |
| CL3: | 5'ATGAGTGTGCTCACTCAGGTCCT3' | SEQ ID NO: 25 |
| CL4: | 5'ATGAGG(G,A)CCCCTGCTCAG(A,T)TT(C,T)TTGG3' | SEQ ID NO: 26 |
| CL5: | 5'ATGGATTT(T,A)CAGGTGCAGATT(T,A)TCAGCTT3' | SEQ ID NO: 27 |
| CL6: | 5'ATGAGGT(T,G)C(T,C)(T,C)TG(T,C)T(G,C)AG(T,C)T(T,C)CTG(A,G)G3' | SEQ ID NO: 28 |

TABLE 2-continued

Oligonucleotide primers for the 5' region of mouse light chains.

| | | |
|---|---|---|
| CL7: | 5'ATGGGC(T,A)TCAAGATGGAGTCACA3' | SEQ ID NO: 29 |
| CL8: | 5'ATGTGGGGA(T,C)CT(G,T)TTT(T,C)C(A,C)(A,C)TTT TTCAAT3' | SEQ ID NO: 30 |
| CL9: | 5'ATGGT(G,A)TCC(T,A)CA(G,C)CTCAGTTCCTT3' | SEQ ID NO: 31 |
| CL10: | 5'ATGTATATATGTTTGTTGTCTATTTC3' | SEQ ID NO: 32 |
| CL11: | 5'ATGGAAGCCCCAGCTCAGCTTCTCTT3' | SEQ ID NO: 33 |

Each of the above primers has the sequence 5'GGACTGTTCGMGCCGCCACC3' SEQ ID NO: 95 added to its 5' end.

TABLE 3

Oligonucleotide primers for the 3' ends of mouse Vh and Vl genes.

Light chain (CL12):
5'GGATACAGTTGGTGCAGCATCCGTACGTTT3'     SEQ ID NO: 34

Heavy chain (R2155):
5'GCAGATGGGCCCTTCGTTGAGGCTG(A,C)(A,G)GAGAC(G,T,A)GTGA3'     SEQ ID NO: 35

TABLE 4

5' Primer mixtures for PCR

| | |
|---|---|
| B1 | CL2. |
| B2 | CL6. |
| B3 | CL8. |
| B4 | CL4, CL9. |
| B5 | CL1, CL3, CL5, CL7, CL10, CL11. |
| B6 | CH6. |
| B7 | CH7. |
| B8 | CH2, CH4. |
| B9 | CH1, CH3, CH5, CH8, CH9, CH10, CH11, CH12. |

EXAMPLE 2

L243 is a mouse monoclonal antibody raised against human MHC Class II. The nucleotide and amino acid sequences of L243 Vl and Vh are shown in FIGS. 1 and 2 respectively. The following examples describe the humanisation of the L243 antibody (CDR grafting).

CDR grafting of L243 light chain

Alignment of the framework regions of L243 light chain with those of the four human light chain subgroups [Kabat, E. A., Wu, T. T., Perry, H. M., Gottesman, K. S. and Foeller, C. 1991, Sequences of Proteins of Immunological Interest, Fifth Edition] revealed that L243 was most homologous to antibodies in human light chain subgroup 1. Consequently, for constructing the CDR grafted light chain, the framework regions chosen corresponded to those of the human Group 1 consensus sequence. A comparison of the amino acid sequences of the framework regions of L243 and the consensus human group I light chains is given below and shows that there are 21 differences (underlined) between the two sequences.

Analysis of the contribution that any of these framework differences might have on antigen binding (see published International patent application No. WO91/09967) identified 4 residues for investigation; these are at positions 45,49,70 and 71. Based on this analysis, two versions of the CDR grafted light chain were constructed. In the first of these, L243-gL1, residues 45,49,70 and 71 are derived from the L243 light chain while in the second, L243-gL2, all residues are human consensus.

Light Chain Residues

Resides 37 (Gin to Arg) and 48 (Ile to Val) would be included in any future grafted molecules.

Light chain Comparisons

Hu group 1 consensus: DIQMTQSPSSLSRSUGORUTITC SEQ ID NO: 36

| | | |
|---|---|---|
| Hu group 1 consensus | DIQMTQSPSSLSASUGDAVTITC | SEQ ID NO:36 |
| L243 | DIQMTQSP<u>A</u>SLS<u>V</u>SVG<u>ET</u>VTITC | SEQ ID NO:37 |

```
                                4   4
                                5   9
```

| | | |
|---|---|---|
| Hu Group 1 consensus | WYQQKPGKAPKLLIY SEQ ID NO:38 | |
| L243 | WY<u>RQ</u>K<u>Q</u>GK<u>SPQ</u>LL<u>UF</u> | SEQ ID NO:39 |

```
                                7
                                7
                                0
                                1
```

| | | |
|---|---|---|
| Hu Group 1 consensus | GVPSRFSGSGSGTDFTLTISSLQPEDFATYYC | SEQ ID NO:40 |
| L243 | GVPSAFSGSGSGT<u>QYSLKI</u>NSLQ<u>S</u>EDF<u>GD</u>YYC | SEQ ID NO:41 |

| Hu Group 1 consensus | FGQGTKVEIKA | SEQ ID NO:42 |
| L243 | FG<u>GG</u>GT<u>NL</u>EIKA | SEQ ID NO:43 |

Construction of CDR grafted light chain L243-gL1

The construction of L243-gL1 is given below in detail. The following oligonucleotides were used in the Polymerase Chain Reactions (PCR) to introduce changes into the framework regions of the chimeric light chain:

R5043: 5'GTRGGRGRCCGGGTCRCCRTCRCRT-GTCGRGCRR3' SEQ ID NO: 44

R5044: 5'CTGRGGRGCTTTTCCTGGTTTCTGCTGR-TRCCRTGCTARR3' SEQ ID NO: 45

R5045: 5'RRRCCRGGRRRRGCTCCTCRGCTCCT-GRTCTTTGCTGCRTC3' SEQ ID NO: 46

R5046: 5'CTTCTGGCTGCRGGCTGGRGRTRGT-TRGGGTRTRCTGTGTGCC3' SEQ ID NO: 47

R5047: 5'CTTCRGCCTGCRGCCRGRRGRTTTTGC-TRCTTRTTRCTGTCRR3' SEQ ID NO: 48

R5048: 5'GGGCCGCTRCCGTRCGTTTTRGTTC-CRCTTTGGTGCCTTGRCCGHR3' SEQ ID NO: 49

Three reactions, each of 20 µl, were set up each containing 10 mM Tris-HCl pH 8.3,1.5 mM MgCl2, 50 mM KCl, 0.01% w/v gelatin, 0.25 mM each deoxyribonucleoside triphosphate, 0.1 µg chimeric L243 light chain DNA, 6 pmoles of R5043/R5044 or R5045/R5046 or R5047/R5048 and 0.25 units Taq polymerase. Reactions were cycled through 94° C. for 1 minute, 55° C. for 1 minute and 72° C. for 1 minute. After 30 cycles, each reaction 35 was analysed by electrophoresis on an agarose gel and the PCR fragments excised from the gel and recovered using a Mermaid Kit (supplied by Stratech Scientific Ltd., Luton, England).

Aliquots of these were then subjected to a second round of PCR. The reaction, 100 µl, contained 10 mM Tris-HCl pH 8.3, 1.5 mM MgCl2, 50 mM KCl, 0.01% w/v gelatin, ⅒ of each of the three PCR fragments from the first set of reactions, 30 pmoles of R5043 and R5048 and 2.5 units Taq polymerase. Reaction temperatures were as above. After the PCR, the mixture was extracted with phenol/chloroform and then with chloroform and precipitated with ethanol. The ethanol precipitate was recovered by centrifugation, dissolved in the appropriate buffer and restricted with the enzymes BstEII and SpII. The resulting product was finally electrophoresed on an agarose gel and the 270 base pair DNA fragment recovered from a gel slice and ligated into the vector pMR15.1 (FIG. 3) that had previously been digested with the same enzymes.

The ligation mixture was used to transform *E. coli* LM1035 and resulting colonies analysed by PCR, restriction enzyme digests and nucleotide sequencing. The nucleotide and amino acid sequence of the VI region of L243-gL1 is shown in FIG. 4.

Construction of CDR grafted light chain L243-gL2

L243-gL2 was constructed from L243-gL1 using PCR. The following oligonucleotides were used to introduce the amino acid changes:

R1053: 5'GCTGACRGRCTRRCRGRCTGTTCC3' SEQ ID NO: 50

R5350: 5'TCTRGRTGGCRCRCCRTCT-GCTARGTTTGRTGCRGCATRGRTCAG-GRGCTTAGG AGC3' SEQ ID NO: 51

R5349: 5'GCRGRTGGTGTGCCRTCTRGRTTCRGTG-GCRGTGGRTCRGGCRCRGRCTTTACC CTRRC3' SEQ ID NO: 52

R684: 5'TTCRACTGCTCATCRGRT3' SEQ ID NO: 53

Two reactions, each 20 µl, were set up each containing 10 mM Tris-HCl pH 8.3, 1.5 mM MgCl2, 50 mM KCl, 0.01% w/v gelatin, 0.25 mM each deoxyribonucleoside triphosphate, 0.1 µg L243-gL1, 6 pmoles of R1053/R5350 or R5349/R684 and 0.25 units Taq polymerase. Reactions were cycled through 94° C. for 1 minute, 55° C. for 1 minute and 72° C. for 1 minute. After 30 cycles, each reaction was analysed by electrophoresis on an agarose gel and the PCR fragments excised from the gel and recovered using a Mermaid Kit.

Aliquots of these were then subjected to a second round of PCR. The reaction, 100 µl, contained 10 mM Tris-HCl pH 8.3,1.5 mM MgCl2, 50 mM KCl, 0.01% w/v gelatin, ⅕ of each of the PCR fragments from the first set of reactions, 30 pmoles of R1053 and R684 and 2.5 units Taq polymerase. Reaction temperatures were as above. After the PCR, the mixture was extracted with phenol/chloroform and then with chloroform and precipitated with ethanol. The ethanol precipitate was recovered by centrifugation, dissolved in the appropriate buffer and restricted with the enzymes BstEII and SpII. The resulting product was finally electrophoresed on an agarose gel and the 270 base pair DNA fragment recovered from a gel slice and ligated into the vector pMR15.1 (FIG. 3) that had previously been digested with the same enzymes.

The ligation mixture was used to transform *E. coli* LM1035 and resulting colonies analysed by PCR, restriction enzyme digests and nucleotide sequencing. The nucleotide and amino acid sequence of the VI region of L243-gL2 is shown in FIG. 5.

CDR grafting of L243 heavy chain

CDR grafting of L243 heavy chain was accomplished using the same strategy as described for the light chain. L243 heavy chain was found to be most homologous to human heavy chains belonging to subgroup 1 and therefore the consensus sequence of the human subgroup 1 frameworks was chosen to accept the L243 heavy chain CDRs.

A comparison of the framework regions of the two structures is shown below where it can be seen that L243 differs from the human consensus at 28 positions (underlined). After analysis of the contribution that any of these might make to antigen binding, only residues 27, 67, 69, 71, 72, and 75 were retained in the CDR grafted heavy chain, L243-gH.

Heavy Chain Residues

Residues 2 (Val to Ile) and 46 (Glu to Lys) would be incorporated into any future grafted molecules. In addition to these two residues the murine residue 67 which is present in L243 gH would be changed back to the human consensus residue i.e. Phe to Val change.

Heavy chain comparisons

Hu Group 1 consensus: QVQLVQSGAEVKKPGAS-VKVSCKASGYTFT SEQ ID NO: 54

L243: Q<u>I</u>QLVQSGPELKKPGETVKISCKASGFTFT SEQ ID NO: 55

```
                                    2
                                    7
Hu group 1 consensus  QVQLVQSGAEUKKPGASUKUSCKASGYTFT  SEQ ID NO:54
L243                  QIQLVQSGPELKKPGETUKISCKASGFTFT  SEQ ID NO:55

Hu Group 1 consensus  WVRQRPGQGLEWMG  SEQ ID NO:56
L243                  WVKQAPGKGLKWMG  SEQ ID NO:57

6 6 77  7
                      7 9 12  5
Hu Group 1 consensus  RUTITADTSTSTAYMELSSLRSEDTRVYYCAA  SEQ ID NO:58
L243                  RFAFSLETSASTRYLQINNLKNEDTAKYFCAR  SEQ ID NO:59

Hu Group 1 consensus  WGQGTLVTVSS
L243                  WGQGTTLTVSS
```

Hu Group 1 consensus: RVTITADTSTSTAYMELSSL-RSEDTAVYYCAR SEQ ID NO: 58
L243: RFAFSLETSASTAYLQINNLKNEDTAKYFCAR SEQ ID NO: 59
Hu Group 1 consensus: WGQGTLVTVSS
L243: WGQGTTLTVSS Construction of CDR grafted heavy chain, L243 gH L243gH was assembled by subjecting overlapping oligonucleotides to PCR in the presence of the appropriate primers. The following oligonucleotides were used in the PCR:

R3004: 5'GGGGGGAAGCTTGCCGCCACCATGG3' SEQ ID NO: 62
R3005: 5'CCCCCCGGGCCCTTTGTAGAAGCAG3' SEQ ID NO: 63
R4902: 5'GACAACAGGAGTGCACTCTCAGGTGCAGCTGGTGCAGTCTGGAGC AGAGGTGAAGAAGCCTGGAGCATCTG3' SEQ ID NO: 64
R4903: 5'ACATTCACAAATTACGGAATGAATTGGGTGAGACAGGCACCTGGA CAGGGACTCGAGTGGA3' SEQ ID NO: 65
R4904: 5'CCTACGTACGCAGACGACTTCAAGGGAAGATTCACATTCACACTG GAGACATCTGCATCTACAGCATACAT3' SEQ ID NO: 66
R4905: 5'CAGCAGTGTACTACTGTGCAAGAGACATTACAGCAGTGGTACCTA CAGGATTCGACTACTGGGGACAGGGA3' SEQ ID NO: 67
R4897: 5'TGAGAGTGCACTCCTGTTGTCACAGACAGGAAGRACAGGAACACC CAAGACCACTCCATGGTGGCGGCAAGCTTCCCCCC3' SEQ ID NO: 68
R4898: 5'CATTCCGTAATTTGTGAATGTGAATCCAGATGCCTTACAAGACAC CTTCACAGATGCTCCAGGCTTCTTCA3' SEQ ID NO: 69
R4899: 5'GAAGTCGTCTGCGTACGTAGGCTCTCTTGTGTRTGTATTAATCCA TCCCATCCACTCGAGTCCCTGTCCAG3' SEQ ID NO: 70
R4900: 5'TTGCACAGTAGTACACTGCTGTGTCCTCAGATCTCAGAGAAGACA GCTCCATGTATGCTGTAGATGCAGAT3' SEQ ID NO: 71
R4901: 5'CCCCCCGGGCCCTTTGTAGAAGCAGAAGACACTGTCACCAGTGTT CCCTGTCCCCAGTRGTCGAA3' SEQ ID NO: 72

The assembly reaction, 50 µl, contained 10 mM Tris-HCl pH 8.3, 1.5 mM MgCl2, 50 mM KCl, 0.01% w/v gelatin, 0.25 mM each deoxyribonucleoside triphosphate, 1 pmole of each of R4897-R4905, 10 pmoles of each of R3004 and R3005 and 2.5 units Taq polymerase. Reactions were cycled through 94° C. for 1 minute, 55° C. for 1 minute and 72° C. for 1 minute. After 30 cycles, the reaction was extracted with phenol/chloroform (1/1), then with chloroform and precipitated with ethanol. After centrifugation, the DNA was dissolved in the appropriate restriction buffer and digested with Hindlil and ApaI. The resulting fragment was isolated from an agarose gel and ligated into pMR14 (FIG. 6) that had previously been digested with the same enzymes. pMR14 contains the human gamma 4 heavy chain constant region and so the heavy chain expressed from this vector will be a gamma 4 isotype. The ligation mixture was used to transform E. coli LM1035 and resulting bacterial colonies screened by restriction digest and nucleotide sequence analysis. In this way, a plasmid containing the correct sequence for L43gH was identified (FIG. 7).

Construction of Gamma 1 versions of chimeric and CDR grafted L243 heavy chain

Human Gamma 1 versions of L243 heavy chains were constructed by transferring the variable regions of both the murine and the CDR grafted heavy chains as HindIII to ApaI fragments into the vector pGamma1 (FIG. 8). This vector contains the human Gamma 1 heavy chain constant region.

Evaluation of activities of CDR grafted genes

The activities of the CDR grafted genes were evaluated by expressing them in mammalian cells and purifying and quantitating the newly synthesised antibodies. The methodology for this is described next, followed by a description of the biochemical and cell based assays used for the biological characterisation of the antibodies.

a) Gene Expression in CHO cells

Chimeric and CDR grafted L243 was produced for biological evaluation by transient expression of heavy and light chain pairs after co-transfection into Chinese Hamster Ovary (CHO) cells using calcium phosphate precipitation.

On the day prior to transfection, semi-confluent flasks of CHO-L761 cells [Cockett, M. I., Bebbington, C. R. and Yarranton, G. T. 1991, Nucleic Acids Research 19, 319–325] were trypsinised, the cells counted and T75 flasks set up each with $10^7$ cells. On the next day, the culture medium was changed 3 hours before transfection. For transfection, the calcium phosphate precipitate was prepared by mixing 1.25 ml of 0.25M CaCl2 containing 50 µg of each of heavy and light chain expression vectors with 1.25 ml of 2× HBS (16.36 gm NaCl, 11.9 gm HOPES and 0.4 gm Na2HPO4 in 1 liter water with the pH adjusted to 7.1 with NaOH) and adding immediately into the medium on the cells. After 3 hours at 37° C. in a CO2 incubator, the medium and precipitate were removed and the cells shocked by the addition of 15 ml 15% glycerol in phosphate buffered saline (PBS) for 1 minute. The glycerol was removed, the cells washed once with PBS and incubated for 48–96 hours in 25 ml medium containing 10 mM sodium butyrate. Antibody was purified from the culture medium by binding to and elution from proteinA-Sepharose. Antibody concentration was determined using a human Ig ELISA (see below).

b) ELISA

For the ELISA, Nunc ELISA plates were coated overnight at 4° C. with a F(ab)2 fragment of a polyclonal goat anti-human Fc fragment specific antibody (Jackson Immuno-research, code 109-006-098) at 5 µg/ml in coating buffer (15 mM sodium carbonate, 35 mM sodium hydrogen carbonate, pH6.9). Uncoated antibody was removed by washing 5 times with distilled water. Samples and purified standards to be quantitated were diluted to approximately 1 µg/ml in conjugate buffer (0.1M Tris-HCl pH7.0, 0.1 M NaCl, 0.2% v/v Tween 20, 0.2% w/v Hammersten casein). The samples were titrated in the microtitre wells in 2-fold dilutions to give a final volume of 0.1 ml in each well and the plates incubated at room temperature for 1 hr with shaking. After the first incubation step the plates were washed 10 times with distilled water and then incubated for 1 hr as before with 0.1 ml of a mouse monoclonal anti-human kappa (clone GD12) peroxidase conjugated antibody (The Binding Site, code MP135) at a dilution of 1 in 700 in conjugate buffer. The plate was washed again and substrate solution (0.1 ml) added to each well. Substrate solution contained 150 µl N,N,N,N-tetramethylbenzidine (10 mg/ml in DMSO), 150 µl hydrogen peroxide (30% solution) in 10 ml 0.1M sodium acetate/sodium citrate, pH6.0. The plate was developed for 5–10 minutes until the absorbance at 630 nm was approximately 1.0 for the top standard. Absorbance at 630 nm was measured using a plate reader and the concentration of the sample determined by comparing the titration curves with those of the standard.

c) Competition Assay

The principle of this assay is that if the antigen binding region has been correctly transferred from the murine to human frameworks, then the CDR grafted antibody will compete equally well with a labelled chimeric antibody for binding to human MHC Class II. Any changes in the antigen binding potency will be revealed in this system.

Chimeric L243 was labelled with fluorescein (FITC) using the method of Wood et al [Wood, T., Thompson, S and Goldstein, G (1965), J. Immunol 95, 225–229]. All dilutions, manipulations and incubations were done in phosphate buffered saline (PBS, Gibco, UK) containing 0.1% sodium azide and 5% Fetal Calf serum (Sigma, UK). Serial dilutions of antibodies in 100 µl in RB polystyrene tubes (2052 12×75 mm Falcon, UK) were premixed with a constant amount of the FITC-labelled antibody (at a previously determined optimal concentration) and added to 5×10$^4$ indicator cells (JY B lymphoblastoid cell line bearing high levels of HLA-DR). Cells and antibody were incubated together at 4° C. for 30 minutes, washed twice and binding revealed using a Fluorescence Activated Cell Scanner (FACS Becton Dickinson). After appropriate analysis, median fluorescence intensity is plotted against antibody concentration.

FIG. 9 compares the ability of combinations of L243 heavy and light chains to compete with FITC-labelled chimeric L243 for binding to JY cells. All combinations were effective competitors although none of those containing CDR grafted heavy or light chains were as effective as the chimeric antibody itself. Thus, the combinations cH/gL1, gH/cL and gH/gL1 were 89%, 78% and 64% respectively, as effective as chimeric 1243 in this assay.

d) Determination of Affinity constants by Scatchard Analysis

L243 antibodies were titrated from 10 µg/ml in PBS, 5% fetal calf serum, 0.1% sodium azide in 1.5-fold dilutions (150 µl each) before incubation with 5×10$^4$ JY cells per titration point for 1 hour on ice. The cells were previously counted, washed and resuspended in the same medium as the samples. After incubation, the cells were washed with 5 ml of the above medium, spun down and the supernatant discarded. Bound antibody was revealed by addition of 100 µl of a 1/100 dilution of FITC conjugated anti-human Fc monoclonal (The Binding Site; code MF001). The cells were then incubated for 1 hour on ice and then the excess FITC conjugate removed by washing as before. Cells were dispersed in 250 µl of the same buffer and the median fluorescence intensity per cell was determined in a FACScan (Becton Dickinson) and calibrated using standard beads (Flow Cytometry standards Corporation). The number of molecules of antibody bound per cell at each antibody concentration was thus established and used to generate Scatchard plots. For the purpose of calculation, it was assumed that the valency of binding of the FITC conjugate to L243 was 1:1 and that the F/P ratio was 3.36 (as given by the manufacturer).

A Scatchard plot comparing the affinities of chimeric L243 (cH/cL), L243-gH/L243-gL1 and L243-gH/L243-gL2 is shown in FIG. 10. Chimeric L243 was found to have an apparent Kd of 4.1 nM while the CDR grafted antibodies containing gL1 and gL2 light chains had apparent Kd of 6.4nM and 9.6 nM respectively. The difference in Kd values of the antibodies with the two CDR grafted light chains reflects the contribution made by residues 45,49,70 and 71 that had been retained, in L243-gL1, from the parent light chain.

e) Antibody dependent cell mediated cytotoxicity.

The ability of chimeric and CDR grafted L243 to mediate antibody dependent cell cytotoxicity (ADCC) was compared. The principle of the experiment is that antibodies will mediate lysis of target cells bearing their cognate antigen if the Fc of the antibody is able to interact with Fc receptor bearing effector cells capable of cytotoxicity.

Effector cells are prepared fresh for each experiment. Human venous blood is drawn into endotoxin free tubes containing heparin. Peripheral blood mononuclear cells (PBMC) are prepared by density gradient centrifugation according to the manufacturers instructions (Pharmacia). PBMCs are adjusted to 1×10$^7$ cells/ml in RPMI 1640 medium (Gibco) containing 2 mM glutamine (Gibco, UK) and 10% fetal calf serum, in which all manipulations, dilutions are incubations are done.

Target cells (JY, see above) are labelled with 1 mCi Na$^{51}$Cr for 1 hour at room temperature, agitated every 15 minutes. The cells are then washed three times to remove free radiolabel and resuspended at 2×10$^6$ cells/ml. Serial antibody dilutions are prepared in duplicate in sterile U-bottomed 96 well microtitre plates (Falcon, UK) in 25 µl. Control wells containing medium only are also prepared to establish the spontaneous release of label giving the assay background. Target $^{51}$Cr labelled JY cells are added to all wells in 10 µl. The same number of JY cells are also added to wells containing 2% Triton X100 in water to establish the 100% release value. Target cells and antibody are incubated together and, after 30 minutes at room temperature, 25 µl effector cells are added to all wells (except the 100%) for a further 4 hours at 37° C. 100 µl of EDTA/saline at 4° C. is then added to stop any further cell killing, the microtitre plates are centrifuged at 200× g to pellet the intact cells and 100 µl of the supernatant is removed and counted in a gamma counter.

Percent cell lysis is calculated by subtracting the background from all values and then expressing them as a percentage of the adjusted maximum release. Replicates vary by less than 5%. Percent cell lysis is then plotted against antibody concentration.

A comparison of the activities of chimeric (cH/cL) and CDR grafted (gH/gL1) L243 human gamma 1 isotypes in the above assay is shown in FIG. 11. Both antibodies were effective mediators of cell lysis with maximal activity being achieved at antibody concentrations of less than 100 ng/ml. There was no significant difference between the activities of the two antibodies.

f) Immune function tests

Ex vivo T cell function experiments were performed where an interaction between MHC-11 and the T cell receptor was an obligatory requirement for T cell activation. Chimeric and CDR grafted L243 antibodies were compared in mixed lymphocyte reactions, which measures both naive and memory T cell activation, and in recall responses to tetanus toxoid which only measures a memory T cell response.

1) Mixed Lymphocyte reaction

The principle of the experiment is that when leucocytes from one individual are mixed with those of another individual which express different HLA alleles, they will recognise each other as foreign and the lymphocytes will become activated. This activation is dependent primarily on interactions between the CD3/TcR complex on T cells and the MHC Class II molecule on antigen presenting cells. L243 is known to inhibit this reaction.

Leucocytes are prepared fresh for each experiment. Human venous blood from two individuals is drawn into endotoxin free tubes containing heparin. Peripheral blood mononuclear cells (PBMC) are prepared by density centrifugation according to the manufacturers instructions (Pharmacia). PBMC are adjusted to $2 \times 10^6$ cells/ml in RPMI 1640 medium (Gibco, UK) containing 2 mM glutamine, 100 jig/ml penicillin/streptomycin and 10% fetal calf serum, in which all manipulations, dilutions and incubations are done. PBMC from one individual are irradiated with 3000 rads. These cells will be used to stimulate a response from those of the other individual.

Serial dilutions of antibodies are prepared in triplicate in sterile U-bottom 96 well microtitre plates (Falcon, UK) in 100 µl. Control wells containing either medium alone or 100 nM cyclosporin (Sandimmun, Sandoz) are also prepared to establish the maximum response and maximum inhibition respectively. Equal numbers of irradiated stimulators are responders are mixed together and 100 µl is added to each well. Wells with stimulator alone and responders alone are also set up as controls. The experiment is incubated at 37° C. in 100% humidity and 5% CO2 for 5 days. Response is measured by assessing cell proliferation during the last 18 hours of culture by incubation with 1 µC/well $^3$H-Thymidine (Amersham, UK), harvesting onto glass filter mats and counting using a beta counter.

When an MLR was carried out to compare the effectiveness of the Gamma 1 isotypes of chimeric and CDR grafted L243 as inhibitors of T cell activation, no significant differences were observed between the two antibodies (FIG. 12). Greater than 90% inhibition of the MLR was observed using 100 ng/ml of either antibody.

2) T cell recall response to Tetanus toxoid

The ability of chimeric and CDR grafted L243 to suppress a secondary response was assessed using a recall response to Tetanus toxin. The principle of the experiment is that T lymphocytes from an individual previously immunised with Tetanus toxoid (TT) will respond to TT when re-exposed ex vivo. This activation is dependent on the interaction between the CD3/TcR complex on T cells and the MHC Class II molecules on cells which process and present the antigen. L243 is known to inhibit this reaction.

PBMC are prepared as described above. Serial dilutions of antibodies are prepared in triplicate in sterile U-bottom 96 well microtitre plates in 100 µl. 50 µl containing an optimal concentration of TT, previously determined by experimentation, is added to all wells. Control wells containing medium only or 100 nM cyclosporin are also prepared to establish the maximum response and maximum inhibition, respectively. 50 µl PBMC are then added to each well. The experiment is incubated at 37° C. in 100% humidity and 5% CO2 for 7 days. Response is measured by assessing cell proliferation during the last 18 hours of culture by incubation with 1 µCi/well $^3$H-thymidine, harvesting onto glass filter mats and counting using a beta counter.

The results of an experiment comparing the ability of human gamma 1 isotypes of chimeric and CDR grafted L243 to inhibit the response to TT is shown in FIG. 13. Both antibodies were effective inhibitors of the T cell response to T7 and produced titration curves that were indistinguishable.

EXAMPLE 3

The ability of CDR grafted L243 with the alteration at position 235 i.e. [L235E] to mediate antibody dependent cell cytoxicity (ADCC) was measured essentially as described in Example 2. The results are shown in FIG. 15.

Similarly the CDR grafted L243 [L235E] antibody was tested in a mixed lymphocyte reaction and in recall response to tetanus toxoid essentially as described in Example 2. The results are provided in FIGS. 16 and 17.

Antibody Dependent Complement Mediated Cytotoxicity

The ability of the engineered variants of L243 to fix human complement was assessed using the technique of antibody dependent complement mediated cytotoxicity.

The principle of the experiment is that antibodies will mediate complement lysis of target cells bearing their cognate antigen if the Fc of the antibody is able to interact with the components of the (usually classical) complement cascade. The critical interaction is with the C1q molecule.

The source of complement in these experiments is human venous blood freshly drawn into endotoxin free glass bottles which is then allowed to clot at 37° C. for 1 hour. The clot is detached from the glass and then incubated at 4° C. for 2 hours to allow it to retract. The clot is then removed and the serum separated from the remaining red cells by centrifugation at 1000 g. Once prepared, the serum can be stored for up to one month at −20° C. without noticeable deterioration of potency.

All manipulations, dilutions and incubations are done in RPM1 1640 medium (Gibco UK) containing 2 mM Glutamine (Gibco UK) and 10% foetal calf serum (Sigma UK). Target cells (JY B lymphoblastoid cell line bearing high levels of HLA-DR) are labelled with 1 mCi Na$^{51}$Cr for 1 hour at room temperature, agitated every 15 min. The cells are then washed three times, to remove free radiolabel, and resuspended at $2 \times 10^6$/ml. Serial antibody dilutions are prepared in duplicate in V-bottom 96 well microtitre plates (ICN/Flow UK) in 25 ml. Control wells containing medium only are also prepared to establish the spontaneous release of label giving the assay back-ground. Target $^{51}$Cr labelled JY cells are added to all wells in 10 ml. The same number of JY cells are also added to wells containing 2% Triton x100 in water to establish the 100% release value. Target cells and antibody are incubated together and, after 1 hour at room temperature, 25 ml serum as a source of complement is added to all wells (except the 100%) for a further 1 hour at room temperature. 100 ml of EDTA saline at 4° C. is then added to stop any further cell killing, the microtitre plates are centrifuged at 200g to pellet the intact cells and 100ml supernatant is removed and counted in a gamma counter.

Percent cell lysis is calculated by subtracting the background from all values and then expressing them as a percentage of the adjusted maximum release. Replicates vary by less than 5%. Percent cell lysis is then plotted against antibody dilution.

The results (without subtraction of background) are shown in FIG. 18.

What is claimed is:

1. A CDR-grafted humanised antibody heavy chain comprising a variable domain wherein the complementarity determining regions (CDRs) and framework residues 67, 71, 72 and 75, as numbered according to Kabat, of said variable domain are from the mouse monoclonal antibody L243 heavy chain and the remainder of the immunoglobulin is from the heavy chain of a human immunoglobulin.

2. A CDR-grafted humanised antibody heavy chain according to claim 1 further wherein, in the variable domain, framework residues 27 and 69, as numbered according to Kabat, are from the mouse monoclonal antibody L243 heavy chain.

3. A CDR-grafted humanised antibody heavy chain according to claim 2 wherein the variable domain has the amino acid sequence shown in FIG. 7 (SEQ ID NO: 82).

4. A CDR-grafted humanised antibody heavy chain according to any one of claims 1 to 3 wherein, in the N-terminal region of the $C_H2$ domain of said heavy chain, residue 235, as numbered according to Kabat, is not leucine.

5. A CDR-grafted humanised antibody heavy chain according to claim 4 wherein, in the N-terminal region of the $C^H2$ domain of said heavy chain, residue 235, as numbered according to Kabat, is glutamic acid or alanine.

6. A CDR-grafted humanised antibody light chain comprising a variable domain where in the complementarity determining regions (CDRs ) and framework residues 45, 49, 70, 71, as numbered according to Kabat, of said variable domain are from the mouse monoclonal antibody L243 light chain and the remainder of the immunoglobulin is from the light chain of a human immunoglobulin.

7. A CDR-grafted humanised antibody light chain according to claim 6 wherein the variable domain has the amino acid sequence shown in FIG. 4 (SEQ ID NO:78).

8. A humanised antibody molecule having specificity of antigenic determinants dependent on the DRα chain, in which the variable domain of the heavy chain has the amino acid sequence shown in FIG. 7 (SEQ ID NO:82).

9. A humanised antibody molecule having specificity of antigenic determinants dependent on the DRα chain, in which the variable domain of the light chain has the amino acid sequence shown in FIG. 4 (SEQ ID NO:78).

10. A humanised antibody molecule having specificity of antigenic determinants dependent on the DRα chain, in which the variable domain of the heavy chain has The amino acid sequence shown in FIG. 7 (SEQ ID NO:92) and the variable domain ot the light chain has the amino acid sequence shown in FIG. 4 (SEQ ID NO:78).

11. A DNA sequence which encodes a heavy chain according to claim 3.

12. A DNA sequence which encodes a light chain according to claim 9.

13. A cloning or expression vector containing a DNA sequence according to claim 11.

14. A cloning or expression vector containing a DNA sequence according to claim 12.

15. A host cell transformed with a cloning or expression vector according to claim 13.

16. A host cell transformed with a cloning or expression vector according to claim 14.

17. A composition comprising a humanised antibody molecule according to any one of claims 8–10 and a pharmaceutically acceptable carrier.

* * * * *

UNITED STATES PATENT AND TRADEMARK OFFICE
CERTIFICATE OF CORRECTION

PATENT NO. : 6,180,377 B1
DATED : January 30, 2001
INVENTOR(S) : Susan A. Morgan, John S. Emtage, Mark W. Bodmer and Diljeet S. Athwal It is certified that error appears in the above-identified patent and that said Letters Patent is hereby corrected as shown below:

Title page,
Item [22], PCT Filed, please delete "Jun. 15, 1993" and insert -- Jun. 15, 1994 -- therefor.
Item [56], References Cited, OTHER PUBLICATIONS "Routledge, E. et al.," reference please delete "Homologou" and insert -- Homologous -- therefor.

Column 2,
Line 22, "WO 92/113831." should read -- WO 92/11383]. --.

Column 4,
Line 56, "$\leq 30\%$" should read -- $\leq 30\%$ --.
Line 56, "$\leq 20\%$" should read -- $\leq 20\%$ --.
Line 57, "$\leq 10\%$" should read -- $\leq 10\%$ --.

Column 5,
Line 17, "$\leq 20\%$" should read -- $\leq 20\%$ --.
Line 17, ">10%" should read -- $\leq 10\%$ --.
Line 66, "transfectec" should read -- transfected --.

Column 6,
Line 62, "Science 23" should read -- Science 239 --.
Line 63, "Nature =323" should read -- Nature 323 --.

Column 7,
Line 1, "cellVvector" should read -- cell/vector --.
Line 39, "L1243" should read -- L243 --.

Column 9,
Line 66, "1L243" should read -- L243 --.

Column 10,
Line 19, "Series UT" should read -- Series TT --.
Line 27, "nucleotide" should read -- nucleotide SEQ ID NO: 83 --.
Line 28, "NO: 84" should read -- NO: 85 --.
Line 31, "[1L235E]" should read -- [L235E] --.
Line 40, "G[1 L235E]" should read -- G1 [L235E] --.
Line 56, "I243" should read -- L243 --.

UNITED STATES PATENT AND TRADEMARK OFFICE
CERTIFICATE OF CORRECTION

PATENT NO.    : 6,180,377 B1
DATED         : January 30, 2001
INVENTOR(S)   : Susan A. Morgan, John S. Emtage, Mark W. Bodmer and Diljeet S. Athwal It is certified that error appears in the above-identified patent and that said Letters Patent is hereby corrected as shown below:

Column 11,
Line 35, "2011" should read -- 20µ1 --.
Line 42, "950C" should read -- 95°C --.
Line 61, "Spil" should read -- Sp11 --.

Column 12,
Line 14, "1 λ1 cDNA" should read -- 1 µ1 cDNA --.
Line 23, "Bi" should read -- B1 --.
Line 33, "Spil." should read -- Sp11. --.

Column 13,
Line 37, "5'CCCCCCTCGAGTTCAGGTGCTGAGGMG3'" should read -- 5'CCCCCCTCGAGTTCAGGTGCTGAGGAAG3' --.
Line 46, "5'GCACCTGMCTCCTGGGTGCACCGT-" should read -- 5'GCACCTGAACTCCTGGGTGCACCGT- --.

Column 17,
Line 17, "5'GGACTGTTCGMGCCGCCACC3' SEQ ID NO: 95" should read -- 5'GGACTGTTCGAAGCCGCCACC3' SEQ m NO: 95 --.

Column 18,
Delete lines 52 and 53.
Line 59, "WYRQKQGKSPQLLUF SEQ ID NO: 39" should read -- WYRQKQGKSPQLLVF SEQ ID NO: 39 --.

UNITED STATES PATENT AND TRADEMARK OFFICE
CERTIFICATE OF CORRECTION

PATENT NO.     : 6,180,377 B1
DATED          : January 30, 2001
INVENTOR(S)    : Susan A. Morgan, John S. Emtage, Mark W. Bodmer and Diljeet S. Athwal It is certified that error appears in the above-identified patent and that said Letters Patent is hereby corrected as shown below:

Column 19,
Line 12, "R5043: 5'GTRGGRGRCCGGGTCRCCRTCRCRT-" should read
-- R5043: 5'GTAGGAGACCGGGTCACCATCACAT- --.
Line 13, "GTCGRGCRR3' SEQ ID NO: 45" should read -- GTCGAGCAA3' SEQ ID NO: 45 --.
Line 14, "R5044: 5'CTGRGGRGCTTTTCCTGGTTTCTGCTGR-" should read -- R5044: 5'CTGAGGAGCTTTTCCTGGTTTCTGCTGA- --.
Line 15, "TRCCRTGCTARR3' SEQ ID NO: 45" should read -- TACCATGCTAAA3' SEQ II) NO: 45 --.
Line 16, "R5045: 5'RRRCCRGGRRRRGCTCCTCRGCTCCT-" should read -- R5045: 5'AAACCRGGAAAAGCTCCTCAGCTCCT- --.
Line 17, "GRTCTTTGCTGCRTC3' SEQ ID NO: 46" should
read -- GATCTTTGCTGCATC3' SEQ 11) NO: 46 --.
Line 18, "R5046: 5'CTTCTGGCTGCRGGCTGGRGRT-" should read -- R5046: 5'CTTCTGGCTGCAGGCTGGAGATAGT- --.
Line 19, "TRGGGTRTRCTGTGTGCC3' SEQ ED NO: 47" should read
-- TAGGGTATACTGTGTGCC3' SEQ ID NO: 47 --.
Line 20, "R5047: 5'CTTCRGCCTGCRGCCRGRRGRTTTTGC-" should read -- R5047: 5'CTTCAGCCTGCAGCCAGAAGATTTTGC- --.
Line 21, "TRCTTRTTRCTGTCRR3' SEQ ID NO: 48" should read -- TACTTAT-TACTGTCAA3' SEQ ID NO: 48 --.
Line 22, "R5048: 5'GGGCCGCTRCCGTRCGTTTTRGTTC-" should read -- R5048: 5'GGGCCGCTACCGTACGTTTTAGTTC- --.
Line 23, "CRCTTTGGTGCCTTGRCCGHR3' SEQ ID NO: 49" should
read -- CACTTTGGTGCCTTGACCGHA3' SEQ ID NO: 49 --.
Line 31, "reaction 35" should read -- reaction --.
Line 60, "R1053: 5'GCTGACRGRCTRRCRGRCTGTTCC3'SEQ ID" should
read -- R1053: 5'GCTGACAGACTAACAGACTGTTCC3' SEQ ID --.
Line 62, "R5350: 5'TCTRGRTGGCRCRCCRTCT-" should read
-- R5350: 5'TCTAGATGGCACACCATCT- --.
Line 63, "GCTARGTTTGRTGCRGCATRGRTCAG-" should
read -- GCTAAGTTTGATGCAGCATAGATCAG --.
Line 64, "GRGCTTAGG AGCY SEQ ID NO: 51" should read -- GAGCTTAGG AGCY SEQ ID NO: 51 --.
Line 65, "R5349: 5'GCRGRTGGTGTGCCRTCTRGRTTCRGTG-" should read -- R5349: 5'GCAGATGGTGTGCCATCTAGATTCAGTG- --.
Line 66, "GCRGTGGRTCRGGCRCRGRCTTTACCCTRRC3'" should read
-- GCAGTGGATCAGGCACAGACTTTACC CTAAC3'--.

UNITED STATES PATENT AND TRADEMARK OFFICE
CERTIFICATE OF CORRECTION

PATENT NO.     : 6,180,377 B1
DATED          : January 30, 2001
INVENTOR(S)    : Susan A. Morgan, John S. Emtage, Mark W. Bodmer and Diljeet S. Athwal It is certified that error appears in the above-identified patent and that said Letters Patent is hereby corrected as shown below:

Column 20,
Line 7, "R684: 5'TTCRACTGCTCATCRGRT3' SEQ ID NO: 53" should read
-- R684: 5'TTCAACTGCTCATCAGAT3' SEQ ID NO: 53 --.
Delete lines 63 through 66.

Column 21,
Line 4, "QVQLVQSGAEUKKPGASUKUSCKASGYTFT SEQ ID NO: 54" should
read -- QVQLVQSGAEVKKPGASVKVSCHASGYTFT SEQ ID NO: 54 --.
Line 7, "WVRQRPGQGLEWMG SEQ ID N0:56" should
read -- WVAQAGQGLEWMG SEQ 1D N0:56 --.
Line 12, "RUTITADTSTSTAYMELSSLRSEDTRVYYCAA SEQ ID N0:58" should
read -- AVTITADTSTSTAYMELSSLASEDTAVYYCAA SEQ ID N0:58 --.
Line 13, "RFAFSLETSASTRYLQINNLKNEDTAKYECAR SEQ ID NO:59" should read
-- AFAFSLETSASTAYLQINNLKNEDTAKYFCAA SEQ ID NO:59 --.

Delete lines 17 through 22,
Line 45, "CAGGAAGRACAGGAACACC CAAGACCACTC-" should read
-- CAGGAAGAACAGGAACACC CAAGACCACTC- --.
Line 52, "TGTGTRTGTATTAATCCA TCCCATCCACTC-" should
read -- TGTGTATGTATTAATCCA TCCCATCCACTC- --.
Line 59, "CCCAGTRGTCGAA3' SEQ ID NO: 72" should read
-- CCCAGTAGTCGAA3' SEQ ID NO: 72 --.

Column 22,
Line 19, "Hindlil" should read -- HindIII --.
Line 28, "L43gH" should read -- L243gH --.
Line 56, "HOPES" should read -- HEPES --.

Column 23,
Line 60, "1243" should read -- L243 --.

Column 25,
Line 31, " jig/ml" should read -- $\mu$g/ml --.
Line 47, "$\mu$C/" should read -- $\mu$Ci/ --.

Column 26,
Line 17, "T7" should read -- TT --.

UNITED STATES PATENT AND TRADEMARK OFFICE
CERTIFICATE OF CORRECTION

PATENT NO.    : 6,180,377 B1
DATED         : January 30, 2001
INVENTOR(S)   : Susan A. Morgan, John S. Emtage, Mark W. Bodmer and Diljeet S. Athwal It is certified that error appears in the above-identified patent and that said Letters Patent is hereby corrected as shown below:

Column 27,
Line 2, "20Og" should read -- 200g --.
Line 2, "1 00ml" should read -- 100ml --.

Column 75,
Line 41, "$C^H2$" should read -- $C_H2$ --.

Column 76,
Line 30, "The amino" should read -- the amino--.
Line 31, "(SEQ ID NO:92)" should read -- (SEQ ID NO:82) --.

Signed and Sealed this

Twenty-first Day of September, 2004

JON W. DUDAS
*Director of the United States Patent and Trademark Office*

UNITED STATES PATENT AND TRADEMARK OFFICE
CERTIFICATE OF CORRECTION

PATENT NO.   : 6,180,377 B1
DATED        : January 30, 2001
INVENTOR(S)  : Susan A. Morgan, John S. Emtage, Mark W. Bodmer and Diljeet S. Athwal It is certified that error appears in the above-identified patent and that said Letters Patent is hereby corrected as shown below:

Title page,
Item [22], PCT Filed, please delete "Jun. 15, 1993" and insert -- Jun. 15, 1994 -- therefor.
Item [56], References Cited, OTHER PUBLICATIONS "Routledge, E. et al.," reference please delete "Homologou" and insert -- Homologous -- therefor.

Column 2,
Line 22, "WO 92/113831." should read -- WO 92/11383]. --.

Column 4,
Line 56, "$\leqq 30\%$" should read -- $\leq 30\%$ --.
Line 56, "$\leqq 20\%$" should read -- $\leq 20\%$ --.
Line 57, "$\leqq 10\%$" should read -- $\leq 10\%$ --.

Column 5,
Line 17, "$\leqq 20\%$" should read -- $\leq 20\%$ --.
Line 17, ">10%" should read -- $\leq 10\%$ --.
Line 66, "transfectec" should read -- transfected --.

Column 6,
Line 62, "Science 23" should read -- Science 239 --.
Line 63, "Nature =323" should read -- Nature 323 --.

Column 7,
Line 1, "cellVvector" should read -- cell/vector --.
Line 39, "L1243" should read -- L243 --.

Column 9,
Line 66, "1L243" should read -- L243 --.

Column 10,
Line 19, "Series UT" should read -- Series TT --.
Line 27, "nucleotide" should read -- nucleotide SEQ ID NO: 83 --.
Line 28, "NO: 84" should read -- NO: 85 --.
Line 31, "[1L235E]" should read -- [L235E] --.
Line 40, "G[1 L235E]" should read -- G1 [L235E] --.
Line 56, "I243" should read -- L243 --.

UNITED STATES PATENT AND TRADEMARK OFFICE
CERTIFICATE OF CORRECTION

PATENT NO.    : 6,180,377 B1
DATED         : January 30, 2001
INVENTOR(S)   : Susan A. Morgan, John S. Emtage, Mark W. Bodmer and Diljeet S. Athwal It is certified that error appears in the above-identified patent and that said Letters Patent is hereby corrected as shown below:

Column 11,
Line 35, "2011" should read -- 20µ1 --.
Line 42, "950C" should read -- 95°C --.
Line 61, "Spil" should read -- Sp11 --.

Column 12,
Line 14, "1 λ1 cDNA" should read -- 1 µ1 cDNA --.
Line 23, "Bi" should read -- B1 --.
Line 33, "Spil." should read -- Sp11. --.

Column 13,
Line 37, "5'CCCCCCTCGAGTTCAGGTGCTGAGGMG3'" should
read -- 5'CCCCCCTCGAGTTCAGGTGCTGAGGAAG3' --.
Line 46, "5'GCACCTGMCTCCTGGGTGCACCGT-" should read
-- 5'GCACCTGAACTCCTGGGTGCACCGT- --.

Column 17,
Line 17, "5'GGACTGTTCGMGCCGCCACC3' SEQ ID NO: 95" should read
-- 5'GGACTGTTCGAAGCCGCCACC3' SEQ ID NO: 95 --.

Column 18,
Delete lines 52 and 53.

Line 59,  "WYRQKQGKSPQLLUF SEQ ID NO: 39" should read
-- WYRQKQGKSPQLLVF SEQ ID NO: 39 --.

UNITED STATES PATENT AND TRADEMARK OFFICE
CERTIFICATE OF CORRECTION

PATENT NO.   : 6,180,377 B1
DATED        : January 30, 2001
INVENTOR(S)  : Susan A. Morgan, John S. Emtage, Mark W. Bodmer and Diljeet S. Athwal It is certified that error appears in the above-identified patent and that said Letters Patent is hereby corrected as shown below:

Column 19,
Line 12, "R5043: 5'GTRGGRGRCCGGGTCRCCRTCRCRT-" should read
-- R5043: 5'GTAGGAGACCGGGTCACCATCACAT- --.
Line 13, "GTCGRGCRR3' SEQ ID NO: 45" should read -- GTCGAGCAA3' SEQ ID NO: 45 --.
Line 14, "R5044: 5'CTGRGGRGCTTTTCCTGGTTTCTGCTGR-" should
read -- R5044: 5'CTGAGGAGCTTTTCCTGGTTTCTGCTGA- --.
Line 15, "TRCCRTGCTARR3' SEQ ID NO: 45" should read -- TACCATGCTAAA3' SEQ ID NO: 45 --.
Line 16, "R5045: 5'RRRCCRGGRRRRGCTCCTCRGCTCCT-" should read -- R5045: 5'AAACCRGGAAAAGCTCCTCAGCTCCT- --.
Line 17, "GRTCTTTGCTGCRTC3' SEQ ID NO: 46" should
read -- GATCTTTGCTGCATC3' SEQ ID NO: 46 --.
Line 18, "R5046: 5'CTTCTGGCTGCRGGCTGGRGRT-" should read -- R5046: 5'CTTCTGGCTGCAGGCTGGAGATAGT- --.
Line 19, "TRGGGTRTRCTGTGTGCC3' SEQ ED NO: 47" should read
-- TAGGGTATACTGTGTGCC3' SEQ ID NO: 47 --.
Line 20, "R5047: 5'CTTCRGCCTGCRGCCRGRRGRTTTTGC-" should read -- R5047: 5'CTTCAGCCTGCAGCCAGAAGATTTTGC- --.
Line 21, "TRCTTRTTRCTGTCRR3' SEQ ID NO: 48" should read
-- TACTTATTACTGTCAA3' SEQ ID NO: 48 --.
Line 22, "R5048: 5'GGGCCGCTRCCGTRCGTTTTRGTTC-" should read -- R5048: 5'GGGCCGCTACCGTACGTTTTAGTTC- --.
Line 23, "CRCTTTGGTGCCTTGRCCGHR3' SEQ ID NO: 49" should
read -- CACTTTGGTGCCTTGACCGHA3' SEQ ID NO: 49 --.
Line 31, "reaction 35" should read -- reaction --.
Line 60, "R1053: 5'GCTGACRGRCTRRCRGRCTGTTCC3'SEQ ID" should
read -- R1053: 5'GCTGACAGACTAACAGACTGTTCC3' SEQ ID --.
Line 62, "R5350: 5'TCTRGRTGGCRCRCCRTCT-" should read
-- R5350: 5'TCTAGATGGCACACCATCT- --.
Line 63, "GCTARGTTTGRTGCRGCATRGRTCAG-" should
read -- GCTAAGTTTGATGCAGCATAGATCAG --.
Line 64, "GRGCTTAGG AGCY SEQ ID NO: 51" should read -- GAGCTTAGG AGC3'SEQ ID NO: 51 --.
Line 65, "R5349: 5'GCRGRTGGTGTGCCRTCTRGRTTCRGTG-" should
read -- R5349: 5'GCAGATGGTGTGCCATCTAGATTCAGTG- --.
Line 66, "GCRGTGGRTCRGGCRCRGRCTTTACCCTRRC3'" should read
-- GCAGTGGATCAGGCACAGACTTTACC CTAAC3'--.

UNITED STATES PATENT AND TRADEMARK OFFICE
CERTIFICATE OF CORRECTION

PATENT NO. : 6,180,377 B1
DATED : January 30, 2001
INVENTOR(S) : Susan A. Morgan, John S. Emtage, Mark W. Bodmer and Diljeet S. Athwal It is certified that error appears in the above-identified patent and that said Letters Patent is hereby corrected as shown below:

Column 20,
Line 7, "R684: 5'TTCRACTGCTCATCRGRT3' SEQ ID NO: 53" should read
-- R684: 5'TTCAACTGCTCATCAGAT3' SEQ ID NO: 53 --.
Delete lines 63 through 66.

Column 21,
Line 4, "QVQLVQSGAEUKKPGASUKUSCKASGYTFT SEQ ID NO: 54" should
read -- QVQLVQSGAEVKKPGASVKVSCHASGYTFT SEQ ID NO: 54 --.
Line 7, "WVRQRPGQGLEWMG SEQ ID N0:56" should
read -- WVAQAGQGLEWMG SEQ 1D N0:56 --.
Line 12, "RUTITADTSTSTAYMELSSLRSEDTRVYYCAA SEQ ID N0:58" should
read -- AVTITADTSTSTAYMELSSLASEDTAVYYCAA SEQ ID N0:58 --.
Line 13, "RFAFSLETSASTRYLQINNLKNEDTAKYFCAR SEQ ID NO:59" should read
-- AFAFSLETSASTAYLQINNLKNEDTAKYFCAA SEQ ID NO:59 --.

Delete lines 17 through 22.
Line 45, "CAGGAAGRACAGGAACACC CAAGACCACTC-" should read
-- CAGGAAGAACAGGAACACC CAAGACCACTC- --.
Line 52, "TGTGTRTGTATTAATCCA TCCCATCCACTC-" should
read -- TGTGTATGTATTAATCCA TCCCATCCACTC- --.
Line 59, "CCCAGTRGTCGAA3' SEQ ID NO: 72" should read
-- CCCAGTAGTCGAA3' SEQ ID NO: 72 --.

Column 22,
Line 19, "Hindlil" should read -- HindIII --.
Line 28, "L43gH" should read -- L243gH --.
Line 56, "HOPES" should read -- HEPES --.

Column 23,
Line 60, "1243" should read -- L243 --.

Column 25,
Line 31, " jig/ml" should read -- $\mu$g/ml --.
Line 47, "$\mu$C/" should read -- $\mu$Ci/ --.

Column 26,
Line 17, "T7" should read -- TT --.

UNITED STATES PATENT AND TRADEMARK OFFICE
CERTIFICATE OF CORRECTION

PATENT NO. : 6,180,377 B1
DATED : January 30, 2001
INVENTOR(S) : Susan A. Morgan, John S. Emtage, Mark W. Bodmer and Diljeet S. Athwal It is certified that error appears in the above-identified patent and that said Letters Patent is hereby corrected as shown below:

Column 27,
Line 2, "20Og" should read -- 200g --.
Line 2, "1 00ml" should read -- 100ml --.

Column 75,
Line 41, "$C^H 2$" should read -- $C_H 2$ --.

Column 76,
Line 30, "The amino" should read -- the amino --.
Line 31, "(SEQ ID NO:92)" should read -- (SEQ ID NO:82) --.

This certificate supersedes Certificate of Correction issued September 21, 2004.

Signed and Sealed this

Third Day of May, 2005

JON W. DUDAS
*Director of the United States Patent and Trademark Office*